United States Patent
Finsinger et al.

(10) Patent No.: US 8,268,845 B2
(45) Date of Patent: Sep. 18, 2012

(54) TETRAHYDRO- AND DIHYDROQUINAZOLINONES

(75) Inventors: Dirk Finsinger, Darmstadt (DE); Armin De Meijere, Göttingen (DE)

(73) Assignee: Merck Patent GmbH, Darmstadt (DE)

( * ) Notice: Subject to any disclaimer, the term of this patent is extended or adjusted under 35 U.S.C. 154(b) by 106 days.

(21) Appl. No.: 11/908,220

(22) PCT Filed: Feb. 14, 2006

(86) PCT No.: PCT/EP2006/001327
§ 371 (c)(1),
(2), (4) Date: Aug. 4, 2009

(87) PCT Pub. No.: WO2006/094604
PCT Pub. Date: Sep. 14, 2006

(65) Prior Publication Data
US 2009/0318444 A1     Dec. 24, 2009

(30) Foreign Application Priority Data
Mar. 11, 2005   (EP) .................................... 05005351

(51) Int. Cl.
*A61K 31/517*   (2006.01)

(52) U.S. Cl. .................................. 514/266.31; 544/289

(58) Field of Classification Search .................. 544/289
See application file for complete search history.

(56) References Cited

FOREIGN PATENT DOCUMENTS

| | | |
|---|---|---|
| EP | 1 142 881 A1 | 10/2001 |
| JP | 5-163250 A | 6/1993 |

OTHER PUBLICATIONS

West, Anthony R., Solid State Chemistry and its Applications, Wiley, New York, 1988, pp. 358 and 365.*

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

J. Degraw et al., "Potential Anticancer Agents. XXIV: Tetrahydroquinazoline Analogs of Tetrahydrofolic Acid", Journal of Organic Chemistry, vol. 24 (1959) pp. 1632-1640.

M. Notzel et al., "Domino Reactions of Amidines With Methyl 2-Chloro-2-Cyclopropylideneacetate as an Efficient Access to Cyclobutene-Annelated Pyrimidinones", Organic Letters, vol. 4, No. 5 (2002) pp. 839-841.

Database Beilstein XP002379075, Database Accession No. 22944, J. Indian Chem. Soc., Vol. 4 (1927) pp. 156.

Final Rejection dated Jun. 5, 2012 from Divisional U.S. Appl. No. 13/085,054 filed on Apr. 12, 2011.

* cited by examiner

*Primary Examiner* — James O Wilson
*Assistant Examiner* — Brian McDowell
(74) *Attorney, Agent, or Firm* — Millen, White, Zelano & Branigan, P.C.

(57) ABSTRACT

The present invention relates to the use of tetrahydro- and dihydroquinazolinones of formula I as protein kinase activators or inhibitors, a method for their manufacture, their use for the preparation of a medicament for the treatment of diseases, their use for the manufacture of a pharmaceutical composition and new tetrahydro- and dihydroquinazolinones.

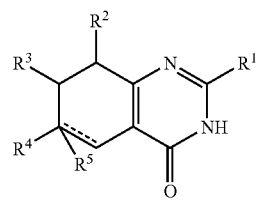

19 Claims, No Drawings

TETRAHYDRO- AND DIHYDROQUINAZOLINONES

FIELD OF THE INVENTION

The present invention relates to the use of tetrahydro- and dihydroquinazolinones of formula I as protein kinase activators or inhibitors, a method for their manufacture, their use for the preparation of a medicament for the treatment of diseases, their use for the manufacture of a pharmaceutical composition and new tetrahydro- and dihydroquinazolinones.

BACKGROUND OF THE INVENTION

Folic acid, one of the important B vitamins, is a precursor for the biogenetic synthesis of the cofactor, tetrahydrofolic acid conjugate. This later in turn, serves both as a formyl and hydroxymethyl transfer agent in a variety of biological system (B. R. Baker, L. Goodman, R. Koehler, J. Amer. Chem. Soc. 1958, 80, 5779-5786). The analogue 5,8-dideaza-5,6,7,8-tetrahydrofolic acid or the 2-substituted tetrahydroquinazolinones have attracted considerable attention in chemistry (A. Gangjee, A. Vasudevan, J. Heterocyclic Chem. 1997, 34, 1669-1676; G. Bernath, J. Kobor, J. Lazar, F. Fülöp, J. Heterocyclic Chem. 1996, 33, 1983-1988; G. Bernath, T. Janaky, G. Goendoes, J. Lazar, Z. Ecsery, Pharmazie 1983, 38, 270-271; T. Nishio, M. Fujisawa, Y. Omote, J. Chem. Soc., Perkin Trans. 1, 1987, 2523-2529) and biology (T. Sekiya, H. Hiranuma, M. Uchide, S. Hata, S. Yamada, Chem. Pharma Bull. 1981, 29, 948-954; F. Claudi, G. Giorgioni, L. Scoccia, R. Ciccocuppo, I. Panocka, Eur. J. Med. Chem. 1997, 32, 651-660).

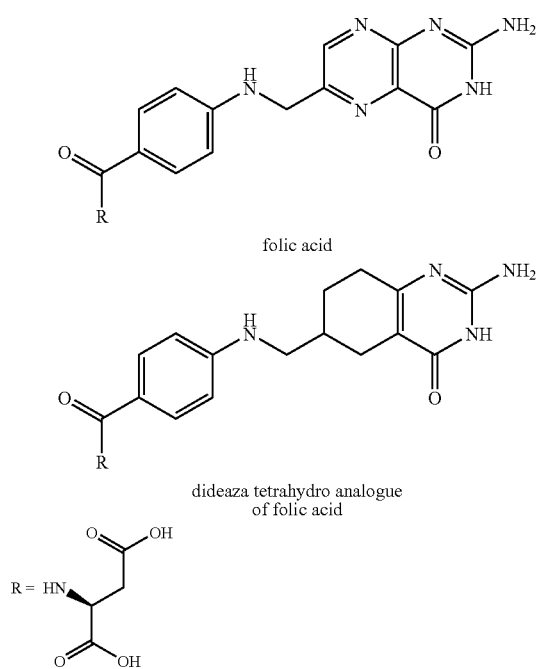

A wide range of biological activities has been discovered for such compounds: anticancer properties, antimicrobial activity against *Streptococcus feacium*, inhibition of dihydrofolate reductive and thymidilate synthase (M. G. Nair, R. Dhawan, M. Ghazala, T. I. Kalman, R. Ferone, Y. Agumont, R. L. Kisliuk, J. Med. Chem. 1987, 30, 1256-1261), as well as an ability to be a good substrate for partially purified mouse liver folylpolyglutamate synthetase (A. Rosowsky, R. A. Forsch, R. G. Moran, J. Med. Chem. 1989, 32, 709-715). The WO0046214 describes tetrahydroquinazolinones for the treatment of cardiovascular disorders. The WO042025 describes tetrahydroquinazolinones for the treatment and prevention of brain diseases. The WO04034972 describes quinazolinone-like derivatives as kinesin spindle protein modulators.

Although there are some known ways to prepare tetrahydroquinazolinone derivatives (Y. Sanemitsu, S. Kawamura, J. Org. Chem. 1993, 58: 414-418; G. Bernath, F. Fülöp, Synthesis, 1985: 1148-1149), a method starting from the Michael addition of amidine to the highly reactive acrylate analogue, methyl 2-chloro-2-cyclopropylidineacetate, has not previously been reported by other research groups (M. Limbach, S. Dalai, A. de Meijere, Adv. Synth. Catal. 2004, 346: 760-766. For an overview of chemistry of 1 see: A. de Meijere, S. I. Kozhushkov, L. P. Hadjiarapoglou, Topics Curr. Chem. 2000, 207: 149-227). Recently we described a versatile method for the synthesis of cyclobutene annelated pyrimidinones via Michael addition of amidines to compounds of formula I. However, the subsequent thermal cyclobutene ring opening followed by a Diels-Alder reaction led to inseparable mixtures (M. Nötzel, K. Rauch, T. Labahn, A. de Meijere, Org. Lett. 2002, 4, 839-841).

Protein kinases are involved in signaling pathways for such important cellular activities as responses to extracellular signals and cell cycle checkpoints. Inhibition or activation of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in the signaling mediated by protein kinases. Such conditions include those associated with defects in cell cycle regulation or in response to extracellular signals, e.g., immunological disorders, autoimmune and immunodeficiency diseases; hyperproliferative disorders, which may include psoriasis, arthritis, inflammation, endometriosis, scarring, cancer, etc. Therefore, compounds, which are active in modulating purified kinase proteins, e.g., there is a modulation in the phosphorylation of a specific substrate in the presence of the compound, can be used for the treatment of protein kinase-dependent diseases and conditions, such as cancer, tumour growth, arteriosclerosis, age-related macular degeneration, diabetic retinopathy, inflammatory diseases and the like, in mammals.

Thus, as there remains a need in advantageous therapeutics, a preferred object of the present invention was to provide new pharmaceutically active compounds or compounds for new medicinal indications. A further object of the present invention was to provide a new method for the preparation of tetrahydro- and dihydroquinazolinones.

BRIEF DESCRIPTION OF THE INVENTION

Surprisingly, the compounds of the general formula I show pharmaceutical activities as they act as effective modulators (activators or inhibitors) of one or more protein kinases selected from the group of Raf, Mek, PKB, Tie2, PDGFR and VEGFR.

Therefore, an embodiment of the present invention is the use of a compound of the formula I,

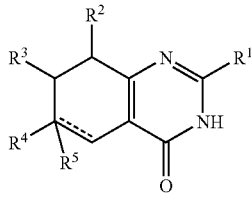

wherein
----- is a single or a double bond,
$R^1$ is $Ar^1$, S-A or Het,
$R^2$ is H or A,
$R^3$ is H, A, CN, COOA, $(CH)_n$NHA, $(CH)_n$NA$_2$, CONH$_2$, CONHA, CONA$_2$, $(CH)_n$NHCONH$_2$, $(CH)_n$NNHCONHA or $(CH)_n$NHCONA$_2$,
$R^4$ is H, SO$_2$Ar$^2$, A, CN, COOA, $(CH)_n$NHA, $(CH)_n$NA$_2$, CONH$_2$, CONHA, CONA$_2$, $(CH)_n$NHCONH$_2$, $(CH)_n$NHCONHA, or $(CH)_n$NHCONA$_2$,
$R^5$ is H or A, or is absent, if ----- is a double bond,
$Ar^1$ is phenyl, which optionally is substituted by one or more substituents, selected from the group consisting Hal, S-A, Ph, —O(CH$_2$)$_n$-Ph, —N(CH$_2$Ph)$_2$,
$Ar^2$ is phenyl, which optionally is substituted by one or more substituents, selected from the group consisting of Hal, A, COOA,
A is alkyl or cycloalkyl with 1-12 C-atoms, wherein optionally 1-5 H atoms are replaced by F and/or Cl,
Het is a mono- or bicyclic, saturated, unsaturated or aromatic heterocyclic residue which optionally is substituted by one or more substituents, selected from the group consisting of OOCA, Hal, A, (CH$_2$)$_n$Ar$^2$, (CH$_2$)$_n$cycloalkyl, OA, NH$_2$, NHA, NA$_2$, NO$_2$, CN, COOH, COOA, CONH$_2$, CONHA, CONA$_2$, NHCOA, NHCONH$_2$, NHCONA$_2$, NHSO$_2$A, COA, SO$_2$NH$_2$, SO$_2$NHA, SO$_2$NA$_2$, SO$_2$A, SOA$_2$, CF$_3$, OCF$_3$ and SCF$_3$, with the proviso that said heterocyclic residue contains 1, 2, 3 or 4 N-, O- and/or S-atoms, at least comprising one N-atom and Het is linked via N to the pyrimidinone ring system,
Hal is F, Cl, Br or I,
n is 0, 1 or 2,
or the physiologically acceptable salts, derivatives, prodrugs, solvates and stereoisomers thereof, including mixtures thereof in all ratios, for the preparation of a medicament for the treatment and/or prevention of disorders, characterized in that the disorders are selected from the group consisting of hyperproliferative and non-hyperproliferative disorders.

A preferred embodiment of the present invention is the use of a compound of the formula I, characterized in that the compound is selected from the group consisting of
a) 6-Benzenesulfonyl-2-phenyl-5,6,7,8-tetrahydroquinazolin-4(3H)-one
b) 6-Benzenesulfonyl-2-(p-chlorophenyl)-5,6,7,8-tetrahydroquinazolin-4(3H)-one
c) 6-Benzenesulfonyl-2-(o-bromophenyl)-5,6,7,8-tetrahydroquinazolin-4(3H)-one
d) 6-Benzenesulfonyl-2-(o-fluorophenyl)-5,6,7,8-tetrahydroquinazolin-4(3H)-one
e) 6-Benzenesulfonyl-2-[(p-benzyloxy)phenyl]-5,6,7,8-tetrahydroquinazolin-4(3H)one
f) 6-Benzenesulfonyl-2-(o-biphenyl)-5,6,7,8-tetrahydroquinazolin-4(3H)-one
g) 6-Benzenesulfonyl-2-(methylthio)-5,6,7,8-tetrahydroquinazolin-4(3H)-one
h) 2-Phenyl-7,8-dihydroquinazolin-4(3H)-one
i) 2-(p-Chlorophenyl)-7,8-dihydroquinazolin-4(3H)-one
j) 2-(o-Bromophenyl)-7,8-dihydroquinazolin-4(3H)-one
k) 2-(o-Fluorophenyl)-7,8-dihydroquinazolin-4(3H)-one
l) 2-(p-Benzoyloxyphenyl)-7,8-dihydroquinazolin-4(3H)-one
m) 2-(o-Biphenyl)-7,8-dihydroquinazolin-4(3H)-one
n) 2-Methylthio-7,8-dihydroquinazolin-4(3H)-one
o) 2-Phenyl-5,6,7,8-tetrahydroquinazolin-4(3)-one
p) 2-(p-Chlorophenyl)-5,6,7,8-tetrahydroquinazolin-4(3)-one
q) 2-(o-Bromophenyl)-5,6,7,8-tetrahydroquinazolin-4(3)-one
r) 2-(o-Fluorophenyl)-5,6,7,8-tetrahydroquinazolin-4(3)-one
s) 2-[(p-Benzoyloxy)phenyl]-5,6,7,8-tetrahydroquinazolin-4(3)-one
t) 2-(o-Biphenyl)-5,6,7,8-tetrahydroquinazolin-4(3)-one
u) 6-Benzenesulfonyl-6-methyl-2-phenyl-5,6,7,8-tetrahydroquinazolin-4(3H)-one
v) 6-Benzenesulfonyl-6-ethyl-2-phenyl-5,6,7,8-tetrahydroquinazolin-4(3H)-one
w) 6-Methyl-2-phenyl-5,6,7,8-tetrahydroquinazolin-4(3H)-one
x) 6-Ethyl-2-phenyl-5,6,7,8-tetrahydroquinazolin-4(3H)-one
y) 6-Methyl-2-phenyl-7,8-dihydroquinazolin-4(3H)-one
z) 6-Ethyl-2-phenyl-7,8-dihydroquinazolin-4(3H)-one
aa) 6-Benzenesulfonyl-7-methyl-2-phenyl-5,6,7,8-tetrahydroquinazolin-4(3H)one
bb) 6-Benzenesulfonyl-2-(morpholine-4-yl)-5,6,7,8-tetrahydroquinazolin-4(3H)-one
cc) 2-(4-benzylpiperazin-1-yl)-6-Benzenesulfonyl-5,6,7,8-tetrahydroquinazolin-4(3H)-one
dd) 6-Benzenesulfonyl-2-(4-methylpiperazin-1-yl)-5,6,7,8-tetrahydroquinazolin-4(3H)-one
ee) 2-(Morpholin-4-yl)-5,6,7,8-tetrahydroquinazolin-4(3H)-one
ff) 2-piperazin-1-yl-5,6,7,8-tetrahydroquinazolin-4(3H)-one
gg) 2-(Morpholin-4-yl)-7,8-dihydroquinazolin-4(3H)-one
hh) 2-(4-Benzylpiperazin-1-yl)-7,8-dihydroquinazolin-4(3H)-one
ii) 2-(4-Methylpiperazin-1-yl)-7,8-dihydroquinazolin-4(3H)-one
and the physiologically acceptable salts, derivatives, prodrugs, solvates and stereoisomers thereof, including mixtures thereof in all ratios.

Suitable salts and pharmaceutically acceptable salts of the compounds according to the invention are conventional non-toxic salts and include acid addition salts such as organic acid salts (e.g. acetate, trifluoroacetate, maleate, tartrate, methanesulfonate, benzenesulfonate, formate, toluenesulfonate), inorganic acid salt (e.g. hydrochloride, hydrobromide, hydroiodide, sulfate, nitrate, phosphate), or salts with an amino acid (e.g. arginine, aspartic acid, glutamic acid), or metal salts such as alkali metal salts (e.g. sodium salt, potassium salt) and alkaline earth metal salts (e.g. calcium salt, magnesium salt), ammonium salts, or organic base salts (e.g. trimethylamine salt, triethylamine salt, pyridine salt, picoline salt, dicyclohexylamine salt, N,N'-dibenzylethylenediamine salt).

The term "pharmaceutically usable derivatives" or "pharmaceutically acceptable derivatives" is taken to mean, for example, the salts of the compounds according to the invention and so-called prodrug compounds. The term refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

The term "prodrug derivatives" is taken to mean, for example, compounds of the present invention which have been modified, for example, with alkyl or acyl groups, sugars or oligopeptides and which are rapidly cleaved in the organism and thus release the active ingredients according to the invention. These also include biodegradable polymer derivatives of the compounds according to the invention, as described, for example, in Int. J. Pharm. 115, 61-67 (1995).

The invention also relates to mixtures of the compounds according to the invention, for example mixtures of two diastereomers, for example in the ratio 1:1, 1.2, 1:3, 1:4, 1:5, 1:10, 1:100 or 1:1000. These are particularly preferably mixtures of stereoisomeric compounds.

Additionally, the invention comprises the polymorphic forms of the compounds according to the invention, e.g. the amorphic and crystalline polymorphic forms.

As used herein, the term "solvate" preferably refers to a complex of variable stoichiometry formed by a solute and a solvent. The term solvates of the compounds is therefore taken to mean adductions of inert solvent molecules onto the compounds, which form owing to their mutual attractive force. Such solvents for the purpose of the invention may not interfere with the biological activity of the solute. Preferably the solvent used is a pharmaceutically acceptable solvent. Examples of suitable pharmaceutically acceptable solvents include, without limitation, water, ethanol and acetic acid. Most preferably the solvent used is water. Solvates are, for example, monohydrates, dihydrates or alcoholates.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, especially mixtures of enantiomers, as well as purified stereoisomers, especially purified enantiomers, or stereoisomerically enriched mixtures, especially enantiomerically enriched mixtures. Also included within the scope of the invention are the individual isomers of the compounds of the present invention as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers of the compounds of the present invention are included within the scope of the compounds of the present invention and preferably the formulae and subformulae corresponding thereto.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture.

The diastereomer resolution can also be carried out by standard purification processes, such as, for example, chromatography or fractional crystallization.

It is of course also possible to obtain optically active compounds of the present invention by the methods described above by using starting materials which are already optically active.

Unless indicated otherwise, it is to be understood that reference to the compounds of the present invention preferably includes the reference to the subformulae corresponding thereto. It is also understood that the following embodiments, including uses and compositions, although recited with respect to the compounds of the present invention are preferably also applicable to subformulae.

As used herein, the terms "group", "residue" and "radical" or "groups", "residues" and "radicals" are usually used as synonyms, respectively, as it is common practice in the art.

As used herein, the term "optionally" means that the subsequently described event(s) may or may not occur, and includes both event(s), which occur, and events that do not occur.

As used herein, the term "substituted" preferably refers to substitution with the named substituent or substituents, multiple degrees of substitution being allowed unless otherwise stated.

Subject of the present invention are especially compounds of the present invention in which one or more substituents or groups, preferably the major part of the substituents or groups has a meaning which is indicated as preferred, more preferred, even more preferred or especially preferred.

As used herein, the term "halogen" or "hal" preferably refers to fluorine (F), chlorine (Cl), bromine (Br) or iodine (I).

As used herein, the term "alkyl" or "A" preferably refers to a straight or branched chain hydrocarbon having from one to twelve carbon atoms, wherein optionally 1-5 H atoms are replaced by F and/or Cl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "cycloalkyl" preferably refers to a non-aromatic cyclic hydrocarbon ring system, with one or more rings attached to each other, each ring preferably having from three to seven carbon atoms, which optionally includes an alkyl linker, preferably a $C_1$-$C_6$ alkyl linker, through which it may be attached. Optionally, in the "cycloalkyl" 1-5 H atoms are replaced by F and/or Cl, multiple degrees of substitution being allowed. The alkyl or $C_1$-$C_6$ alkyl group is as defined above. Exemplary "cycloalkyl" groups include, but are not limited to, cyclopropyl, cyclobutyl, cyclopentyl, cyclohexyl and cycloheptyl.

As used herein, the term "aryl" or "Ar" preferably refers to an optionally substituted benzene ring or to an optionally substituted benzene ring system, in the case of $Ar^1$ optionally substituted by Hal, S-A, Ph, —O(CH$_2$)$_n$-Ph, —N(CH$_2$Ph)$_2$, in the case of $Ar^2$ optionally substituted by Hal, A, COOA, multiple degrees of substitution being allowed. Examples of "aryl" groups include, but are not limited to Phenyl, 2-naphthyl, 1-naphthyl, biphenyl, anthracyl, phenanthracyl, as well as substituted derivatives thereof.

As used herein, the term "heterocyclic" or the term "Het" preferably refers to a mono- or bicyclic, saturated, unsaturated or aromatic, three to twelve membered heterocyclic ring, which is optionally substituted by one or more substituents, selected from the group consisting of OOCA, Hal, A, $(CH_2)_nAr^2$, $(CH_2)_n$cycloalkyl, OA, $NH_2$, NHA, $NA_2$, $NO_2$, CN, COOH, COOA, $CONH_2$, CONHA, $CONA_2$, NHCOA, $NHCONH_2$, $NHCONA_2$, $NHSO_2A$, COA, $SO_2NH_2$, $SO_2NHA$, $SO_2NA_2$, $SO_2A$, $SOA_2$, $CF_3$, $OCF_3$ and $SCF_3$, with the proviso that said heterocyclic residue contains 1, 2, 3 or 4 N-, O- and/or S-atoms, at least comprising one N-atom and Het is linked via N to the pyrimidinone ring system. Examples of "heterocyclic" moieties include, but are not limited to tetrahydrofuran, pyran, 1,4-dioxane, 1,3-dioxane, pyrrolidine, piperidine, morpholine, tetrahydrothiopyran, tetrahydrothiophene, and the like.

The nomenclature as used herein for defining compounds, especially the compounds according to the invention, is in general based on the rules of the IUPAC-organisation for chemical compounds and especially organic compounds.

One of the principal mechanisms by which cellular regulation is effected is through the transduction of extracellular signals across the membrane, that in turn modulate biochemical pathways within the cell. Protein phosphorylation represents one course by which intracellular signals are propagated from molecule to molecule resulting finally in a cellular response. These signal transduction cascades are highly regulated and often overlapping, as evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88: 229-279).

Tyrosine kinases are a class of enzymes, which catalyse the transfer of the terminal phosphate of adenosine triphosphate to tyrosine residues in protein substrates. It is thought that tyrosine kinases, through substrate phosphorylation, play a crucial role in signal transduction for a number of cell functions. Although the precise mechanisms of signal transduction are still unclear, tyrosine kinases have been shown to be important contributing factors in cell proliferation, carcinogenesis and cell differentiation. Tyrosine kinases can be categorised as receptor-type tyrosine kinases or non-receptor type tyrosine kinases. Receptor-type tyrosine kinases have an extracellular portion, a transmembrane portion and an intracellular portion, while non-receptor type tyrosine kinases are exclusively intracellular.

Tyrosine kinases consist of a multiplicity of transmembrane receptors with different biological activity. Thus, about 20 different subfamilies of receptor-type tyrosine kinases have been identified. One tyrosine kinase subfamily, known as the HER subfamily, consists of EGFR, HER2, HER3 and HER4. Ligands from this subfamily of receptors include epithelial growth factor, TGF-α, amphiregulin, HB-EGF, betacellulin and heregulin. Another subfamily of these receptor-type tyrosine kinases is the insulin subfamily, which includes INS-R, IGF-IR and IR-R. The PDGF subfamily includes the PDGF-α and -β receptors, CSFIR, c-kit and FLK-II. In addition, there is the FLK family, which consists of the kinase insert domain receptor (KDR), foetal liver kinase-1 (FLK-1), foetal liver kinase-4 (FLK-4) and the fms tyrosine kinase-1 (flt-1). The PDGF and FLK families are usually discussed together due to the similarities between the two groups. For a detailed discussion of receptor-type tyrosine kinases, see Plowman et al., DN & P 7(6): 334-339, 1994, which is hereby incorporated by way of reference.

The non-receptor type tyrosine kinases likewise consist of a multiplicity of subfamilies, including Src, Frk, Btk, Csk, Abl, Zap70, Fes/Fps, Fak, Jak, Ack and LIMK. Each of these subfamilies is further sub-divided into different receptors. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor type tyrosine kinases, see Bolen Oncogene, 8: 2025-2031 (1993), which is hereby incorporated by way of reference.

Both receptor type tyrosine kinases and non-receptor type tyrosine kinases are involved in cellular signalling pathways leading to numerous pathogenic conditions, including cancer, psoriasis and hyperimmune responses. It has been proposed that various receptor-type tyrosine kinases, and the growth factors binding to them, play a role in angiogenesis, although some may promote angiogenesis indirectly (Mustonen and Alitalo, J. Cell Biol. 129: 895-898, 1995). One of these receptor-type tyrosine kinases is foetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., Oncogene 8(1): 11-15, 1993). VEGF and KDR are a ligand-receptor pair which plays a vital role in the proliferation of vascular endothelial cells and the formation and sprouting of blood vessels, referred to as vasculogenesis and angiogenesis respectively. Angiogenesis is characterised by excessive activity of vascular endothelial growth factor (VEGF). VEGF actually consists of a family of ligands (Klagsburn and D'Amore, Cytokine & Growth Factor Reviews 7: 259-270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumour growth has been shown to be susceptible to the anti-angiogenic effects of VEGF receptor antagonists (Kim et al., Nature 362, pp. 841-844, 1993).

Solid tumours can therefore be treated with tyrosine inhibitors since these tumours depend on angiogenesis for the formation of the blood vessels that are necessary to support their growth. These solid tumours include monocytic leukaemia, carcinomas of the brain, genito-urinary tract, lymphatic system, stomach, larynx and lung, including lung adenocarcinoma and small cell lung carcinoma. Further examples include carcinomas in which overexpression or activation of Raf-activating oncogenes (for example, K-Ras, Erb-B) is observed. Such carcinomas include pancreatic and breast carcinoma. Inhibitors of these tyrosine kinases are therefore suitable for the prevention and treatment of proliferative diseases caused by these enzymes. The angiogenic activity of VEGF is not limited to tumours. VEGF accounts for the angiogenic activity produced in or near the retina in diabetic retinopathy. This vascular growth in the retina leads to visual degeneration culminating in blindness. Ocular VEGF mRNA and protein levels are elevated by conditions such as retinal vein occlusion in primates and decreased $pO_2$ levels in mice that lead to neovascularisation. Intraocular injections of anti-VEGF monoclonal antibodies or VEGF receptor immunofusions inhibit ocular neovascularisation in both primate and rodent models. Irrespective of the cause of induction of VEGF in human diabetic retinopathy, inhibition of ocular VEGF is suitable for treating this disease.

Expression of VEGF is also significantly increased in hypoxic regions of animal and human tumours adjacent to areas of necrosis. In addition, VEGF is upregulated by the expression of the oncogenes Ras, Raf, Src and mutant p53 (all of which are relevant in combating cancer). Anti-VEGF monoclonal antibodies inhibit the growth of human tumours in nude mice. Although the same tumour cells continue to express VEGF in culture, the antibodies do not diminish their mitotic rate. Thus, tumour-derived VEGF does not function as an autocrine mitogenic factor. VEGF therefore contributes to tumour growth in vivo by promoting angiogenesis through its paracrine vascular endothelial cell chemotactic and mitogenic activities. These monoclonal antibodies also inhibit the growth of typically less well vascularised human colon carcinomas in athymic mice and decrease the number of tumours arising from inoculated cells.

The expression of a VEGF-binding construct of Flk-1, Flt-1, the mouse KDR receptor homologue truncated to eliminate the cytoplasmic tyrosine kinase domains but retaining a membrane anchor, virtually stops the growth of a transplantable glioblastoma in mice, presumably by the dominant negative mechanism of heterodimer formation with membrane-spanning endothelial cell VEGF receptors.

Embryonic stem cells, which normally grow as solid tumours in nude mice, do not produce detectable tumours if both VEGF alleles are knocked out. Taken together, these data indicate the role of VEGF in the growth of solid tumours. Inhibition of KDR or Flt-1 is involved in pathological angiogenesis, and these receptors are suitable for the treatment of diseases in which angiogenesis is part of the overall pathology, for example inflammation, diabetic retinal vascularisation, as well as various forms of cancer, since tumour growth is known to be dependent on angiogenesis (Weidner et al., N. Engl. J. Med., 324, pp. 1-8, 1991).

Angiopoietin 1 (Ang1), a ligand for the endothelium-specific receptor-type tyrosine kinase TIE-2, is a novel angiogenic factor (Davis et al., Cell, 1996, 87: 1161-1169; Partanen et al., Mol. Cell. Biol., 12: 1698-1707 (1992); U.S. Pat. Nos. 5,521,073; 5,879,672; 5,877,020; and 6,030,831). The acronym TIE stands for "tyrosine kinase with Ig and EGF homology domains". TIE is used for the identification of a class of receptor-type tyrosine kinases, which are expressed exclusively in vascular endothelial cells and early haemopoietic cells. TIE receptor kinases are typically characterised by the presence of an EGF-like domain and an immunoglobulin (Ig)-like domain, which consists of extracellular fold units stabilised by disulfide bridge bonds between the chains (Partanen et al. Curr. Topics Microbiol. Immunol., 1999, 237: 159-172). In contrast to VEGF, which exerts its function during the early stages of vascular development, Ang1 and its receptor TIE-2 act during the later stages of vascular development, i.e. during vascular transformation (transformation relates to the formation of a vascular lumen) and maturing (Yancopoulos et al., Cell, 1998, 93:661-664; Peters, K. G., Circ. Res., 1998, 83(3): 342-3; Suri et al., Cell 87, 1171-1180 (1996)).

Accordingly, it would be expected that inhibition of TIE-2 should interrupt the transformation and maturing of a new vascular system initiated by angiogenesis and should thus interrupt the angiogenesis process. Furthermore, inhibition at the kinase domain-binding site of VEGFR-2 would block phosphorylation of tyrosine residues and serve to interrupt initiation of angiogenesis. It must therefore be assumed that inhibition of TIE-2 and/or VEGFR-2 should prevent tumour angiogenesis and serve to slow or completely eliminate tumour growth. Accordingly, treatment of cancer and other diseases associated with inappropriate angiogenesis could be provided.

The present invention relates to methods for the regulation, modulation or inhibition of TIE-2 for the prevention and/or treatment of diseases associated with unregulated or disturbed TIE-2 activity. In particular, the compounds according to the invention can also be employed in the treatment of certain forms of cancer. Furthermore, the compounds according to the invention can be used to provide additive or synergistic effects in certain existing cancer chemotherapies and/or can be used to restore the efficacy of certain existing cancer chemotherapies and radiotherapies.

The present invention furthermore relates to the compounds as inhibitors of Raf kinases. Protein phosphorylation is a fundamental process for the regulation of cellular functions. The coordinated action of both protein kinases and phosphatases controls the degrees of phosphorylation and, hence, the activity of specific target proteins. One of the predominant roles of protein phosphorylation is in signal transduction, where extracellular signals are amplified and propagated by a cascade of protein phosphorylation and dephosphorylation events, for example in the $p21^{ras}$/Raf pathway.

The $p21^{ras}$ gene was discovered as an oncogene of the Harvey (H-Ras) and Kirsten (K-Ras) rat sarcoma viruses. In humans, characteristic mutations in the cellular Ras gene (c-Ras) have been associated with many different types of cancers. These mutant alleles, which render Ras constitutively active, have been shown to transform cells, such, for example, as the murine cell line NIH 3T3, in culture.

The $p21^{ras}$ oncogene is a major contributor to the development and progression of human solid carcinomas and is mutated in 30% of all human carcinomas (Bolton et al. (1994) Ann. Rep. Med. Chem., 29, 165-74; Bos. (1989) Cancer Res., 49: 4682-9). In its normal, unmutated form, the Ras protein is a key element of the signal transduction cascade directed by growth factor receptors in almost all tissues (Avruch et al. (1994) Trends Biochem. Sci., 19: 279-83).

Biochemically, Ras is a guanine nucleotide binding protein and cycling between a GTP-bound activated and a GDP-bound resting form is strictly controlled by Ras endogenous GTPase activity and other regulatory proteins. The Ras gene product binds to guanine triphosphate (GTP) and guanine diphosphate (GDP) and hydrolyses GTP to GDP. Ras is active in the GTP-bound state. In the Ras mutants in cancer cells, the endogenous GTPase activity is reduced and the protein consequently transmits constitutive growth signals to downstream effectors, such as, for example, the enzyme Raf kinase. This leads to the cancerous growth of the cells, which carry these mutants (Magnuson et al. (1994) Semin. Cancer Biol., 5, 247-53). The Ras proto-oncogene requires a functionally intact c-Raf-1 proto-oncogene in order to transduce growth and differentiation signals initiated by receptor and non-receptor-type tyrosine kinases in higher eukaryotes.

Activated Ras is necessary for the activation of the c-Raf-1 proto-oncogene, but the biochemical steps through which Ras activates the Raf-1 protein (Ser/Thr) kinase are now well characterised. It has been shown that inhibiting the effect of active Ras by inhibiting the Raf kinase signalling pathway by administration of deactivating antibodies to Raf kinase or by co-expression of dominant negative Raf kinase or dominant negative MEK (MAPKK), the substrate of Raf kinase, leads to reversion of transformed cells to the normal growth phenotype (see: Daum et al. (1994) Trends Biochem. Sci., 19, 474-80; Fridman et al. (1994) J. Biol. Chem., 269, 30105-8. Kolch et al. (1991) Nature, 349, 426-28 and for a review Weinstein-Oppenheimer et al. Pharm. & Therap. (2000), 88, 229-279).

Similarly, inhibition of Raf kinase (by antisense oligodeoxynucleotides) has been correlated in vitro and in vivo with inhibition of the growth of a variety of human tumour types (Monia et al., Nat. Med. 1996, 2, 668-75).

Raf serine- and threonine-specific protein kinases are cytosolic enzymes that stimulate cell growth in a variety of cell systems (Rapp, U. R., et al. (1988) in The Oncogene Handbook; T. Curran, E. P. Reddy and A. Skalka (eds.) Elsevier Science Publishers; The Netherlands, pp. 213-253; Rapp, U. R., et al. (1988) Cold Spring Harbor Sym. Quant. Biol. 53: 173-184; Rapp, U. R., et al. (1990) Inv Curr. Top. Microbiol. Immunol. Potter and Melchers (eds.), Berlin, Springer-Verlag 166: 129-139).

Three isozymes have been characterised: C-Raf (Raf-1) (Bonner, T. I., et al. (1986) Nucleic Acids Res. 14: 1009-1015). A-Raf (Beck, T. W., et al. (1987) Nucleic Acids Res. 15: 595-609) and B-Raf (Qkawa, S., et al. (1998) Mol. Cell. Biol. 8: 2651-2654; Sithanandam, G. et al. (1990) Oncogene: 1775). These enzymes differ in their expression in various tissues. Raf-1 is expressed in all organs and in all cell lines that have been examined, and A- and B-Raf are expressed in urogenital and brain tissues respectively (Storm, S. M. (1990) Oncogene 5: 345-351).

Raf genes are proto-oncogenes: they can initiate malignant transformation of cells when expressed in specifically altered forms. Genetic changes that lead to oncogenic activation generate a constitutively active protein kinase by removal of or interference with an N-terminal negative regulatory domain of the protein (Heidecker, G., et al. (1990) Mol. Cell. Biol. 10: 2503-2512; Rapp, U. R., et al. (1987) in Oncogenes and Cancer; S. A. Aaronson, J. Bishop, T. Sugimura, M. Terada, K. Toyoshima and P. K. Vogt (eds.) Japan Scientific Press, Tokyo). Microinjection into NIH 3T3 cells of oncogenically activated, but not wild-type, versions of the Raf protein prepared with *Escherichia coli* expression vectors results in morphological transformation and stimulates DNA synthesis (Rapp, U. R., et al. (1987) in Oncogenes and Cancer; S. A. Aaronson, J. Bishop, T. Sugimura, M. Terada, K. Toyoshima and P. K. Vogt (ed.) Japan Scientific Press, Tokyo; Smith, M. R., et al. (1990) Mol. Cell. Biol. 10: 3828-3833).

Consequently, activated Raf-1 is an intracellular activator of cell growth. Raf-1 protein serine kinase is a candidate for the downstream effector of mitogen signal transduction, since Raf oncogenes overcome growth arrest resulting from a block of cellular Ras activity due either to a cellular mutation (Ras revertant cells) or microinjection of anti-Ras antibodies (Rapp, U. R., et al. (1988) in The Oncogene Handbook, T. Curran, E. P. Reddy and A. Skalka (ed.), Elsevier Science Publishers; The Netherlands, pp. 213-253; Smith, M. R., et al. (1986) Nature (London) 320: 540-543).

C-Raf function is required for transformation by a variety of membrane-bound oncogenes and for growth stimulation by mitogens contained in serums (Smith, M. R., et al. (1986) Nature (London) 320: 540-543). Raf-1 protein serine kinase activity is regulated by mitogens via phosphorylation (Morrison, D. K., et al. (1989) Cell 58: 648-657), which also effects sub-cellular distribution (Olah, Z., et al. (1991) Exp. Brain Res. 84: 403; Rapp, U. R., et al. (1988) Cold Spring Harbor Sym. Quant. Biol. 53: 173-184. Raf-1 activating growth factors include platelet-derived growth factor (PDGF) (Morrison, D. K., et al. (1988) Proc. Natl. Acad. Sci. USA 85: 8855-8859), colony-stimulating factor (Baccarini, M., et al. (1990) EMBO J. 9: 3649-3657), insulin (Blackshear, P. J., et al. (1990) J. Biol. Chem. 265: 12115-12118), epidermal growth factor (EGF) (Morrison, R. K., et al. (1988) Proc. Natl. Acad. Sci. USA 85: 8855-8859), interleukin-2 (Turner, B. C., et al. (1991) Proc. Natl. Acad. Sci. USA 88:1227) and interleukin-3 and granulocyte macrophage colony-stimulating factor (Carroll, M. P., et al. (1990) J. Biol. Chem. 265: 19812-19817).

After mitogen treatment of cells, the transiently activated Raf-1 protein serine kinase translocates to the perinuclear area and the nucleus (Olah, Z., et al. (1991) Exp. Brain Res. 84: 403; Rapp, U. R., et al. (1988) Cold Spring Harbor Sym. Quant. Biol. 53: 173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374) and Raf oncogenes activate transcription from Ap-I/PEA3-dependent promoters in transient transfection assays (Jamal, S., et al. (1990) Science 344: 463-466; Kaibuchi, K., et al. (1989) J. Biol. Chem. 264: 20855-20858; Wasylyk, C., et al. (1989) Mol. Cell. Biol. 9: 2247-2250).

There are at least two independent pathways for Raf-1 activation by extracellular mitogens: one involving protein kinase C (KC) and a second initiated by protein tyrosine kinases (Blackshear, P. J., et al. (1990) J. Biol. Chem. 265: 12131-12134; Kovacina, K. S., et al. (1990) J. Biol. Chem. 265: 12115-12118; Morrison, D. K., et al. (1988) Proc. Natl. Acad. Sci. USA 85: 8855-8859; Siegel, J. N., et al. (1990) J. Biol. Chem. 265: 18472-18480; Turner, B. C., et al. (1991) Proc. Natl. Acad. Sci. USA 88: 1227). In each case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233: 305-312).

The protein kinase PKB (also known as AKT and RAC-PK) is a member of the AKT/PKB family of serine/threonine kinases and has been shown to be involved in a diverse set of signalling pathways in human malignancy (Nicholson et al., Cell. Signal., 2002, 14, 381-395). PKB, like other members of the AKT/PKB family, is located in the cytosol of unstimulated cells and translocates to the cell membrane following stimulation. PKB translocation can be activated by a number of ligands, including platelet derived growth factor, epidermal growth factor, basic fibroblast growth factor, cellular stress, such as, for example, heat shock and hyperosmolarity, as well as insulin (Bos, Trends Biochem. Sci., 1995, 20, 441-442), and other studies have shown that this activation is through PI3 kinase which is wortmannin sensitive (Franke et al., Science, 1997, 275, 665-668). Once localised to the plasma membrane, PKB has been shown to mediate several functions within the cell, including apoptosis, the metabolic effects of insulin, induction of differentiation and/or proliferation, protein synthesis and stress responses (Alessi and Cohen, Curr. Opin. Genet. Dev., 1998, 8: 55-62; Downward, Curr. Opin. Cell Biol., 1998, 10, 262-267).

PKB was cloned independently in 1991 by three groups (Bellacosa et al., Science, 1991, 254, 274-277; Coffer and Woodgett, Eur. J. Biochem., 1991, 201, 475-481; Jones et al., Cell Regul., 1991, 2, 1001-1009), but its association with primary human gastric carcinoma was recognised as early as 1987 (Staal et al., Proc. Natl. Acad. Sci. USA, 1987, 84, 5034-5037). Sequencing of PKBα revealed homology within the kinase domains to the PKA (about 68%) and PKC isozymes (about 73%) (Jones et al., Proc. Natl. Acad. Sci. U.S.A., 1991, 88, 4171-5), a fact that lead to its renaming as PKB. There are three cellular isoforms of PKB and two splice variants (PKBα, β, γ, β$_1$, γ$_1$; Brazil et al. Trends in Bio Sci, 2001, 26, 657-663). PKBα was found to be amplified or overexpressed in gastric adenocarcinomas and in a breast cancer cell line (Staal et al., Proc. Natl. Acad. Sci. U.S.A., 1987, 84, 5034-7; Jones et al., Cell Regul., 1991, 2, 1001-9). PKBβ is amplified or overexpressed in 3% of breast (Bellacosa et al., Int. J. Cancer, 1995 64, 280-5), 12% of pancreatic (Cheng et al., Proc. Natl. Acad. Sci. U.S.A., 1996, 93, 3636-41) and 15% of ovarian cancers (Bellacosa et al., Int. J. Cancer, 1995, 64, 280-5; Cheng et al., Proc. Natl. Acad. Sci. U.S.A., 1992, 89, 9267-71).

PKBγ is overexpressed in oestrogen receptor-deficient breast cancer and in androgen-independent prostate cell lines (Nakatani et al., J. Biol. Chem. 1999, 274, 21528-32).

It has been proposed that PKB is a gene, which is involved in chromosomal rearrangement at chromosome band 14q32. This locus is known to undergo rearrangement in human T-cell malignancies, such as, for example, prolymphocytic leukaemias and mixed lineage childhood leukaemias (Staal et al., Genomics, 1988, 2, 96-98).

PKB also plays a role in the prevention of "programmed cell death" or apoptosis by inhibitory phosphorylation of ASK-1, Bad, Caspase9 and FKHR (for review see Nicholson et al., Cell Signalling 2001, 14, 281-395). It has been shown that PKB provides a survival signal (for review see Lawlor et al., J. of Cell Science 2001, 114, 2903-2910) to cells in order to protect them from a number of agents, including UV radiation (Dudek et al., Science, 1997, 275, 661-665), withdrawal of IGF1 from neuronal cells, detachment from the extracellular matrix, stress and heat shock (Alessi and Cohen, Curr. Opin. Genet. Dev., 1998, 8: 55-62).

The dual-specific phosphatase PTEN (phosphatase and tensin homologue deleted on chromosome ten) increases the PtdIns(3, 4, 5)P$_3$ level in the cell by dephosphorylation of PtdIns(3, 4, 5)P$_3$. PtdIns(3, 4, 5)P$_3$ binds to the PH domain (Pleckstrin homology domain) of PKB. This binding is an essential step for membrane translocation and activation of PKB. PTEN is a tumour suppressor gene mutated in a large proportion of glioblastoma and melanoma cell lines, advanced prostate carcinomas and endometrial carcinomas. Furthermore, it is deleted in >80% of patients with hereditary conditions, such as, for example, Cowden's disease, Lhermitte-Duclose disease and Bannayan-Zonana Syndrome. The patients display a number of similar features, including multiple benign tumours (harmatomas) and increased susceptibility to breast and thyroid malignancies (Di Cristofano et al. Cell, 2000, 100, 387-390).

Cell lines derived from PTEN$^{+/-}$ heterozygous mice (PTEN$^{-/-}$ heterozygous mice are not viable) show increased PtdIns(3, 4, 5)P$_3$ levels paralleled by increased PKB activity, with concomitant decreased sensitivity to apoptosis (Di Christofano et al. Nat. Genet. 1998, 19, 348-355; Stambolic et al., Cell, 1998, 95, 29-39, Myers et al., Proc. Natl. Acad. Si. U.S.A., 1998, 96: 13513-13518).

PKB is also able to promote cell cycle progression by inhibiting p21 cell cycle inhibitor (Zhou et al.; Nat. Cell Biol., 2002, 3: 245-252).

These findings may explain the overexpression of PKB observed in cancer cells, which allows preferential survival and proliferation of the carcinomas by avoiding the normal progression to apoptosis.

At present, there are no known therapeutic agents, which effectively inhibit the activity of PKB. Consequently, there remains a long felt need for additional agents, which are capable of effectively inhibiting PKB function for the activation of pro-apoptotic proteins in all kinds of cancer as chemotherapeutic agents.

The identification of small compounds, which specifically inhibit, regulate and/or modulate signal transduction of protein kinases and can be used as medicaments for the treatment of various diseases is therefore desirable and an aim of the present invention.

Thus, a further preferred embodiment of the present invention is the use of a compound of the formula I for the preparation of a medicament for the treatment and/or prevention of disorders.

A further preferred embodiment of the present invention is the use of a compound of the formula I for the manufacture of a medicament for the treatment and/or prevention of disorders, which are caused, mediated and/or propagated by protein kinases.

Usually, the disorders discussed herein are divided into two groups, hyperproliferative and non-hyperproliferative disorders. In this context, infection or infectious diseases, psoriasis, arthritis, inflammation, endometriosis, scarring, benign prostatic hyperplasia, immunological diseases, autoimmune diseases and immunodeficiency diseases are to be regarded as non-cancerous disorders, of which infection, arthritis, inflammation, immunological diseases, autoimmune diseases and immunodeficiency diseases are usually regarded as non-hyperproliferative disorders. In this context, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia are to be regarded as cancerous disorders, all of which are usually regarded as hyperproliferative disorders.

Thus, a preferred embodiment of the present invention is the use of a compound of the formula I for the preparation of a medicament for the treatment and/or prevention of disorders, characterized in that the disorders are selected from the group consisting of hyperproliferative and non-hyperproliferative disorders.

In a preferred embodiment of the present invention the disorder is non-cancerous.

Therefore, the compounds of the formula I can be used for the preparation of a medicament for the treatment and/or prevention of disorders, which are selected from the group consisting of psoriasis, arthritis, rheumatoid arthritis, inflammation, endometriosis, scarring, infections, *Helicobacter pylori* infection, Influenza A infection, benign prostatic hyperplasia, immunodeficiency diseases, autoimmune disease, immunological diseases, chronic obstructive pulmonary disease, asthma, inflammatory bowel disease, fibrosis, atherosclerosis, restenosis, vascular disease, cardiovascular disease, renal disease and angiogenesis disorders, mesangial cell proliferative disorders, diabetic nephropathy, diabetic retinopathy, malignant nephrosclerosis, thrombotic microangiopathy syndromes, organ transplant rejection, glomerulopathies, metabolic disorders and neurodegenerative diseases.

Infections according the invention include, but are not limited to infections caused by pathogenic microorganisms, such as bacteria, fungi, viruses and protozoans, for example influenza (Pleschka, S. et al. Nature Cell Biol. 2001, 3, page 301-305), retroviruses, for example HIV infection (Yang, X. et al. J. Biol. Chem. 1999, 274, page 27981-27988; Popik, W et al Mol Cel Biol. 1996, 16, page 6532-6541), Hepatitis B (Benn, J et al., Proc. Natl. Acad. Sci. 1995, 92, page 11215-11219), Hepatitis C (Aoki et al. J. Virol. 2000, 74, page 1736-1741), papillomavirus, parainfluenza, rhinoviruses, adenoviruses, *Heliobacter pylori*, and viral and bacterial infections of the skin (e.g. cold sores, warts, chickenpox, molluscum. contagiosum, herpes zoster, boils, cellulitis, erysipelas, impetigo, tinea, Althlete's foot and ringworm).

Furthermore, a preferred embodiment of the present invention is the use of a compound of the formula I for the manufacture of a medicament for the treatment and/or prevention of disorders, characterized in that the disorders are selected from the group consisting of hyperproliferative disorders.

There are many disorders associated with a dysregulation of cellular proliferation. The conditions of interest include, but are not limited to, the following conditions. The subject compounds are useful in the treatment of a variety of conditions where there is proliferation and/or migration of smooth muscle cells, and/or inflammatory cells into the intimal layer of a vessel, resulting in restricted blood flow through that vessel, e.g., neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Furthermore, the compounds of the formula I preferably show anti-angiogenic properties. Thus, compounds of the present invention can be advantageously employed in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, organ transplant rejection and glomerulopathies; and metabolic disorders include psoriasis, diabetes mellitus, chronic wound healing, inflammation and neurodegenerative diseases.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravasation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels.

Normal angiogenesis is activated during tissue growth, from embryonic development through maturity, and then enters a period of relative quiescence during adulthood.

Normal angiogenesis is also activated during wound healing, and at certain stages of the female reproductive cycle. Inappropriate or pathological angiogenesis has been associated with several disease states including various retinopathies; ischemic disease; atherosclerosis; chronic inflammatory disorders; rheumatoid arthritis, and cancer. The role of angiogenesis in disease states is discussed, for instance, in Fan et al., Trends in Pharmacol Sci. 16:54 66; Shawver et al., DOT Vol. 2, No. 2 Feb. 1997; Folkmann, 1995, Nature Medicine 1:27-31.

In cancer the growth of solid tumors has been shown to be angiogenesis dependent. (see Folkmann, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Several protein kinases are involved in angiogenic processes. Endothelial growth factors (e.g. vascular endothelial growth factor VEGF) activate receptor tyrosine kinases (e.g. VEGFR-2) and signal through the Ras/Raf/Mek/Erk kinase cascade. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, April 2000).

Mice with a targeted disruption in the B-raf gene die of vascular defects during development (Wojnowski, L. et al. 1997, Nature genetics 16, page 293-296). These mice show defects in the formation of the vascular system and in angiogenesis e.g. enlarged blood vessels and increased apoptotic death of differentiated endothelial cells.

Diseases where there is hyperproliferation and tissue remodelling or repair or reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature.

A preferred embodiment of the present invention is the use of a compound of the formula I for the manufacture of a medicament for the treatment and/or prevention of disorders, characterized in that the disorder is cancer.

Therefore, a preferred embodiment of the present invention is the use of a compound of the general formula I for the manufacture of a medicament for the treatment and/or prevention of disorders, characterised in that the disorders are selected from the group consisting of carcinomas, e.g. melanoma, brain cancer, lung cancer, non-small cell lung carcinoma, transitional and squamous cell urinary carcinoma, bladder cancer, gastric cancer, pancreatic cancer, colon cancer, duodenal cancer, ductal cancer, endometrial cancer, stomach cancer, colorectal cancer, hepatic cancer, renal cancer, breast cancer, head cancer, neck cancer, oesophageal cancer, gynaecological cancer, ovarian cancer, uterine cancer, prostate cancer, thyroid cancer, dysplastic oral mucosa, polyposis, invasive oral cancer, etc.; neurological malignancies; e.g. neuroblastoma, gliomas, etc; hematological malignancies, e.g., childhood acute leukaemia, non-Hodgkin's lymphomas, chronic lymphocytic leukaemia, malignant cutaneous T-cells, mycosis fungoides, non-MF cutaneous T-cell-lymphoma, lymphomatoid papulosis, T-cell rich cutaneous lymphoid hyperplasia, bullous pemphigoid, discoid lupus erythematosus, lichen planus, etc.; and the like.

Tumors of neural tissue are of particular interest, e.g., gliomas, neuromas, etc. Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltration (or invasive) ductal carcinoma (IDC) has metastasized through the wall of the duct and invaded the fatty tissue of the breast. Infiltrating (or invasive) lobular carcinoma (ILC) is similar to IDC, in that it has the potential to metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease, clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue, remodeling and repair. For example, the chronic skin inflammation of psoriasis is associated with hyperplastic epidermal keratinocycles as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemia's and lymphomas. Symptoms of allergies to environmental and food agents, as well as inflammatory bowel disease, may also be alleviated by the compounds of the invention.

For use in the subject methods, the subject compounds may be formulated with pharmaceutically active agents other than the compounds according to the invention, particularly other anti-metastatic, antitumor or anti-angiogenic agents. Angiostatic compounds of interest include angiostatin, enclostatin, carboxy terminal peptides of collagen alpha (XV), etc. Cytotoxic and cytostatic agents of interest include adriamycin, aleran, Ara-C, BICNU, busulfan, CNNU, cisplatinum, cytoxan, daunorubicin, DTIC, 5-FU, hydrea, ifosfamicle, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc. For example, in the case of bone conditions, combinations that would be favourable include those with antiresorptive bisphosphonates, such as alendronate and risedronate; integrin blockers (as defined further below), such as $\alpha_v\beta_3$ antagonists; conjugated oestrogens used in hormone replacement therapy, such as PREMPRO®, PREMARIN® and ENDOMETRION®; selective oestrogen receptor modulators (SERMs), such as raloxifene, droloxifene, CP-336,156 (Pfizer) and lasofoxifene; cathepsin K inhibitors; and ATP proton pump inhibitors.

The present compounds are also suitable for combination with known anti-cancer agents. These known anti-cancer agents include the following: oestrogen receptor modulators androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibiting VEGF in combination with radiotherapy have been described in the art (see WO00/61186).

Therefore, a preferred embodiment of the present invention is the use of a compound of the general formula I for the manufacture of a medicament for the treatment and/or prevention of disorders, characterized in that a therapeutically effective amount of one or more compounds according to the present invention is administered in combination with an compound selected from the group consisting of estrogen receptor modulators, androgen receptor modulators, retinoid receptor modulators, cytotoxic agents, anti-proliferative agents, prenyl protein protease inhibitors, HMG CoA reductase inhibitors, HIV protease inhibitors, reverse transcriptase inhibitors, growth factor receptor inhibitors and angiogenesis inhibitors.

Additionally, a preferred embodiment of the present invention is the use of a compound of the general formula I for the manufacture of a medicament for the treatment and/or prevention of disorders, characterized in that a therapeutically effective amount of one or more compounds according to the present invention is administered in combination radio therapy and with an compound selected from the group consisting of estrogen receptor modulators, androgen receptor modulators, retinoid receptor modulators, cytotoxic agents, anti-proliferative agents, prenyl protein protease inhibitors, HMG CoA reductase inhibitors, HIV protease inhibitors, reverse transcriptase inhibitors, growth factor receptor inhibitors and angiogenesis inhibitors.

"Oestrogen receptor modulators" refers to compounds, which interfere with or inhibit the binding of oestrogen to the receptor, regardless of mechanism. Examples of oestrogen receptor modulators include, for example, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl] phenyl-2,2-dimethylpropanoate, 4,4'-dihydroxybenzophenone-2,4-dinitrophenylhydrazone and SH646. "Androgen receptor modulators" refers to compounds, which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds, which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl retinamide.

"Cytotoxic agents" refers to compounds, which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine) platinum, benzylguanine, glufosfamide, GPX100, (trans,trans,trans)-bis-mu-(hexane-1,6-diamine)-mu-[diamine-platinum(II)]bis[diamine(chloro)platinum (II)]tetrachloride, diarizidinyl-spermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxy-caminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)-camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]-amino]-3-hydroxy-7H-indeno[2,1-c]quinolin-7-one and dimensa.

"Antiproliferative agents" include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluorom-ethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diaza-tetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab and tumour suppressor genes, such as p53, which can be delivered via recombinant virus-mediated gene transfer (see U.S. Pat. No. 6,069,134, for example).

Surprisingly, the problem to prepare such tetra- and dihydroquinazolinone derivatives, was solved by choosing phenyl vinyl sulfone (R. V. C. Carr, L. Paquette, J. Amer. Chem. Soc. 1980, 102, 853-855; R. V. C. Carr, R. V. Williams, L. Paquette, J. Org. Chem. 1983, 48, 4976-4986) as a dienophile, which undergoes regioselective Diels-Alder reaction and gives adducts suitable for further derivatization. Although this sulfone has been used as a dienophile in an intramolecular Diels-Alder reaction with cyclobutene ring (E. J. Bush, D. W. Jones, J. Chem. Soc., Perkin Trans. 1, 1997, 3531-3536; E. J. Bush, D. W. Jones, T. P. Mark, Tett. Lett. 1994, 35, 9755-9758; T. Kametani, Y. Suzuki, T. Honda, Chem. Pharma. Bull. 1986, 34, 4971-4977), a regioselective intermolecular addition to cyclobutene ring has never been achieved.

Therefore, the present invention relates to the synthesis of 2-aryl, 2-amino and 2-aryl-6-alkyl substituted tetra- and dihydroquinazolinones by a regioselective addition of phenyl vinyl sulfone to cyclobutene annelated pyrimidinones and subsequent alkylation at CH(SO$_2$Ph) followed by reductive elimination of sulfonyl group.

Under basic conditions (Et$_3$N, dioxane) amidines (see formula 2) cleanly undergo Michael addition to methyl 2-chloro-2-cyclopropylideneacetate (see formula 1), followed by cyclopropyl ring-opening reaction to afford cyclobutene annelated pyrimidinones (see formula 3) in 68-83% yields. Thermal ring opening reaction of the later at 175° C. followed by regioselective Diels-Alder cycloaddition with phenyl vinyl sulfone gives 2-aryl-6-(phenylsulfonyl)-5,6,7,8-tetrahydroquinazolinone derivatives (see formula 5) in 43-83% yields. Basic elimination of sulfonyl group and subsequent hydrogenation lead to 2-aryltetrahydroquinazolinone derivatives (see formula 7) in excellent yields. Deprotonation at sulfone centre, alkylation and elimination of sulfone group followed by hydrogenation give 2,6-disubstituted tetrahydroquinazolinones (see formulae 10 a-b). Nucleophilic substitution of SMe group in formula 3g by secondary amines yields 2-aminotetrahydroquinazolinones (see formula 14 a-c).

In conclusion, cyclobutene annelated pyrimidinones (see formulae 3a-g) prepared by Michael addition of amidines to methyl 2-chloro-2-cyclopropylidineacetate (see formula I) undergo thermal ring opening and regioselective Diels-Alder reaction with phenyl vinyl sulfone. We have successfully removed the sulfone group via a two-step procedure of basic elimination of PhSO$_2$H and hydrogenation reactions. We have developed a method of transforming aromatic nitriles to 2-aryl-6-alkyl-tetrahydroquinazolinone derivatives (see formulae 10a-b) in 5 simple steps in good overall yields using 5-carbon-cyclopropyl building block-methyl 2-chloro-2-cyclopro-pylidineacetate (see formula I).

propylidineacetate (see formula 1) with excess of amidines according to formula 2 in the presence of an organic amine base. Solvents are preferentially ether, tetrahydrofuran, 1,4-dioxane, bases used are preferentially diisopropyldiethylamine, triethylamine, temperature preferentially is room temperature.

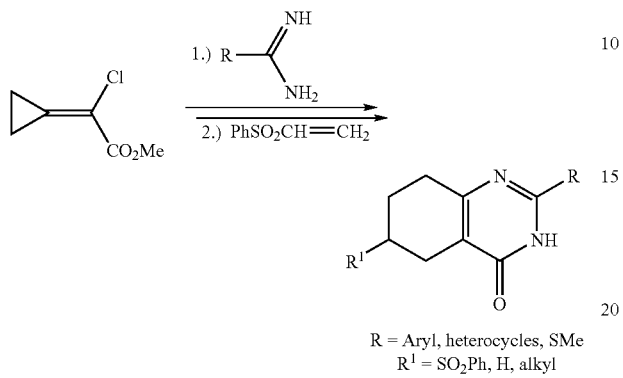

R = Aryl, heterocycles, SMe
R$^1$ = SO$_2$Ph, H, alkyl

Therefore, a preferred embodiment of the present invention is a method for the manufacture of a compound according to formula I,
a) wherein ----- is a single bond, characterized in that a compound of the formula II,

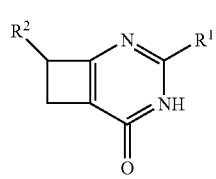

wherein R$^1$ and R$^2$ are as defined above, is reacted with a compound of the formula III,

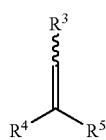

wherein R$^3$, R$^4$ and R$^5$ are as defined above, or
b) wherein ----- is a double bond, characterized in that R$^4$—H is eliminated from a compound formula I, wherein R$^4$ is SO$_2$Ar$^2$ and ----- is a single bond, or
c) wherein ----- is a single bond, characterized in that in a compound of the formula I, wherein ----- is a double bond, said double bond is transferred to a single bond by hydration, or
d) characterized in that a residue R$^1$, R$^2$, R$^3$, R$^4$ and/or R$^5$, as defined in formula I, is converted in another residue R$^1$, R$^2$, R$^3$, R$^4$ and/or R$^5$, by e.g.
  i. introducing an alkyl group,
  ii. converting a S-A residue in a Het residue, or
characterized in that a compound of formula I is isolated and/or treated with an acid or a base, to obtain the salt thereof.

In a first step a compound according to formula 3 is obtained by stirring a solution of methyl 2-chloro-2-cyclo-

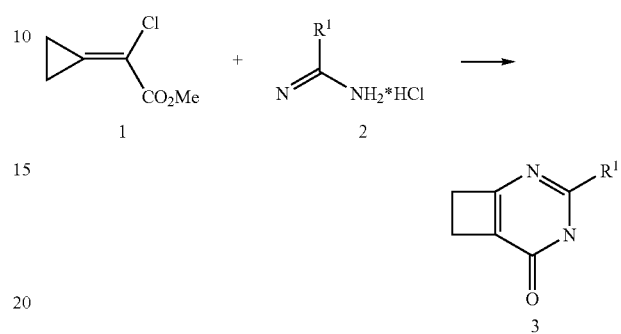

Then, compounds of the formula 5 are obtained by stirring a compound of formula 3 with excess of a compound of formula 4 (e.g. phenylsulfone) in a sealed tube at temperatures between 100° C. and 220° C.

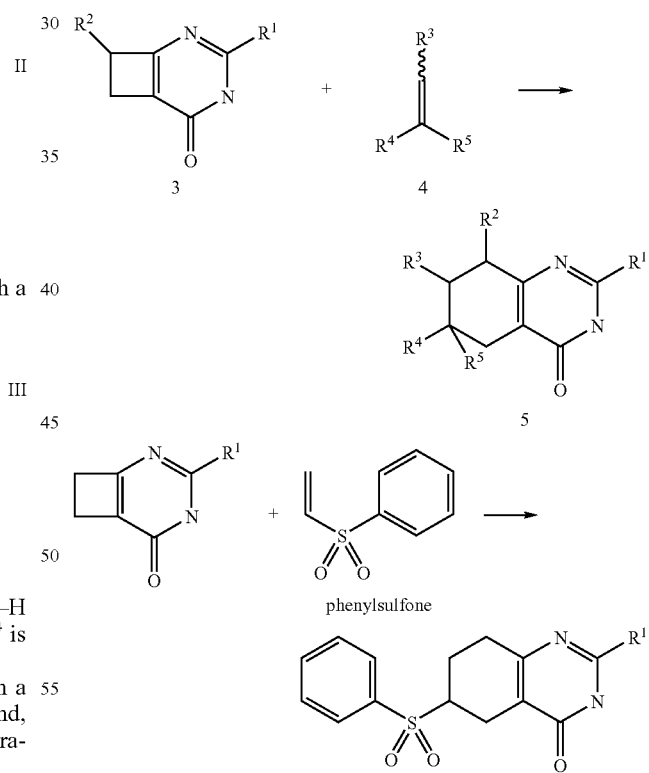

A compound according to formula 6 is obtained by adding an excess of organic base like DBU or potassium-tert.-butylate to a suspension of a sulfone according to formula 5 in an appropriate solvent and stirring the resulting solution at ambient temperature, The solvent is chosen from chloroform, dichloromethane, hexane, tetrahydrofuran or dioxane, preferentially tetrahydrofuran or dichloromethane.

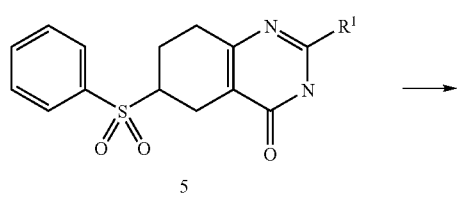

5

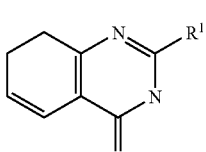

6

A compound according to formula 6 can be transformed to compound according to formula 7 by treatment with gaseous hydrogen under anhydrous conditions in solvents like methanol, ethanol, isopropanol, butanol, dichloromethane, chloroform, tetrahydrofuran or dioxane using heterogenous catalysis like palladium or platinum fixed on a solid support like alumina or charcoal, which is removed after completion of the reaction by filtration through a pad of Celite.

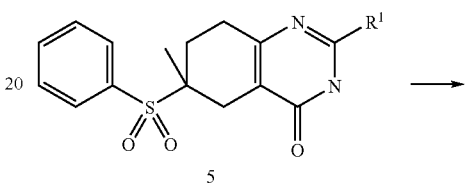

A compound of formula 9 is obtained via the protected derivative 5a-TMS, which is obtained by standard methods described in literature (trimethylsilyl, TMS shown as example for a suitable protecting group). 5a-TMS is treated with butyl-lithium in tetrahydrofuran at temperatures between −78° C. and −15° C. An alkylation reagent, e.g. iodomethane is added in slight excess and temperature slowly adjusted to room temperature during a period of 4-15 hours.

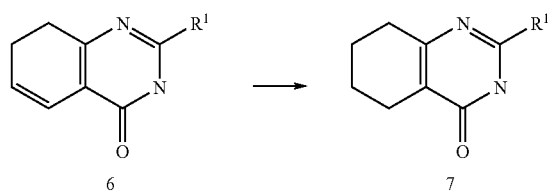

Compounds according to formula 11 are obtained in analogy to compounds according to formula 6. Compound according to formula 10 are obtained in analogy to according to formula 7.

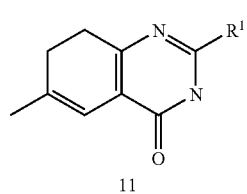

5

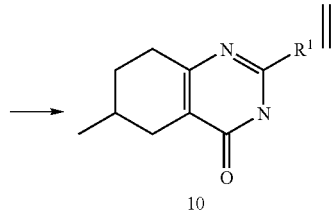

A compound according to formula 13 is obtained by treating a building block according to formula 5 (with S-A in the position of $R^1$), which is generated in analogy to steps 1 and 2, with an excess of an amine (e.g. morpholine) at temperatures between 150° C. and 200° C. in a sealed reaction tube for 10 to 24 hours, as required.

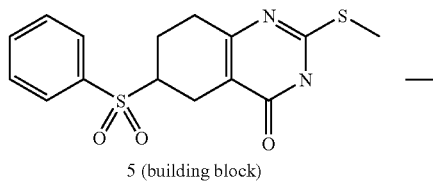

5 (building block)

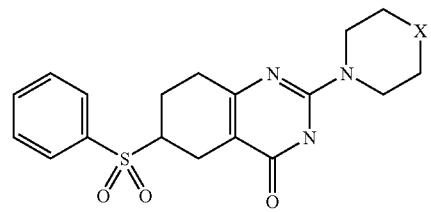

13

Compounds according to formula 15 are obtained in analogy to compounds according to formula 6. Compounds according to formula 14 are obtained in analogy to compounds according to formula 7.

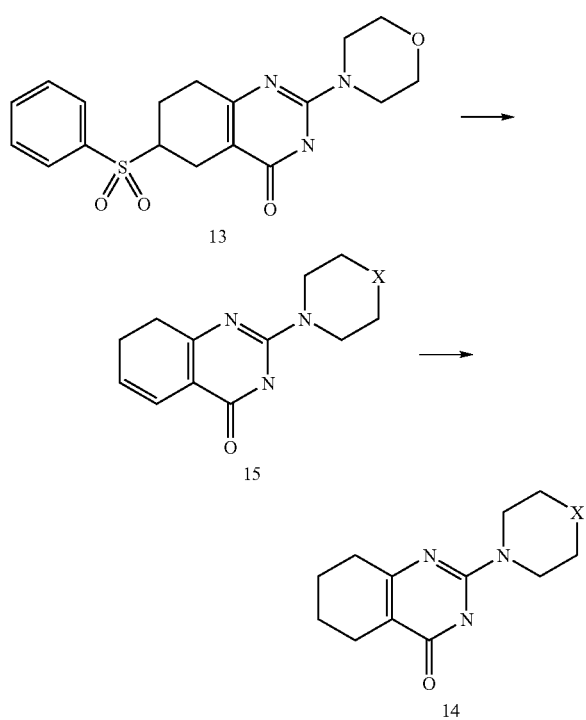

All crude products were subjected to standard chromatography using solvent mixtures containing methanol, ethanol, isopropanol, n-hexane, cyclohexane or petrol ether, respectively.

For a further detailed description of the manufacturing processes, please see also the examples 1-7 and the following general description of the preferred conditions.

A physiologically acceptable salt of a compound according to formula I can also be obtained by isolating and/or treating the compound of formula I obtained by the described reaction with an acid or a base.

The compounds of the formula I and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the formula I. On the other hand, it is possible to carry out the reaction stepwise.

Preferably, the reaction of the compounds is carried out in the presence of a suitable solvent, that is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of the formula I can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the formula I.

On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the formula I can be liberated from their salts by treatment with strong bases, such as sodium hydroxide, potassium hydroxide, sodium carbonate or potassium carbonate, so long as no further acidic groups are present in the molecule. In the cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

Surprisingly, we further found new tetrahydro- and dihydroquinazolinone derivatives, which show pharmaceutical activities as protein kinase modulators (activators or inhibitors) and therefore are useful for the treatment of the above-mentioned diseases.

Therefore, a preferred embodiment of the present invention are compounds of the formula IV,

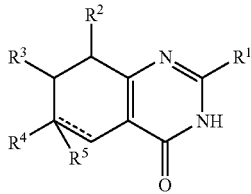

IV wherein $R^1$, $R^2$, $R^3$, $R^4$, $R^5$ and ----- are as defined above, with the proviso, that at least one of the residues $R^3$, $R^4$ and $R^5$ must have a meaning other than H or ----- is a double bond,
and the physiologically acceptable salts, derivatives, prodrugs, solvates and stereoisomers thereof, including mixtures thereof in all ratios.

A further preferred embodiment of the present invention are compounds according to the formula IV, wherein
----- is a single bond,
$R^1$ is $Ar^1$, S-A or Het,
$R^2$, $R^3$, $R^5$ are H,
$R^4$ is $SO_2Ar^2$,
and the physiologically acceptable salts, derivatives, prodrugs, solvates and stereoisomers thereof, including mixtures thereof in all ratios.

A further preferred embodiment of the present invention are compounds according to the formula IV, wherein
----- is a double bond,
$R^1$ is $Ar^1$, S-A or Het,
$R^2$, $R^3$, $R^4$, are H,
$R^5$ is absent,
and the physiologically acceptable salts, derivatives, prodrugs, solvates and stereoisomers thereof, including mixtures thereof in all ratios.

A further preferred embodiment of the present invention are compounds according to the formula IV, wherein
----- is a single bond,
$R^1$ is phenyl,
$R^2$, $R^3$ are H,
$R^4$ is $SO_2Ar^2$,
$R^5$ is A,
and the physiologically acceptable salts, derivatives, prodrugs, solvates and stereoisomers thereof, including mixtures thereof in all ratios.

A further preferred embodiment of the present invention are compounds according to the formula IV, wherein
----- is a single bond,
$R^1$ is phenyl,
$R^2$, $R^3$, $R^4$ are H,
$R^5$ is A,
and the physiologically acceptable salts, derivatives, prodrugs, solvates and stereoisomers thereof, including mixtures thereof in all ratios.

A further preferred embodiment of the present invention are compounds according to the formula IV, wherein
----- is a double bond,
$R^1$ is phenyl,
$R^2$, $R^3$ are H,
$R^4$ is A,
$R^5$ is absent,
and the physiologically acceptable salts, derivatives, prodrugs, solvates and stereoisomers thereof, including mixtures thereof in all ratios.

A further preferred embodiment of the present invention are compounds according to formula IV, wherein
----- is a single bond,
$R^1$ is Het,
$R^2$, $R^3$, $R^5$ are H,
$R^4$ is $SO_2Ar^2$,
and the physiologically acceptable salts, derivatives, prodrugs, solvates and stereoisomers thereof, including mixtures thereof in all ratios.

An especially preferred embodiment of the present invention are compounds according to formula IV, wherein the compounds are selected from the group consisting of
a) 6-Benzenesulfonyl-2-phenyl-5,6,7,8-tetrahydroquinazolin-4(3H)-one
b) 6-Benzenesulfonyl-2-(p-chlorophenyl)-5,6,7,8-tetrahydroquinazolin-4(3H)-one
c) 6-Benzenesulfonyl-2-(o-bromophenyl)-5,6,7,8-tetrahydroquinazolin-4(3H)-one
d) 6-Benzenesulfonyl-2-(o-fluorophenyl)-5,6,7,8-tetrahydroquinazolin-4(3H)-one
e) 6-Benzenesulfonyl-2-[(p-benzyloxy)phenyl]-5,6,7,8-tetrahydroquinazolin-4(3H)one
f) 6-Benzenesulfonyl-2-(o-biphenyl)-5,6,7,8-tetrahydroquinazolin-4(3H)-one
g) 6-Benzenesulfonyl-2-(methylthio)-5,6,7,8-tetrahydroquinazolin-4(3H)-one
h) 2-Phenyl-7,8-dihydroquinazolin-4(3H)-one
i) 2-(p-Chlorophenyl)-7,8-dihydroquinazolin-4(3H)-one
j) 2-(o-Bromophenyl)-7,8-dihydroquinazolin-4(3H)-one
k) 2-(o-Fluorophenyl)-7,8-dihydroquinazolin-4(3H)-one
l) 2-(p-Benzoyloxyphenyl)-7,8-dihydroquinazolin-4(3H)-one
m) 2-(o-Biphenyl)-7,8-dihydroquinazolin-4(3H)-one
n) 2-Methylthio-7,8-dihydroquinazolin-4(3H)-one
o) 6-Benzenesulfonyl-6-methyl-2-phenyl-5,6,7,8-tetrahydroquinazolin-4(3H)-one
p) 6-Benzenesulfonyl-6-ethyl-2-phenyl-5,6,7,8-tetrahydroquinazolin-4(3H)-one
q) 6-Methyl-2-phenyl-5,6,7,8-tetrahydroquinazolin-4(3H)-one
r) 6-Ethyl-2-phenyl-5,6,7,8-tetrahydroquinazolin-4(3H)-one
s) 6-Methyl-2-phenyl-7,8-dihydroquinazolin-4(3H)-one
t) 6-Ethyl-2-phenyl-7,8-dihydroquinazolin-4(3H)-one
u) 6-Benzenesulfonyl-7-methyl-2-phenyl-5,6,7,8-tetrahydroquinazolin-4(3H)one
v) 6-Benzenesulfonyl-2-(morpholine-4-yl)-5,6,7,8-tetrahydroquinazolin-4(3H)-one
w) 2-(4-benzylpiperazin-1-yl)-6-Benzenesulfonyl-5,6,7,8-tetrahydroquinazolin-4(3H)-one x) 6-Benzenesulfonyl-2-(4-methylpiperazin-1-yl)-5,6,7,8-tetrahydroquinazolin-4(3H)-one
y) 2-(Morpholin-4-yl)-7,8-dihydroquinazolin-4(3H)-one
z) 2-(4-Benzylpiperazin-1-yl)-7,8-dihydroquinazolin-4(3H)-one
aa) 2-(4-Methylpiperazin-1-yl)-7,8-dihydroquinazolin-4(3H)-one and the physiologically acceptable salts, derivatives, prodrugs, solvates and stereoisomers thereof, including mixtures thereof in all ratios.

As stated above the compounds according of the formula IV are effective modulators (activators or inhibitors) of one or more protein kinases selected from the group of Raf, Mek, PKB, Tie2, PDGFR and VEGFR.

Thus, the compounds of the invention may also be useful as reagents for studying signal transduction, protein kinases or any of the clinical disorders listed throughout this application.

For the identification of a signal transduction pathway and the detection of cross talks with other signaling pathways suitable models or model systems have been generated by various scientists, for example cell culture models (e.g. Khwaja et al., EMBO, 1997, 16, 2783-93) and transgenic animal models (e.g. White et al., Oncogene, 2001, 20, 7064-7072). For the examination of particular steps in the signal transduction cascade, interfering compounds can be used for signal modulation (e.g. Stephens et al., Biochemical J., 2000, 351, 95-105). The compounds according to the invention may also be useful as reagents for the examination of kinase dependent signal transduction pathways in animal and/or cell culture models or any of the clinical disorders listed throughout this application.

The measurement of kinase activity is a well-known technique feasible for each person skilled in the art. Generic test systems for kinase activity detection with substrates, for example histone (e.g. Alessi et al., FEBS Lett. 1996, 399, 3, page 333-8) or myelin basic protein are well described in the literature (e.g. Campos-González, R. and Glenney, Jr., J. R. 1992 J. Biol. Chem. 267, Page 14535).

For the identification of kinase inhibitors various assay systems are available (see for example Walters et al., Nature Drug Discovery 2003, 2; page 259-266). For example, in scintillation proximity assays (e.g. Sorg et al., J. of. Biomolecular Screening, 2002, 7, 11-19) or flashplate assays the radioactive phosphorylation of a protein or peptide as substrate with γATP can be measured. In the presence of an inhibitory compound no signal or a decreased radioactive signal is detectable. Furthermore homogeneous time-resolved fluorescence resonance energy transfer (HTR-FRET), and fluorescence polarization (FP) technologies are useful for assay methods (for example Sills et al., J. of Biomolecular Screening, 2002: 191-214).

Other non-radioactive ELISA based assay methods use specific phospho-antibodies (AB). The phospho-AB binds only the phosphorylated substrate. This binding is detectable with a secondary peroxidase conjugated antibody, measured for example by chemiluminescence (for example Ross et al., Biochem. J., 2002, 366: 977-981).

Furthermore, the compounds according to the invention can be tested for example by assays as described in example 10. Other assays are known from the literature and could readily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

A further preferred embodiment of the present invention is the use of the compounds of the present invention for the preparation of a medicament for the treatment and/or prevention of disorders.

A further preferred embodiment of the present invention is the use of the compounds according to the invention for the manufacture of a medicament for the treatment and/or prevention of disorders, which are caused, mediated and/or propagated by protein kinases.

Particularly, a further preferred embodiment of the present invention is the use of the compounds according to the invention for disorders as defined above for the compounds of the formula I, or any of the clinical disorders listed throughout this application.

The invention therefore also relates to compounds of the formula IV and the physiologically acceptable salts, derivatives, prodrugs, solvates and stereoisomers thereof, including mixtures thereof in all ratios as medicaments.

Thus, a further preferred embodiment of the present invention is a pharmaceutical composition, characterized in that it contains a therapeutically effective amount of one or more compounds according to the invention.

A further embodiment of the present invention is a pharmaceutical composition, characterized in that it further contains one or more additional compounds, selected from the group consisting of physiologically acceptable excipients, auxiliaries, adjuvants, diluents, carriers and pharmaceutically active agents other than the compounds according to the invention.

An additional preferred embodiment of the present invention is a set (kit) consisting of separate packets of
a) a therapeutically effective amount of one or more compounds according to the invention and
b) a therapeutically effective amount one or more further pharmaceutically active agents other than the compounds according to the invention.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

Tablets:
mixing of active ingredient/s and auxiliaries, compression of said mixture into tablets (direct compression), optionally granulation of part of mixture before compression.

Capsules:
mixing of active ingredient/s and auxiliaries to obtain a flowable powder, optionally granulating powder, filling powders/granulate into opened capsules, capping of capsules.

Semi-Solids (Ointments, Gels, Creams):
dissolving/dispersing active ingredients in an aqueous or fatty carrier;
subsequent mixing of aqueous/fatty phase with complementary fatty resp. aqueous phase, homogenization (creams only).

Suppositories (Rectal and Vaginal):
dissolving/dispersing active ingredients in carrier material liquified by heat (rectal: carrier material normally a wax; vaginal: carrier normally a heated solution of a gelling agent), casting said mixture into suppository forms, annealing and withdrawal suppositories from the forms.

Aerosols:
dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound according to this invention and one or more additional compounds other than the compounds according to the invention, which show valuable pharmaceutical properties, preferably those pharmaceutical active agents other than the compounds according to the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or Vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropymethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension include, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The present invention includes within its scope prodrugs of the compounds of the present invention above. In general, such prodrugs will be functional derivatives of the compounds of the present invention, which are readily convertible in vivo into the required compound of the present invention. Conventional procedures for the selection and preparation of suitable prodrug derivatives are described, for example, in Design of Prodrugs, ed. H. Bundgaard, Elsevier, 1985.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds according to the invention is known to the skilled artisan or can be easily determined by standard methods known in the art.

The substances according to the invention are generally administered analogously to commercial preparations. Usually, suitable doses that are therapeutically effective lie in the range between 0.0005 mg and 1000 mg, preferably between 0.005 mg and 500 mg and especially between 0.5 and 100 mg per dose unit. The daily dose is preferably between about 0.001 and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The host, or patient, may be from any mammalian species, e.g., primate sp., particularly human; rodents, including mice, rats and hamsters; rabbits; equines, bovines, canines, felines; etc. Animal models are of interest for experimental investigations, providing a model for treatment of human disease.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of hyperproliferative disorders, the susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one hour and one week. For in vitro testing, cultured cells from a biopsy sample may be used. The viable cells, left after treatment, are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

Mass spectrometry (MS):ESI (electrospray ionisation) $(M+H)^+$

LIST OF ABBREVIATIONS AND ACRONYMS

AcOH acetic acid, anh anhydrous, atm atmosphere(s), BOC tert-butoxycarbonyl CDI 1,1'-carbonyl diimidazole, conc concentrated, d day(s), dec decomposition, DMAC N,N-dimethylacetamide, DMPU 1,3-dimethyl-3,4,5,6-tetrahydro-2(1H)-pyrimidinone, DMF N,N-dimethylformamide, DMSO dimethylsulfoxide, DPPA diphenylphosphoryl azide, EDCl 1-(3-dimethylaminopropyl)-3-ethylcarbodiimide, EtOAc ethyl acetate, EtOH ethanol (100%), $Et_2O$ diethyl ether, $Et_3N$ triethylamine, h hour(s), MeOH methanol, pet. ether petroleum ether (boiling range 30-60° C.), temp. temperature, THF tetrahydrofuran, TFA trifluoroAcOH, Tf trifluoromethanesulfonyl.

EXAMPLE 1

Checking various methods for preparation of amidines from nitrites, we found that the method described by R. T. Boere, R. T. Onkley, R. W. Reed was the best for our substrates (R. A. Moss, J. Terpinski, D. P. Cox, D. Z. Denneey, K. K. Jespersen, J. Amer. Chem. Soc. 1985, 107, 2743-2748; R. T. Boere, R. T. Onkley, R. W. Reed, J. Organomet. Chem. 1987, 331, 161-168; F. C. Shaefer, A. P. Krapcho, J. Org. Chem. 1962, 27, 1255-1258; A. Thurkauf, A. Hutchison, J. Peterson, R. Meade, J. Med. Chem. 1995, 38, 2251-2255; W. Saal, R. A. Engh, A. Eichinger, B. Gabriel, R. Kucznierz, J. Saure, Arch. Phar. 1996, 329, 73-82).

When a THF solution of aryl nitrites is added to a 1 N solution of LiHMDS in hexane followed by quenching with 5-6 N isopropanolic HCl, amidines (see formulae 2b-e) are formed and isolated in good to excellent yields. Surprisingly, under the same conditions o-phenyl benzonitrile fails to give amidine (see formula 2). This compound is prepared by a modified method of Wolfgang von der Sall et al. (W. Saal, R. A. Engh, A. Eichinger, B. Gabriel, R. Kucznierz, J. Saure, Arch. Phar. 1996, 329, 73-82). When a solution of o-phenyl benzonitrile in toluene is added to a freshly prepared solution of MeAl(Cl)$NH_2$ in toluene, the compound of formula 2f is isolated in 58% yield (Scheme 1).

Scheme 1: Synthesis of amidines from nitriles. Conditions A: LiHMDS (1N, hexane), THF, 25° C., 4 h; conditions B: $Me_3Al$ (1M, toluene), $NH_4Cl$, toluene, 120° C., 15 h

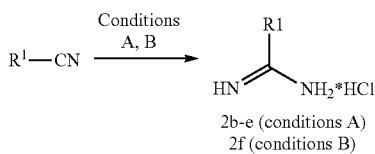

2b-e (conditions A)
2f (conditions B)

| $R^1$ | Reaction Conditions | Product | Yield (%) |
|---|---|---|---|
| p-ClC$_6$H$_4$ | A | 2b | 93 |
| o-BrC$_6$H$_4$ | A | 2c | 91 |
| o-FC$_6$H$_4$ | A | 2d | 80 |
| p-(C$_6$H$_5$CH$_2$O)C$_6$H$_4$ | A | 2e | 92 |
| o-PhC$_6$H$_4$ | B | 2f | 58 |

EXAMPLE 2

When a mixture of methyl 2-chloro-2-cyclopropylidineacetate (see formula 1) and two equivalents of benzamidine hydrochloride (see formula 2a) is stirred in dioxane in the presence of 4 equivalents of triethylamine for 48 h at room temperature, 3-phenyl-2,4-diazabicyclo[4.2.0]octa-1(6),2-diene-5-one (see formula 3a) is isolated in 83% yield. Similarly, under the same conditions the corresponding pyrimidinones are obtained in good yields (68-82%). Less reactive S-methylisothiourea hemisulpahte (see formula 2g) produces the corresponding pyrimidinone (see formula 3g) at 50° C. in 74% yield (Scheme 2).

Scheme 2: Michael addition of amidines to compounds of formula 1 for synthesis of cyclobutene annelated pyrimidinones (see formula 3).

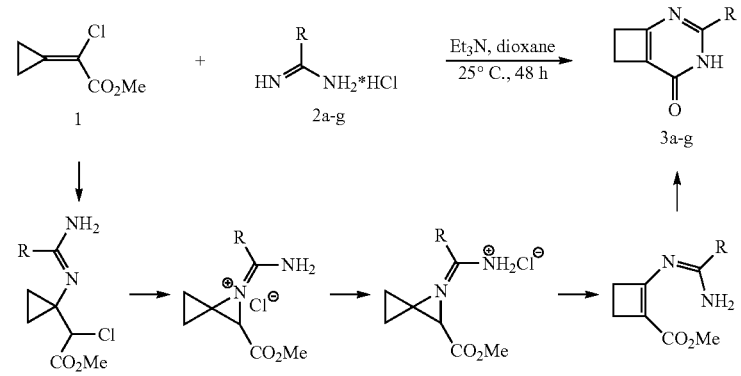

| Amidines | R (=$R^1$ according to the invention) | Product | Yield (%) |
|---|---|---|---|
| 2a | Ph | 3a | 83 |
| 2b | p-ClC$_6$H$_4$ | 3b | 78 |
| 2c | o-BrC$_6$H$_4$ | 3c | 76 |
| 2d | o-FC$_6$H$_4$ | 3d | 82 |
| 2e | p-(C$_6$H$_5$CH$_2$O)C$_6$H$_4$ | 3e | 68 |
| 2f | o-PhC$_6$H$_4$ | 3f | 80 |
| 2g | SMe | 3g | 74* |

*Reaction was carried out at 50° C.

These cyclobutene-annelated pyrimidinones (see formula 3) resemble hetero analogues of benzocyclobutene and, as expected, also undergo a thermal ring opening and a subsequent reaction with dienophiles to give tetrahydroquinazolinone derivatives. In order to optimize the reaction conditions, we choose the compound of formula 3a. As reported before (M. Nötzel, K. Rauch, T. Labahn, A. de Meijere, Org. Lett. 2002, 4, 839-841) the reaction of the compound of formula 3a with excess of methyl acrylate or acrylonitrile leads to inseparable mixtures of diasteriomers. First reactions of the compound of formula 3a with excess of phenyl vinyl sulfone (see formula 4) in toluene or in 1,2-dichlorobenzene at 175° C. in a closed pyrex tube for 12 h gives very poor yields of the corresponding Diels-Alder adduct (Table 1, entries 1, 2), but interestingly only one regioisomer of it. The yields are increased, by carrying out the reaction under solvent free conditions. The melting point of the compound of formula 4 is 68° C., therefore, we intended to do this reaction in a liquid of the compound of formula 4. When a mixture of the compound of formula 3a and 10-fold excess of the compound of formula 4 is heated at 175° C. for 12 h, 2-phenyl-6-benzenesulfonyl-5,6,7,8-tetrahydroquinazolin-4(3H)-one (see formula 5a) is isolated in 84% yield as one regioisomer (entry 3). The structure is assigned on the basis of $^1$H-NMR, $^{13}$C-NMR, HMBC (heteronuclear multiple bond coherence), HMQC (heteronuclear multiple quantum coherence), as well as MS. Decreasing the amount of the compound of formula 4 to four equivalents does not alter the yield (entry 4) but further going down to 1.5 equiv. or decreasing the temperature substantially reduces the yield (entries 5 and 6).

TABLE 1

Optimization of reaction conditions and yields of Diels-Alder reactions of the compound of formula 3a.

| Entry | Equiv. of PhSO$_2$=CH$_2$ | Reaction conditions | Yield of 5a (%) |
|---|---|---|---|
| 1 | 4 | 1,2-dichlorobenzene, 175° C., 12 h | 25 |
| 2 | 4 | toluene, 175° C., 12 h | 32 |
| 3 | 10 | neat, 175° C., 12 h | 84 |
| 4 | 4 | neat, 175° C., 12 h | 83 |
| 5 | 1.5 | neat, 175° C., 12 h | 49 |
| 6 | 4 | neat, 165° C., 12 h | 39 |

Since the optimal conditions have been found for the compound of formula 3a (entry 4), the ring-opening reactions are performed in the compounds of formulae 3a-g and the corresponding adducts of the compounds of formulae 5a-g are synthesized in good yields (Scheme 3).

Scheme 3: Regioselective Diels-Alder reactions of the compounds of formulae 3a-g with phenyl vinyl sulfone (see formula 4).

| Compound 3 | R$^1$ | Product 5 | Yield (%) |
|---|---|---|---|
| 3a | Ph | 5a | 83 |
| 3b | p-ClC$_6$H$_4$ | 5b | 59 |
| 3c | o-BrC$_6$H$_4$ | 5c | 43 |
| 3d | o-FC$_6$H$_4$ | 5d | 70 |
| 3e | p-(C$_6$H$_5$CH$_2$O)C$_6$H$_4$ | 5e | 66 |
| 3f | o-PhC$_6$H$_4$ | 5f | 65 |
| 3g | SMe | 5g | 56 |

After stepwise Michael addition and Diels-Alder reactions are successfully performed, it is interesting to try to carry out these two operations in one pot. Indeed, when phenyl vinyl sulfone is added to the crude reaction mixture of benzamidine hydrochloride (see formula 2a) and the compound of formula 1 in presence of Et$_3$N after 48 h in a pyrex bottle and heated to 175° C. for 12 h, the compound of formula 5a is isolated in 43% yield. A little higher yield is obtained in case of the compound of formula 3d (Scheme 4).

Scheme 4: One pot synthesis of tetrahydroquinalinones of forumulae 5a,d from the compounds of fourmula 1 and amidines according to formulae 2a,d.

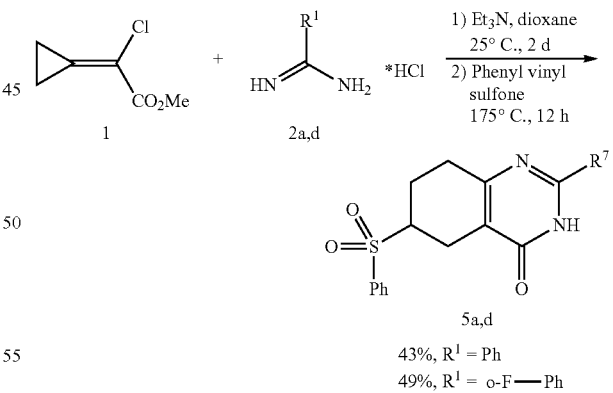

43%, R$^1$ = Ph
49%, R$^1$ = o-F—Ph

EXAMPLE 3

Since the tetrahydroquinazoline ring has been formed, the next issue is to remove the sulfonyl group. Although there are several methods known for this purpose, the method involving Na/Hg amalgam in the presence of Na$_2$HPO$_4$ (B. M. Trost, H. C. Arndt, P. E. Strege, T. R. Verhoeven, Tett. Lett. 1976, 39, 3477-3478) has been most widely used. However, when the compound of formula 5a as well as its O-TMS protected or N-Boc protected equivalent is reacted with Na/Hg and Na₂HPO₄ (4 equiv. each) in MeOH, only (deprotected) starting material is isolated without any reductive elimination. By changing the reagents to Na-sand/EtOH(Y. Masaki, Y. Serizawa, K. Nagata, K. Kaji, Chemistry Lett. 1984, 2105-2108; D. F. Taber, Q. Jiang, B. Chen, W. Zhang, C. L. Campbell, J. Org. Chem. 2002, 67, 4821-4827) only substantial amount of benzaldehyde is isolated. This problem is solved by using a two-step procedure: basic elimination of the PhSO₂-group followed by Pd-catalysed hydrogenation of C=C bond. When 3 equivalents of KOtBu are added to a THF solution of the compound of formula 5a, the elimination product, the compound of formula 6a, is obtained in 96% yield after 2 h. The subsequent hydrogenation of the compound of formula 6a under standard conditions in MeOH leads to the target substance 2-phenyl-5,6,7,8-tetrahydroquinazolinone (see formula 7a) in 91% yield. In a similar manner, the compounds of formulae 7c-f are obtained from the compounds of formulae 5c-f in excellent yields. Due to the low solubility of the compound of formula 6b and the compound of formula 6e in MeOH, the reaction is carried out in AcOH to give the compound of the compound of formula and the compound of formula 7e in 94% and 93% yield respectively. In case of the compound of formula 6g the hydrogenation reaction is not successful due to the presence of SMe group, which poisons the catalyst. Instead of the desired product, some amount of the material without SMe group is isolated. These results are summarized in Scheme 5.

Scheme 5: Basic elimination of PhSO₂H followed by hydrogenation: preparation of 2-substituted tetrahydro-quinazolinones: a) KOtBu (3 equiv), THF, 25° C., 2 h; b) Pd/C, H₂, MeOH or AcOH, 25° C., 4 h

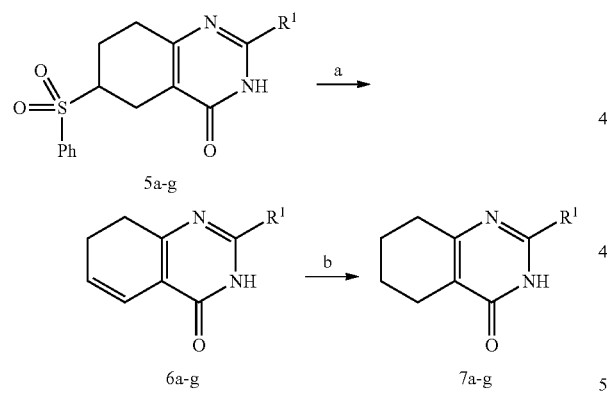

| Compound 5 | Compound 6 | Yield (%) | Compound 7 | Yield (%) |
|---|---|---|---|---|
| 5a | 6a | 96 | 7a | 91 |
| 5b | 6b | 95 | 7b | 94 |
| 5c | 6c | 93 | 7c | 91 |
| 5d | 6d | 94 | 7d | 92 |
| 5e | 6e | 92 | 7e | 93* |
| 5f | 6f | 87 | 7f | 93 |
| 5g | 6g | 98 | 7g | No reaction |

*Without benzyl group.

EXAMPLE 4

The presence of a strong electron acceptor at C-6—phenyl sulfonyl group—makes possible further derivatization at this centre, namely alkylation of the corresponding anion generated from an O- or N-protected precursor. Surprisingly, when a THF solution of N-Boc protected compound (the compound of formula 5a-Boc) is subjected to nBuLi followed by treatment with MeI, no alkylation at C-6 is observed, and only N-Boc-2-phenyl-8-methyl-6-phenylsulfonyltetrahydroquinazolin-one (see formula 8) is isolated instead. Changing the base from nBuLi to either LDA or NaHMDS gives the same product in lower yield (Scheme 6).

Scheme 6: Alkylation at C-8 of N-Boc-protected compound of formula 5a.

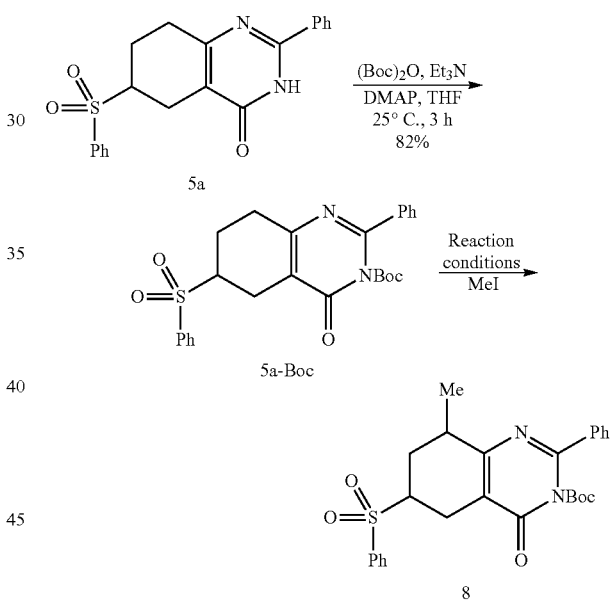

| Entry | Reaction conditions | Compound 8 Yield (%) |
|---|---|---|
| 1 | nBuLi, −78° C. → 25° C., THF, 2 h | 28 |
| 2 | LDA, −78° C. → 25° C., THF, 2 h | 19 |
| 3 | NaHMDS, −78° C. → 25° C., THF, 3 h | 14 |

However, substitution at C-6 position can be achieved by changing the protecting group. Thus, when O-TMS protected compound (see formula 5a-TMS) is subjected to nBuLi followed by treatment with alkyl halides, desired products of formulae 9a-b are obtained in good yields. Elimination of sulfone group followed by hydrogenation, leads to 2-phenyl-6-alkyltetrahydroquinazolinones (see formulae 10a-b) (Scheme 7).

Scheme 7: Alkylation at sulfone centre (C-6) followed by the removal of PhSO$_2$-group to prepare 2-alkyl-tetrahydroquinazolinones (see formulae 10a, b): a) HMDS (excess), (NH$_4$)$_2$SO$_4$, reflux, 10 h; 99% b) nBuLi, THF, −78°C., 30 min; R$^1$X, −78° C. →RT, 2 h; NH$_4$Cl/H$_2$O; c) KOtBu (3 equiv), THF, 25° C., 2 h; d) Pd/C, H$_2$, MeOH, 25° C., 4 h

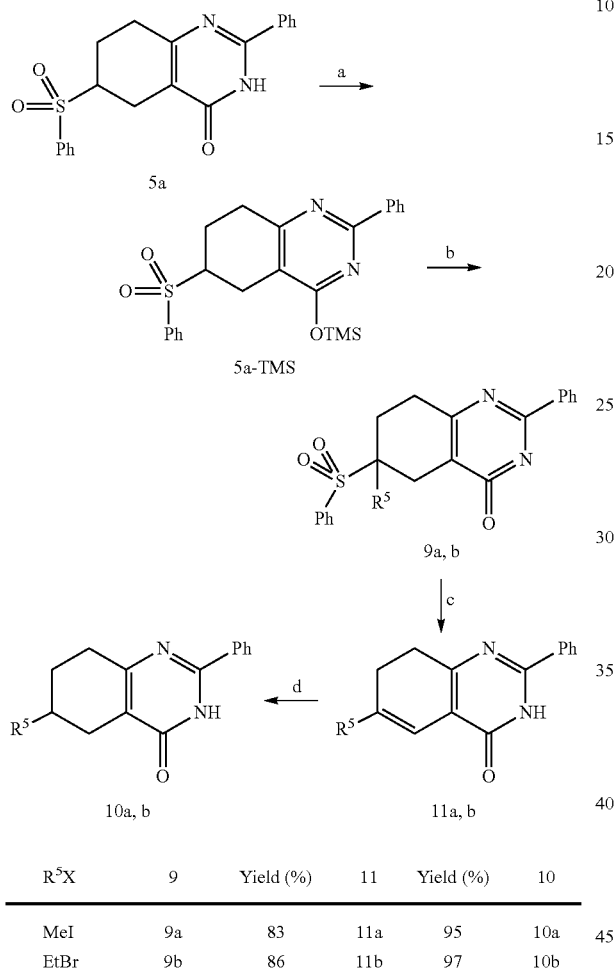

| R$^5$X | 9 | Yield (%) | 11 | Yield (%) | 10 |
|---|---|---|---|---|---|
| MeI | 9a | 83 | 11a | 95 | 10a |
| EtBr | 9b | 86 | 11b | 97 | 10b |

EXAMPLE 5

After successful substitution at C-6, we intend to explore a possibility to get a substituent also at the position 7. An obvious option is to use a phenyl propenyl sulfone. Indeed, when the compound of formula 3a reacts with (E)-p-tolyl-1-propenyl sulfone (see formula 4-Me), the corresponding cycloaddition product (see formula 12) is isolated, albeit in 27% yield, as a mixture of two diasteriomers. An attempt to introduce an ethyl group fails, because the corresponding sulfone polymerizes under the reaction conditions (Scheme 8).

Scheme 8: Reaction of p-tolyl-1-propenyl sulfone (see formula 4-Me) with the compound of formula 3a.

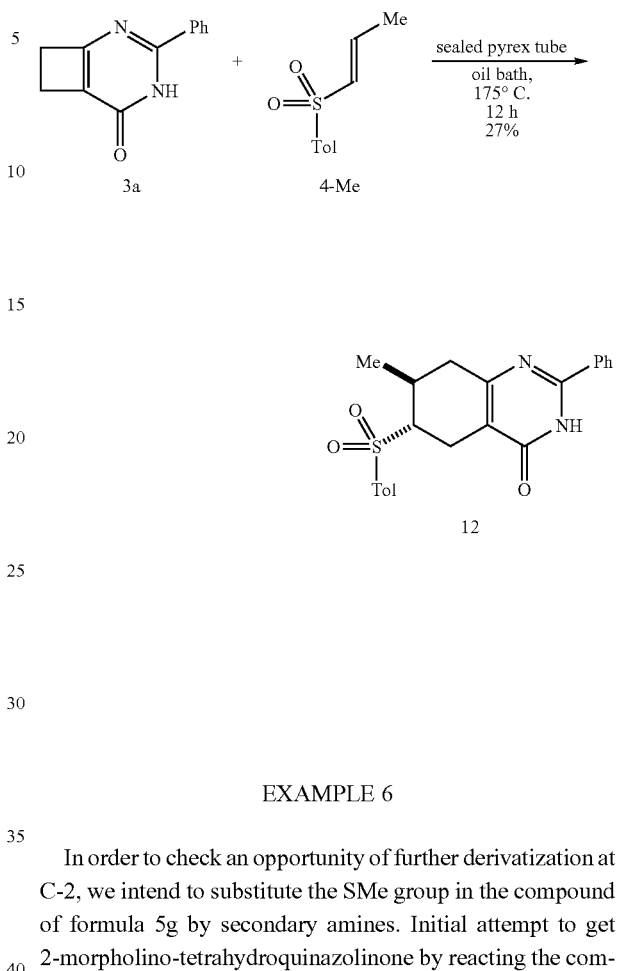

EXAMPLE 6

In order to check an opportunity of further derivatization at C-2, we intend to substitute the SMe group in the compound of formula 5g by secondary amines. Initial attempt to get 2-morpholino-tetrahydroquinazolinone by reacting the compound of formula 5g with 2 equivalents of morpholine in DMF at 180° C. for 12 h in a sealed pyrex bottle fails, and this experiment affords only 2-dimethylamino-6-phenylsulfonyltetrahydroquinazolinone (see formula 16) in 78% yield. Obviously, this product is formed due to the instability of DMF at higher temperature and substitution of SMe by dimethyl amine. This is confirmed by heating the compound of formula 5g in an excess of DMF at 180° C. without morpholine: the same product is isolated in 86% yield. When the compound of formula 5g is heated at 180° C. with an excess of morpholine without solvent for 12 h, 2-morpholino-6-phenylsulfonyltetra-hydroquinazolinone (see formula 13a) is obtained in 93% yield. In a similar way, N-benzyl and N-methyl piperazine successfully gives the corresponding substitution products of formulae 13b,c in 92% and 91% yield respectively. Unlike before, 5 equiv of KOtBu and a longer period of time (15 h) are necessary to complete the elimination reaction in the compounds of formulae 13a-c. Hydrogenation of the compounds of formulae 15a-c by using standard conditions gives 2-piperazinyl and 2-N-methylpiperazinyl derivatives of the compounds of formulae 14a-c in very good yield (Scheme 9).

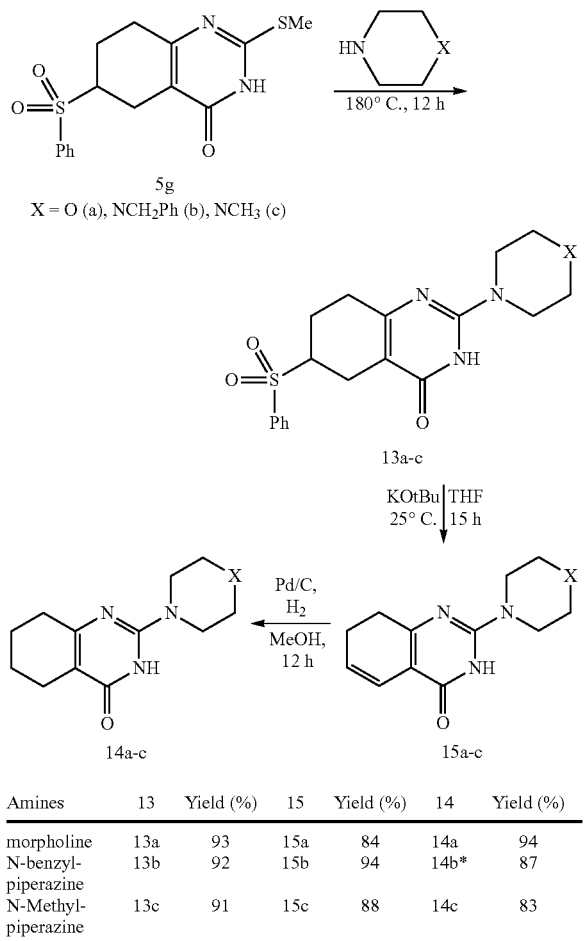

Scheme 9: Nucleophilic substitution of SMe group in the compound of formula 5g by amines.

X = O (a), NCH₂Ph (b), NCH₃ (c)

| Amines | 13 | Yield (%) | 15 | Yield (%) | 14 | Yield (%) |
|---|---|---|---|---|---|---|
| morpholine | 13a | 93 | 15a | 84 | 14a | 94 |
| N-benzyl-piperazine | 13b | 92 | 15b | 94 | 14b* | 87 |
| N-Methyl-piperazine | 13c | 91 | 15c | 88 | 14c | 83 |

*Without N-benzyl group.

EXAMPLE 7

All reagents are used as purchased without further purification. All reactions in organic solvents are carried out using standard Schlenk techniques under an atmosphere of dry nitrogen. Solvents are purified and dried prior to use according to conventional methods; tetrahydrofuran (THF), dioxane, toluene are freshly distilled from sodium/benzophenone. —Solvents are abbreviated as follows: DCM=dichloromethane, EE=ethyl acetate, MeOH=methanol, PE=pentane, Et₂O=diethyl ether, HMDS=hexamethyl disilazane. —$^1$H and $^{13}$C NMR spectra are recorded at ambient temperature on either Bruker AM 250 or Varian 200 or 300 instrument. Chemical shifts (δ) are given in ppm relative to resonances of solvent ($^1$H, 7.26 ppm for chloroform or 2.49 ppm for [D₆]DMSO; $^{13}$C, 77.0 ppm for CDCl₃, or 39.7 ppm for [D₆]DMSO. Coupling constants (J) are given in Hz. Multiplicities of signals are described as follows: s=singlet, br. s=broad singlet, d=doublet, t=triplet, m=multiplet, dt=doublet of triplets. —The multiplicities of signals are determined by the DEPT technique: DEPT: +=primary (CH₃) or tertiary (CH) (positive DEPT-signal), -=secondary (CH₂) (negative DEPT-signal), $C_{quat}$=quaternary C-atoms. J values in $^{13}$C NMR spectra refer to $^{13}$C-$^{19}$F coupling. —IR: Bruker IFS 66. —MS: Varian MAT CH 7, MAT 731. —Chromatographic separations are carried out on Merck silica gel 60 (0.063-0.200 mm, 70-230 mesh ASTM). The dimensions of the columns are given in cm as "diameter× height of the silica column". —TLC: Machery-Nagel, ready to use TLC plates Alugram® Sil G/UV₂₅₄. Detection under UV-light at 254 nm. —Melting points (uncorrected) are determined in capillaries with a Büchi 510 apparatus. Elemental analyses: Mikroanalytisches Laboratorium des Instituts für Organische Chemie der Universität Göttingen. Room temperature is abbreviated as RT. Pd/C was purchased from Merck.

Benzamidine hydrochloride (see formula 2a), S-methyl-isothiourea hemisulpahte (see formula 2g) were purchased from Aldrich.

General Method A p-Chlorobenzamidine hydrochloride (see formula 2b): Into a 50 mL dry reaction flask charged with 1 M LiHMDS in THF (22 mmol), p-chlorobenzonitrile (2.76 g, 20.0 mmol) in 2 mL of THF is added, and the reaction mixture is kept stirring at RT for 4 h, at which point 5-6 N HCl (in iPrOH, 15 mL) is added. The crude reaction mixture is kept at 0° C. overnight. The precipitated product is filtered, washed with diethyl ether to yield 3.5 g (93%) of the compound of formula 2b as a white solid, m.p. 238° C. (lit m.p. 243-245° C.) (E. Ragona, D. L. Nelson, M. Mares-Guis, J. Amer. Chem. Soc. 1975, 97, 6844-6848). —IR (KBr): nu(tilde)=3239 cm⁻¹, 3054, 1678, 1460, 1401, 1036, 715. —$^1$H NMR (250 MHz, [D₆]DMSO): δ=7.60-7.77 (m, 2H), 7.85-7.97 (m, 2H), 8.4 (br. s, 3H, NH). —$^{13}$C NMR (62.9 MHz, [D₆]DMSO), δ=126.79 ($C_{quat}$), 129.36 (+), 130.57 (+), 139.1 ($C_{quat}$), 165.1 (NCN).

o-Bromobenzamidine hydrochloride (see formula 2c): Using the general method A, 4.3 g (91%) of the compound of formula 2c is obtained from o-bromobenzonitrile (3.68 g, 20.0 mmol) and 22 mL of 1 M LiHMDS as a white solid, m.p.>250° C. —IR (KBr): nu(tilde)=3228 cm⁻¹, 3059, 1669, 1458, 1401, 1030, 728. —$^1$H NMR (250 MHz, CD₃OD): δ=4.92 (br. s, 4H, NH), 7.54-7.68 (m, 3H), 7.74-7.86 (m, 1H). —$^{13}$C NMR (62.9 MHz, CD₃OD): δ=121.1 ($C_{quat}$), 129.5 (+), 131.0 (+), 133.3 ($C_{quat}$), 134.8 (+), 135.0 (+), 168.4 (NCN). —MS (DCI, 70 eV) m/z (%): 399 (6) [2M−2Na+H⁺], 216 (M−HCl+NH₄⁺), 199 (100) [M−HCl+H⁺].

o-Fluorobenzamidine hydrochloride (see formula 2d): Using the general method A, 2.8 g (80%) of the compound of formula 2d is obtained from o-fluorobenzonitrile (2.40 g, 20.0 mmol) and 22 mL of 1 M LiHMDS as a white solid, m.p. 98-100° C. —IR (KBr): nu(tilde)=3477 cm⁻¹, 3144, 1701, 1674, 1476, 1401, 1228, 774, 684. —$^1$H NMR (250 MHz, CD₃OD): δ=4.98 (br. s, 4H, NH), 7.38-7.49 (m, 2H), 7.64-7.80 (m, 1H). —$^{13}$C NMR (62.9 MHz, CD₃OD): δ=118.2 (d, $^2J_{C-F}$=9.2 Hz, +), 118.8 (d, $^2J_{C-F}$=3.2 Hz, $C_{quat}$) 126.6 (+), 131.4 (+), 136.8 (+), 161.2 (d, $^1J_{C-F}$=253.7 Hz, $C_{quat}$), 164.9 (NCN).

p-Benzyloxybenzamidine hydrochloride (see formula 2e): Using the general method A, 2.42 g (92%) of the compound of formula 2e is obtained from o-benzyloxybenzonitrile (2.09 g, 10 mmol) and 11 mL of 1 M LiHMDS as a white solid, m.p. 181-182° C. (lit m.p. 179-180° C.) (R. Pierre, B. Jean-Daniel, N. Emmanuel, D. Catherine, P. Francois, A. Marie-Luce, Eur. J. Med. Chem. 1989, 24, 427-434) —IR (KBr): nu(tilde)=3317 cm⁻¹, 3125, 1677, 1609, 1486, 1267, 1190, 1010, 837, 763. —$^1$H NMR (250 MHz, CD₃OD): δ=4.92 (br. s, 4H, NH), 5.24 (s, 2H), 7.19-7.28 (m, 2H), 7.32-7.52 (m, 5H) 7.79-7.84 (m, 2H). —$^{13}$C NMR (75.5 MHz, CD₃OD): δ=71.4 (−, OCH₂), 116.7 (+), 121.14 ($C_{quat}$), 128.7 (+), 129.2 (+), 129.6 (+), 131.1 (+), 137.6 ($C_{ipso}$) 164.9 ($C_{ipso}$) 168.4 (NCN).

General Method B o-Phenylbenzamidine (see formula 2f): To a suspension of NH₄Cl (2.14 g, 40.0 mmol) in 40 mL of toluene is added Me₃Al (2 M in toluene, 40 mmol) over a period of 30 min at 5° C. Then the temperature is allowed to come to RT, and stirring is continued until evolution of methane ceased (~2 h). To this solution of MeAl(Cl)NH$_2$, o-biphenyl nitrile (2.86 g, 16 mmol) in 5 mL of toluene is added in 5 min, and the resulting solution is refluxed for 20 h. After cooling, the crude reaction mixture is poured into a suspension of 20 g of SiO$_2$ in 100 mL of dichloromethane, filtered and the solid residue is washed with 2×50 mL of MeOH, and the solvent is removed in vacuo from the combined solutions. The residue is suspended in 100 mL of water, 30 mL of 2 N HCl are added to it and extracted with ethylacetate (2×50 mL). To the aq. layer 60 mL of 2 N NaOH is added and extracted with DCM (3×50 mL). This DCM layer was dried with MgSO$_4$, filtered, and the solvent is removed in vacuo to yield 1.83 g (58%) of the compound of formula 2f as a white solid, m.p. 148-150° C. (lit. m.p. 149-151° C.[11e]). —IR (KBr): nu(tilde)=3408 cm$^{-1}$, 3059, 1674, 1639, 1600, 1427, 1199, 744, 701. —$^1$H NMR (250 MHz, [D$_6$]DMSO): δ=5.4 (br. s, 3H, NH), 7.31-7.55 (m, 9H). —$^{13}$C NMR (62.9 MHz, [D$_6$]DMSO): δ=127.3, 128.1, 128.3, 128.6, 129.2, 136.2, 137.5, 139.0, 140.5, 165.9 (NCN). —MS (70 eV), m/z (%): 196 (10) [M$^+$], 195 (100) [M$^+$−1], 178 (31), 77 (8).

General Procedure 1 (GP-1)

2,4-Diazabicyclo[4.2.0]octa-1(6),2-dien-5-ones (see formula 3): A solution of methyl 2-chloro-2-cyclopropylidineacetate (see formula I), 2 mol. of respective amidine (see formula 2) and 4 mol. of Et$_3$N is stirred in anhydrous dioxane at room temp. for 48 h. After filtration the solid residue is suspended in DCM and washed with water. The aq. layer is washed three times with DCM. The combined organic layers are dried over MgSO$_4$, evaporated in vacuo and the crude product is subjected to column chromatography.

3-Phenyl-2,4-diazabicyclo[4.2.0]octa-1(6),2-dien-5-one (see formula 3a): The crude product obtained from the compound of formula 1 (365 mg, 2.5 mmol), benzamidine hydrochloride (see formula 2a, 793 mg, 5.00 mmol) and triethylamine (1.01 g, 10 mmol) in 25 mL of dioxane according to GP-1 is subjected to column chromatography (R$_f$=0.3, Et$_2$O, 1.5×30 cm, 30 g SiO$_2$) to yield 411 mg (83%) of the compound of formula 3a as a white solid, m.p. 191° C. —IR (KBr): nu(tilde)=3008 cm$^{-1}$, 2937, 1670, 1557, 1498, 1321, 1082, 838, 766. —$^1$H NMR (250 MHz, CDCl$_3$): δ=3.01 (t, J=3.2 Hz, 2H), 3.22 (t, J=3.2 Hz, 2H), 7.47-7.53 (m, 3H), 8.05-8.2 (m, 2H), 12.54 (br. s, 1H, NH). —$^{13}$C NMR (62.9 MHz, CDCl$_3$): δ=25.7 (−), 33.7 (−), 124.1 (C-6), 127.6 (+), 128.9 (+), 131.7, (+), 132.5 (C$_{ipso}$), 158.6 (C-1/C-3), 160.52 (C-3/C-1), 171.9 (C-5). —MS (70 eV), m/z (%): 198 (100) [M$^+$], 170 (7) [M$^+$−CH$_2$CH$_2$], 104 (91) [HN=CPh$^+$], 77 (44) [Ph$^+$]. —C$_{12}$H$_{10}$N$_2$O (198.2): calcd. C, 72.71; H, 5.08; N, 14.13. found C, 72.44; H, 5.38; N, 14.03.

3-(p-Chlorophenyl)-2,4-diazabicyclo[4.2.0]octa-1(6),2-dien-5-one (see formula 3b): The crude product obtained from the compound of formula 1 (365 mg, 2.5 mmol), p-chlorobenzamidine hydrochloride (see formula 2b, 955 mg, 5.00 mmol) and triethylamine (1.01 g, 10 mmol) in 25 mL of dioxane according to GP-1 is subjected to column chromatography (R$_f$=0.31, DCM/MeOH=25:1, 1.5×20 cm, 25 g SiO$_2$) to yield 455 mg (78%) of the compound of formula 3b as a white solid, m.p. 218-219° C. —IR (KBr): nu(tilde)=3078 cm$^{-1}$, 2938, 1668, 1520, 1491, 1322, 1092, 1076, 837, 760. —$^1$H NMR (250 MHz, [D$_6$]DMSO): δ=2.9 (t, J=3.1 Hz, 2H), 3.15 (t, J=3.1 Hz, 2H), 7.6 (d, J=8.5 Hz, 2H), 8.05 (d, J=8.5 Hz, 2H). —$^{13}$C NMR (62.9 MHz, [D$_6$]DMSO), δ=25.1 (−), 33.6 (−), 126.1 (C-6), 128.9 (+), 129.8 (+), 136.6 (C$_{ipso}$), 152.1 (C—Cl), 158.2 (C-1/C-3), 159.6 (C-3/C-1), 171.5 (C-5). —MS (70 eV), m/z (%): 234/232 (33/100) [M$^+$], 204 (6) [M$^+$−C$_2$H$_4$], 138/140 (57/18) [HN=CC$_6$H$_4$Cl$^+$], 111 (15) [C$_5$H$_4$Cl$^+$]. —C$_{12}$H$_9$ClN$_2$O (232.7): calcd. C, 61.95; H, 3.90; N, 12.04. found C, 61.63; H, 3.78; N, 11.83.

3-(o-Bromophenyl)-2,4-diazabicyclo[4.2.0]octa-1(6),2-dien-5-one (see formula 3c): The crude product obtained from the compound of formula 1 (1.1 g, 7.5 mmol) o-bromobenzamidine hydrochloride (see formula 2c, 3.50 g, 15.0 mmol) and triethylamine (3.03 g, 30.0 mmol) in 60 mL of dioxane according to GP-1 is subjected to column chromatography (R$_f$=0.35, Et$_2$O/MeOH=50:1, 3×30 cm., 50 g SiO$_2$) to yield 1.59 g (76%) of the compound of formula 3c as a white solid, m.p. 178-179° C. —IR (KBr): nu(tilde)=2925 cm$^{-1}$, 2847, 1662, 1540, 1472, 1326, 1089, 778, 762. —$^1$H NMR (200 MHz, CDCl$_3$): δ=3.0 (t, J=4.2 Hz, 2H), 3.2 (t, J=4.2 Hz, 2H), 7.3-7.5 (m, 2H), 7.52-7.7 (m, 2H), 11.0 (br. s, 1H, NH). —$^{13}$C NMR (50.3 MHz, CDCl$_3$): δ=25.4 (−), 33.7 (−), 120.9 (C-6), 125.1 (C—Br), 127.7 (+), 130.9 (+), 132.0 (+), 133.7 (+), 134.6 (C$_{ipso}$), 157.6 (C-1/C-3), 160.3 (C-3/C-1), 171.2 (C-5). —MS (70 eV), m/z (%): 279/277 (21/22) [M$^+$+1], 278/276 (97/100) [M$^+$], 184/182 (41/42) [HNCC$_6$H$_4$Br$^+$], 102 (58), 95 (79). —C$_{12}$H$_{10}$BrN$_2$O (277.1): calcd. C, 52.01; H, 3.27; N, 10.11. found C, 51.92; H, 3.37; N, 9.94.

3-(o-Fluorophenyl)-2,4-diazabicyclo[4.2.0]octa-1(6),2-dien-5-one (see formula 3d): The crude product obtained from the compound of formula 1 (730 mg, 5 mmol), o-fluorobenzamidine hydrochloride (see formula 2d, 1.75 g, 10.0 mmol) and triethylamine (2.02 g, 20.0 mmol) in 50 mL of dioxane according to GP-1 is subjected to column chromatography (R$_f$=0.5, Et$_2$O/MeOH=25:1, 3×30 cm, 50 g SiO$_2$) to yield 884 mg (82%) of the compound of formula 3d as a white solid, m.p. 184-185° C. —IR (KBr): nu(tilde)=3095 cm$^1$, 2976, 2947, 1668, 1617, 1532, 1319, 1223, 1084, 753. —$^1$H NMR (200 MHz, CDCl$_3$): δ=3.04 (t, J=4.2 Hz, 2H), 3.25 (t, J=4.2 Hz, 2H), 7.16-7.42 (m, 2H), 7.48-7.62 (m, 1H), 7.91-8.20 (m, 1H), 10.22 (br. s, 1H, NH). —$^{13}$C NMR (50.3 MHz, CDCl$_3$): δ=25.4 (−), 33.8 (−), 116.6 (+, d, $^2J_{C-F}$=22.9 Hz) 120.1 (d, $^2J_{C-F}$=9.2 Hz, C$_{ipso}$), 125.0 (+, $^3J_{C-F}$=3.5 Hz), 130.9 (+, d, $^4J_{C-F}$=1.5 Hz), 133.6 (+, d, $^3J_{C-F}$=9.2 Hz), 156.7 (C-1/C-3), 156.8 (C-3/C-1), 160.2 (d, $^1J_{C-F}$=251 Hz), 171.0 (C-5). —MS (70 eV), m/z (%): 217 (17) [M$^+$+1], 216 (100) [M$^+$], 122 (42) [HN=CC$_6$H$_4$F$^+$], 102 (20), 95 (24) [C$_6$H$_4$F$^+$]. —C$_{12}$H$_{10}$FN$_2$O (116.2): calcd. C, 66.66; H, 4.20; N, 12.96. found C, 66.50; H, 4.28; N, 13.03.

3-(p-Benzyloxyphenyl)-2,4-diazabicyclo[4.2.0]octa-1(6),2-dien-5-one (see formula 3e): The crude product obtained from the compound of formula 1 (660 mg, 4.5 mmol) p-benzyloxybenzamidine hydrochloride (see formula 2e, 2.4 g, 9.00 mole) and triethylamine (1.82 g, 18.0 mol) in 50 mL of dioxane according to GP-1 is subjected to column chromatography (R$_f$=0.34, DCM/MeOH=25:1, 3×30 cm, 50 g, SiO$_2$) to yield 930 mg (68%) of the compound of formula 3e as a white solid, m.p. 212-213° C. —IR (KBr): nu(tilde)=3088 cm$^{-1}$, 2936, 1664, 1608, 1504, 1303, 1252, 1189, 843, 762. —$^1$H NMR (300 MHz, CDCl$_3$): δ=3.01 (t, J=3.8 Hz, 2H), 3.20 (t, J=3.8 Hz, 2H), 5.15 (s, 2H, OCH$_2$), 7.04-7.12 (m, 2H), 7.30-7.47 (m, 5H), 7.95-8.22 (m, 2H), 11.48 (br. s, 1H, NH). —$^{13}$C NMR (50.3 MHz, [D$_6$]DMSO): δ=24.6 (−), 32.9 (−), 69.4 (−, OCH$_2$), 114.7 (+), 122.5 (C-6), 124.9 (C$_{ipso}$), 127.6 (+), 127.8 (+), 128.4 (+), 129.4 (+), 136.5 (C$_{ipso}$), 156.7 (C$_{ipso}$), 159.9 (C-1/C-3), 160.9 (C-3/C-1), 169.9 (C-5). MS (70 eV), m/z (%): 304 (8) [M$^+$], 91 (100) [C$_7$H$_7^+$]. —C$_{19}$H$_{16}$N$_2$O$_2$ (304.6): calcd. C, 74.98; H, 5.30; N, 9.20. found C, 74.78; H, 5.01; N, 8.98.

3-(Biphenyl-2-yl)-2,4-diazabicyclo[4.2.0]octa-1(6),2-dien-5-one (see formula 3f): The crude product obtained from the compound of formula 1 (527 mg, 3.6 mmol) o-biphenylbenzamidine (see formula 2f, 1.40 g, 7.20 mole) and triethylamine (1.44 g, 14.2 mol) in 25 mL of dioxane according to GP-1 is subjected to column chromatography (R$_f$=0.41, Et$_2$O, 1.5×20 cm, 20 g, SiO$_2$) to yield 425 mg (80%) of the compound of formula 3f as a white solid, m.p. 176-177° C. —IR (KBr): nu(tilde)=2928 cm$^{-1}$, 1675, 1540, 1478, 1323, 1088, 976, 745, 698. —$^1$H NMR (250 MHz, CDCl$_3$): δ=2.92 (t, J=4.2 Hz, 2H), 3.18 (t, J=4.2 Hz, 2H), 7.22-7.41 (m, 5H), 7.44-7.78 (m, 4H), 9.22 (br. s, 1H, NH). —$^{13}$C NMR (50.3 MHz, CDCl$_3$): δ=25.0 (−) 33.5 (−), 123.8 (C-6), 127.7 (+), 128.1 (+), 128.8 (+), 129.8 (+), 130.7 (+), 132.3 (C$_{ipso}$) 139.2 (C$_{ipso}$) 140.6 (C$_{ipso}$), 157.3 (C-1/C-3), 161.9 (C-3/C-1), 170.8 (C-5). —MS (70 eV), m/z (%): 274 (42) [M$^+$], 273 (100) [M$^+$−1], 245 (8), 178 (11).

3-Methylthio-2,4-diazabicyclo[4.2.0]octa-1(6),2-dien-5-one (see formula 3g). In 50 mL of dry reaction flask methyl 2-chloro-2-cyclopropylidineacetate (365 mg, 2.50 mmol), S-methylisothiourea hemisulphate (see formula 2g) (1.392 g, 5.00 mmol) and triethylamine (1.52 g, 15.0 mmol) in 25 mL of anhydrous dioxane are stirred at 50° C. for 48 h. After filtration, the solid residue is suspended in DCM (25 mL) and washed with water. The aq. layer is extracted with DCM (2×25 mL). After removing the solvent in vacuum, the crude product is subjected to column chromatography (R$_f$=0.3, DCM/MeOH=25:1, 1.5×30 cm, 30 g SiO$_2$) to yield 310 mg (74%) of the compound of formula 3g as a white solid, m.p. 215° C. —IR (KBr): nu(tilde)=2996 cm$^{-1}$, 2928, 1654, 1541, 1456, 1396, 1297, 1189, 922, 751. —$^1$H NMR (250 MHz, CDCl$_3$): δ=2.58 (s, 3H, SMe), 2.95 (t, J=3.1 Hz, 2H, CH$_2$), 3.15 (t, J=3.1 Hz, 2H, CH$_2$), 11.5 (br. s, 1H, NH). —$^{13}$C NMR (62.9 MHz, [D$_6$]DMSO): 13.4 (+), 24.9 (−), 33.2 (+), 120.4 (C-6), 152.3 (C-1/C-3), 156.6 (C-3/C-1), 164.98 (C-5). —MS (70 eV), m/z (%): 169 (12) [M$^+$+1], 168 (100) [M$^+$], 121 (14) [M$^+$−SMe], 93 (22), 74 (16). —C$_7$H$_8$N$_2$OS (168.2): calcd. C, 49.98; H, 4.79; N, 16.65. found C, 49.66; H, 5.14; N, 16.50.

General Procedure 2 (GP-2)

6-Benzenesulfonyl-5,6,7,8-tetrahydroquinazolin-4(3H)-one (see formula 5): In a sealed Pyrex tube, 1 equiv. of 2,4-diazabicyclo[4.2.0]octa-1(6),2-dien-5-ones are stirred with 4 equiv. of phenyl vinyl sulfone at 175° C. for 12 h. The mixture is allowed to cool down to room temperature, dissolved in DCM/MeOH (10:1) and is subjected to column chromatography.

6-Benzenesulfonyl-2-phenyl-5,6,7,8-tetrahydroquinazolin-4(3H)-one (see formula 5a): The crude product obtained from 3-phenyl-2,4-diazabicyclo[4.2.0]octa-1(6),2-diene-5-one (see formula 3a, 198 mg, 1.00 mmol) and phenyl vinyl sulfone (670 mg, 4.00 mmol) according to GP-2 is subjected to column chromatography (R$_f$=0.41, Et$_2$O/MeOH=25:1, 1×30 cm, 25 g SiO$_2$) to yield 303 mg (81%) of the compound of formula 4b as a white solid, m.p.>250° C. —IR (KBr): nu(tilde)=2931 cm$^{-1}$, 1637, 1551, 1316, 1146, 1085, 699. —$^1$H NMR (200 MHz, [D$_6$]DMSO): δ=1.60-1.83 (m, 1H), 2.10-2.30 (m, 1H), 2.30-2.45 (m, 1H), 2.65-2.82 (m, 3H), 3.6-3.8 [m, 1H, C(6)-H], 7.4-7.6 (m, 3H), 7.60-7.85 (m, 3H), 7.85-8.10 (m, 4H), 12.6 (br. s, 1H, NH). —$^{13}$C NMR (50.3 MHz, [D$_6$]DMSO): δ=21.1 (−), 21.7 (−), 29.8 (−), 57.4 (+, C-6), 115.9 (C-4a), 127.5 (+), 128.5 (+), 128.5 (+), 129.5 (+), 131.3 (+), 132.2 (C$_{ipso}$), 134.1 (+), 136.9 (C$_{ipso}$), 153.9 (C-8a), 159.0 (C-2/C-4), 162.5 (C-4/C-2). —MS (70 eV), m/z (%): 366 (2) [M$^+$], 225 (24) [M$^+$−SO$_2$Ph], 224 (100) [M$^+$−SO$_2$Ph−H], 180 (8), 104 (12), 77 (18) [Ph$^+$]. —C$_{20}$H$_{18}$N$_2$O$_3$S (366.5): calcd. C, 65.56; H, 4.95; N, 7.64. found C, 65.89; H, 4.86; N, 7.49.

6-Benzenesulfonyl-2-(p-chlorophenyl)-5,6,7,8-tetrahydroquinazolin-4(3H)-one (see formula 5b): The crude product obtained from 3-(p-chlorophenyl)-2,4-diazabicyclo[4.2.0]octa-1(6),2-diene-5-one (see formula 3b, 400 mg, 1.70 mmol) and phenyl vinyl sulfone (1.15 g, 6.80 mmol) according to GP-2 is subjected to column chromatography (R$_f$=0.41, DCM/MeOH=25:1, 3×30 cm, 50 g SiO$_2$) to yield 410 mg (59%) of the compound of formula 4b as a white solid, m.p.>250° C. —IR (KBr): nu(tilde)=3067 cm$^{-1}$, 2946, 1655, 1548, 1506, 1321, 1146, 1087, 842, 749, 689. —$^1$H NMR (250 MHz, [D$_6$]DMSO): δ=1.68-1.80 (m, 1H), 2.20-2.75 (m, 5H), 3.60-3.71 [m, 1H, C(6)-H], 7.52-7.62 (m, 2H), 7.71-7.80 (m, 3H), 7.85-7.97 (m, 2H), 8.02-8.11 (m, 2H). —$^{13}$C NMR (63.9 MHz, [D$_6$]DMSO): δ=21.5 (−), 22.0 (−), 30.0 (−), 57.5 (+, C-6), 117.0 (C-4a), 128.8 (+), 128.9 (+), 129.5 (+), 129.8 (+), 131.0 (C—Cl), 134.4 (+), 136.6 (C$_{ipso}$), 137.1 (C$_{ipso}$), 153.1 (C-8a), 159.6 (C-2/C-4), 162.5 (C-4/C-2). —MS (70 eV), m/z (%): 400 (1) [M$^+$], 261/259 (10/36) [M$^+$−SO$_2$Ph], 260/258 (32/100) [M$^+$−HSO$_2$Ph], 140/138 (5/13) [HN=CC$_6$H$_4$Cl$^+$].

6-Benzenesulfonyl-2-(o-bromophenyl)-5,6,7,8-tetrahydroquinazolin-4(3H)-one (see formula 5c): The crude product obtained from 3-(o-bromophenyl)-2,4-diazabicyclo[4.2.0]octa-1(6),2-dien-5-one (see formula 3c, 1.10 g, 3.60 mmol) and phenyl vinyl sulfone (2.32 g, 12.0 mmol), according to GP-2 is subjected to column chromatography (R$_f$=0.43, Et$_2$O/MeOH=25:1, 3×30 cm, 50 g SiO$_2$) to yield 683 mg (43%) of the compound of formula 5c as a white solid, m.p. 221-222° C. —IR (KBr): nu(tilde)=3064 cm$^{-1}$, 2932, 1653, 1604, 1544, 1447, 1301, 1147, 1084, 764, 690. —$^1$H NMR (300 MHz, CDCl$_3$): δ=1.80-2.01 (m, 1H), 2.42-3.01 [m, 1H, C(6)-H], 7.35-7.45 (m, 2H), 7.53-7.75 (m, 5H), 7.95-8.01 (m, 2H), 11.04 (br. s, 1H, NH). —$^{13}$C NMR (50.3 MHz, CDCl$_3$): δ=21.5 (−), 22.1 (−), 30.6 (−), 58.6 (+, C-6), 117.6 (C-4a), 120.9 (C—Br), 127.8 (+), 129.0 (+), 129.3 (+), 130.9 (+), 132.1 (+), 133.6 (+), 134.0 (+), 134.6 (C$_{ipso}$), 136.8 (C$_{ipso}$), 154.3 (C-8a), 160.3 (C-2/C-4), 162.4 (C-4/C-2). —MS (70 eV), m/z (%): 446/444 (1/1) [M$^+$], 318/316 (9/10), 304/302 (95/100) [M$^+$−HSO$_2$Ph], 260/258 (11/11) 141 (18) [PhSO$_2$$^+$], 77 (52) [Ph$^+$]. —C$_{20}$H$_{17}$BrN$_2$O$_3$S (445.3): calcd. C, 53.93; H, 3.85; N, 6.29. found C, 54.22; H, 3.71; N, 6.34.

6-Benzenesulfonyl-2-(o-fluorophenyl)-5,6,7,8-tetrahydroquinazolin-4(3H)-one (see formula 5d): The crude product obtained from 3-(o-fluorophenyl)-2,4-diazabicyclo[4.2.0]octa-1(6),2-dien-5-one (see formula 3d, 648 mg, 3 mmol) and phenyl vinyl sulfone (2.01 g, 12.0 mmol), according to GP-2 is subjected to column chromatography (R$_f$=0.45, Et$_2$O/MeOH=25:1, 3×30 cm, 50 g SiO$_2$) to yield 881 mg (70%) of the compound of formula 5d as a white solid, m.p. 201-202° C. —IR (KBr): nu(tilde)=3073 cm$^{-1}$, 2941, 1672, 1603, 1558, 1449, 1308, 1146, 1084, 779, 689. —$^1$H NMR (200 MHz, CDCl$_3$): δ=1.81-2.12 (m, 1H), 2.48-3.11 (m, 5H), 3.22-3.40 [m, 1H, C(6)-H], 7.10-7.38 (m, 3H), 7.50-7.81 (m, 4H), 7.95-8.20 (m, 2H), 10.67 (br. s, 1H, NH). —$^{13}$C NMR (50.3 MHz, CDCl$_3$): δ=21.4 (−), 22.3 (−), 30.7 (−), 59.0 (+), 116.6 (+, d, $^2$J$_{C-F}$=22.9 Hz), 117.7 (C-4a), 119.4 (d, $^2$J$_{C-F}$=9.2 Hz, C$_{ipso}$), 125.1 (+, d, $^3$J$_{C-F}$=3.1 Hz), 129.0 (+), 129.3 (+), 131.0 (+, d, $^4$J$_{C-F}$=1.1 Hz), 133.7 (+, d, $^3$J$_{C-F}$=9.2 Hz), 133.9 (+), 136.8 (C$_{ipso}$), 150.5 (d, $^3$J$_{C-F}$=1.5 Hz), 160.1 (C-2), 160.5 (d, $^1$J$_{C-F}$=250.6 Hz, C—F), 163.0 (C-4). —MS (70 eV), m/z (%): 384 (1) [M$^+$], 243 (23) [M$^+$−SO$_2$Ph], 242 (100) [M$^+$−HSO$_2$Ph], 122 (16), 77 (22) [Ph$^+$]. —C$_{20}$H$_{10}$FN$_2$O$_3$S (384.4): calcd. C, 62.49; H, 4.46; N, 7.29. found C, 62.30; H, 4.30; N, 7.11.

6-Benzenesulfonyl-2-[(p-benzyloxy)phenyl]-5,6,7,8-tetrahydroquinazolin-4(3H)one (see formula 5e): The crude product obtained from 3-(p-benzyloxyphenyl)-2,4-diazabicyclo[4.2.0]octa-1(6),2-dien-5-one (see formula 3e, 652 mg, 2.1 mmol) and phenyl vinyl sulfone (2.43 g, 8.50 mmol), according to GP-2 is subjected to column chromatography (R$_f$=0.40, DCM/MeOH=25:1, 3×30 cm, 50 g SiO$_2$) to yield 670 mg (66%) of the compound of formula 5e as a white solid, m.p.>250° C. —IR (KBr): nu(tilde)=3072 cm$^{-1}$, 2939, 1649, 1607, 1547, 1516, 1304, 1259, 1144, 1085, 837, 742, 687. —$^1$H NMR (300 MHz, [D$_6$]DMSO): δ=1.71-1.84 (m, 1H), 2.18-2.31 (m, 1H), 2.40-2.58 (m, 1H), 2.64-2.78 (m, 3H), 3.55-3.73 [m, 1H, C(6)-H], 5.21 (s, 2H), 7.05-7.12 (m, 2H), 7.31-7.48 (m, 5H), 7.64-7.8 (m, 3H), 7.90-7.98 (m, 2H), 8.04-8.11 (m, 2H), 12.15 (br. s, 1H, NH). —$^{13}$C NMR (50.3 MHz, [D$_6$]DMSO): δ=21.1 (−), 22.0 (−), 29.7 (−), 57.4 (+), 69.3 (−), 114.7 (+), 114.9 (C-4a), 124.3 (C$_{ipso}$), 127.6 (+), 127.8 (+), 128.4 (+), 128.4 (+), 129.2 (+), 129.5 (+), 134.0 (+), 136.5 (C$_{ipso}$), 136.9 (C$_{ipso}$), 153.8 (C-8a), 160.8 (C-2/C-4), 162.5, (C-4/C-2). —MS (70 eV), m/z (%): 472 (2) [M$^+$], 330

(49) [M$^+$–SO$_2$Ph], 91 (100) [C$_7$H$_7^+$]. —C$_{27}$H$_{24}$N$_2$O$_4$S (472.6): calcd. C, 68.63; H, 5.12; N, 5.93. found C, 68.80; H, 5.04; N, 6.08.

6-Benzenesulfonyl-2-(o-biphenyl)-6,6,7,8-tetrahydroquinazolin-4(3)-one (see formula 5f): The crude product obtained from 3-(o-biphenyl)-2,4-diazabicyclo[4.2.0]octa-1(6),2-dien-5-one (see formula 3f, 501 mg, 1.83 mmol) and phenyl vinyl sulfone (1.23 g, 7.32 mmol), according to GP-2 is subjected to column chromatography (R$_f$=0.31, Et$_2$O/MeOH=25:1, 3×30 cm, 50 g SiO$_2$) to yield 522 mg (65%) of the compound of formula 5f as a white solid, m.p. 194-195° C. —IR (KBr): nu(tilde)=3059 cm$^{-1}$, 3059, 2933, 1647, 1546, 1447, 1320, 1302, 1145, 1085, 742, 688. —$^1$H NMR (250 MHz, CDCl$_3$): δ=1.82-1.95 (m, 1H), 2.42-2.95 (m, 5H), 3.21-3.31 [m, 1H, C(6)-H], 7.20-7.39 (m, 5H), 7.42-7.78 (m, 7H), 7.90-8.02 (m, 2H), 9.1 (br. s, 1H, NH). —$^{13}$C NMR (62.9 MHz, CDCl$_3$): δ=21.3 (–), 22.1 (–), 30.5 (–), 59.1 (+), 116.5 (C-4a), 127.7 (+), 128.1 (+), 128.4 (+), 128.9 (+), 129.0 (+), 130.0 (+), 130.9 (+), 131.0 (+), 131.7 (+), 133.9 (C$_{ipso}$) 136.9 (C$_{ipso}$) 139.2 (C$_{ipso}$) 140.7 (C$_{ipso}$), 155.7 (C-8a), 160.1 (C-2/C-4), 162.0 (C-4/C-2). —MS (70 eV), m/z (%): 442 (4) [M$^+$], 300 (100) [M$^+$–SO$_2$Ph], 180 (16), 122 (17). —C$_{26}$H$_{22}$N$_2$O$_3$S (442.5): calcd. C, 70.57; H, 5.01; N, 6.33. found C, 70.53; H, 4.98; N, 6.04.

6-Benzenesulfonyl-2-(methylthio)-5,6,7,8-tetrahydroquinazolin-4(3H)-one (see formula 5g): The crude product obtained from the compound of formula 3g (168 mg, 1.00 mmol) and phenyl vinyl sulfone (672 g, 7.32 mmol), according to GP-2 is subjected to column chromatography (R$_f$=0.41, DCM/MeOH=25:1, 1.5×20 cm, 25 g SiO$_2$) to yield 189 mg (56%) of the compound of formula 5f as a white solid, m.p.>250° C. —IR (KBr): nu(tilde)=3059 cm$^{-1}$, 2918, 2847, 1644, 1576, 1448, 1315, 1150, 1088, 723, 689. —$^1$H NMR (200 MHz, [D$_6$]DMSO): δ=1.57-1.79 (m, 1H), 2.11-2.38 (m, 3H), 2.43 (s, 3H), 2.58-2.70 (m, 2H), 3.52-3.73 [m, 1H, C(6)-H], 7.60-7.81 (m, 3H), 7.85-7.95 (m, 2H), 12.56 (br. s, 1H, NH). —$^{13}$C NMR (50.3 MHz, [D$_6$]DMSO): δ=12.5 (+), 21.0 (–), 21.4 (–), 29.8 (–), 57.3 (+), 117.2 (C-4a), 128.4 (+), 129.5 (+), 134.0 (+), 136.9 (C$_{ipso}$) 154.3 (C-8a), 159.8 (C-2/C-4), 162.7 (C-4/C-2). —MS (70 eV), m/z (%): 336 (2) [M], 195 (18), 194 (100) [M$^+$–SO$_2$Ph]. —C$_{15}$H$_{16}$N$_2$O$_3$S$_2$ (336.4): calcd. C, 53.57; H, 4.79; N, 8.33. found C, 53.56; H, 4.52; N, 8.20.

General Procedure 3 (GP-3)

2-Aryl-7,8-dihydroquinazolin-4(3H)-one (see formula 6): To a suspension of sulfone of formula 5 in THF, 3 equiv. of KOtBu are added and the resulting solution is stirred for 2 h at room temperature, poured into a separating funnel with sat. aq. NH$_4$Cl solution (10 mL) and extracted with DCM (3×20 mL). The organic layer is dried over MgSO$_4$, solvent is evaporated in vacuum to yield the compound of formula 6 which is used for the next reaction without further purification.

2-Phenyl-7,8-dihydroquinazolin-4(3H)-one (see formula 6a): From the sulfone of formula 5a (366 mg, 1.00 mmol) and KOtBu (336 mg, 3.00 mmol) is obtained according to GP-3 210 mg (96%) of the compound of formula 6a as a pale yellow solid, m.p. 241° C., R$_f$=0.5 (hexane/ethylacetate=1:1). —IR (KBr): nu(tilde)=3032 cm$^{-1}$, 2932, 1653, 1505, 1317, 930, 718. —$^1$H NMR (250 MHz, CDCl$_3$): δ=2.42-2.58 [m, 2H, C(7)-H], 2.89 [t, J=9.6 Hz, 2H, C(8)-H], 6.04 [dt, J=9.7 and 4.3 Hz, 1H, C(6)-H], 6.73 [dt, J=9.7 and 1.8 Hz, 1H, C(5)-H], 7.48-7.56 (m, 3H), 8.14-8.22 (m, 2H), 12.58 (br. s, 1H, NH). —$^{13}$C NMR (62.9 MHz, CDCl$_3$): δ=22.7 (–), 29.6 (–), 117.2 (C-4a), 119.5 (+, C-5), 127.4 (+), 127.6 (+), 128.9 (+), 131.7 (+, C-6), 132.1 (C$_{ipso}$), 154.6 (C-8a), 161.4 (C-2/C-4), 161.9 (C-4/C-2). —MS (70 eV), m/z (%): 224 (100) [M$^+$], 223 (98), 180 (19) [M$^+$–CONH$_2$], 104 (14) [PhCNH$^+$], 77 (20) [Ph$^+$]. —C$_{14}$H$_{12}$N$_2$O (224.3): calcd. C, 74.98; H, 5.39; N, 12.55. found C, 74.71; H, 5.31; N, 12.31.

2-(p-Chlorophenyl)-7,8-dihydroquinazolin-4(3H)-one (see formula 6b): From the sulfone of formula 5b (200 mg, 0.50 mmol) and KOtBu (168 mg, 1.50 mmol) is obtained according to GP-3 123 mg (95%) of the compound of formula 6b as a pale yellow solid, m.p.>250° C., R$_f$=0.48 (hexane/ethylacetate=1:1). —IR (KBr): nu(tilde)=3029 cm$^{-1}$, 2934, 1652, 1504, 1389, 1176, 1091, 738. —$^1$H NMR (250 MHz, CDCl$_3$): δ=2.42-2.56 [m, 2H, C(7)-H], 2.87 [t, J=9.6 Hz, 2H, C(8)-H], 6.06 [dt, J=9.5 and 4.3 Hz, 1H, C(6)-H], 6.71 [dt, J 9.5 and 1.8 Hz, 1H, C(5)-H], 7.48-7.56 (m, 2H), 8.16-8.27 (m, 2H), 13.1 (br. s, 1H, NH). —$^{13}$C NMR (62.9 MHz, CDCl$_3$): δ=22.3 (–), 28.7 (–), 116.8 (C-4a), 119.6 (+, C-5), 127.7 (+), 128.9 (+), 129.5 (+), 131.7 (+, C-6), 136.5 (C$_{ipso}$), 153.3 (C-8a), 159.6 (C-2/C-4), 162.5 (C-4/C-2). —MS (70 eV) m/z (%): 260/258 (32/100) [M$^+$], 259/257 (40/98) [M$^+$–H], 216/214 (28/8), 104 (14), 77 (20) [Ph$^+$]. —C$_{14}$H$_{11}$ClN$_2$O (258.7): calcd. C, 65.00; H, 4.29; N, 10.83. found C, 64.93; H, 4.08; N, 10.99.

2-(o-Bromophenyl)-7,8-dihydroquinazolin-4(3H)-one (see formula 6c): From the sulfone of formula 5c (400 mg, 0.90 mmol) and KOtBu (302 mg, 2.70 mmol) is obtained according to GP-3 285 mg (94%) of the compound of formula 6c as a pale yellow solid, m.p. 202° C., R$_f$=0.55 (Et$_2$O). —IR (KBr): nu(tilde)=3035 cm$^{-1}$, 2836, 1665, 1491, 1324, 1183, 928, 767, 735. —$^1$H NMR (200 MHz, CDCl$_3$): δ=2.15-2.30 [m, 2H, C(7)-H], 2.85 [t, J=9.1 Hz, 2H, C(8)-H], 6.04 [dt, J=9.6 and 4.4 Hz, 1H, C(6)-H], 6.59 [dt, J=9.6 and 1.7 Hz, 1H, C(5)-H], 7.28-7.81 (m, 4H), 11.55 (br. s, 1H, N—H). —$^{13}$C NMR (50.3 MHz, CDCl$_3$): δ=22.5 (–), 29.0 (–), 118.0 (C-8a), 119.3 (+, C-5), 121.1 (C—Br), 127.7 (+, C-6), 127.9 (+), 131.1 (+), 131.8 (+), 133.7 (+), 134.3 (C$_{ipso}$) 154.4 (C-8a), 160.6 (C-2/C-4), 160.6 (C-4/C-2). —MS (70 eV), m/z (%): 304/302 (96/100) [M$^+$], 203/301 (98/80), 259/257 (24/26), 102 (28). —C$_{14}$H$_{11}$BrN$_2$O (303.2): calcd. C, 55.47; H, 3.66; N, 9.24. found C, 55.22; H, 3.70; N, 9.03.

2-(o-Fluorophenyl)-7,8-dihydroquinazolin-4(3H)-one (see formula 6d): From the sulfone of formula 5d (384 mg, 1.00 mmol) and KOtBu (336 mg, 3.00 mmol) is obtained according to GP-3 223 mg (92%) of the compound of formula 6d as a pale yellow solid, m.p. 191° C., R$_f$=0.51 (Et$_2$O). —IR (KBr): nu(tilde)=3043 cm$^{-1}$, 2934, 2886, 1653, 1559, 1327, 1220, 1181, 1122, 774. —$^1$H NMR (250 MHz, CDCl$_3$): δ=2.38-2.52 [m, 2H, C(7)-H], 2.85 [t, J=9.3 Hz, 2H, C(8)-H], 5.98 [dt, $^3$J=9.5 and 4.4 Hz, 1H, C(6)-H], 6.61 [dt, J=9.5 and 1.7 Hz, 1H, C(5)-H], 7.12-7.35 (m, 2H), 7.41-7.54 (m, 1H), 7.98-8.12 (m, 1H), 11.51 (br. s, 1H, NH). —$^{13}$C NMR (62.9 MHz, CDCl$_3$): δ 22.5 (–), 29.0 (–), 116.5 (+, d, $^2$J$_{C-F}$=22.7 Hz), 118.0 (C-4a), 119.4 (+, C-5), 120.1 (C$_{quat}$, d, $^2$J$_{C-F}$=9.0 Hz), 124.8 (+, d, $^3$J$_{C-F}$=3.1 Hz), 127.8 (+, C-6), 130.9 (+), 133.3 (+, d, $^3$J$_{C-F}$=9.2 Hz), 134.5 (C$_{ipso}$), 155.3 (C$_{quat}$, d, $^1$J$_{C-F}$=250.6 Hz), 157.5 (C-8a), 158.4 (C-2/C-4), 162.4 (C-4/C-2). —MS (70 eV), m/z (%): 242 (100) [M$^+$], 241 (85), 198 (24), 102 (12). —C$_{14}$H$_{11}$FN$_2$O (242.3): calcd. C, 69.41; H, 4.58; N, 11.56. found C, 69.22; H, 4.83; N, 11.45.

2-(p-Benzoyloxyphenyl)-7,8-dihydroquinazolin-4(3H)-one (see formula 6e): From the sulfone of 5d (400 mg, 0.85 mmol) and KOtBu (285 mg, 2.50 mmol) is obtained according to GP-3 258 mg (92%) of the compound of formula 6e as a pale yellow solid, m.p. 247° C., R$_f$=0.62 (CH$_2$Cl$_2$/MeOH=25/1). —IR (KBr): nu(tilde)=3032 cm$^{-1}$, 2943, 1646, 1606, 1512, 1305, 999, 753, 677. —$^1$H NMR (250 MHz, CDCl$_3$): δ=2.40-2.58 (m, 2H), 2.85 [t, J=9.1 Hz, 2H, C(8)-H], 5.15 (s, 2H), 6.01 [dt, J=9.6 and 4.4 Hz, 1H, C(6)-H], 6.7 [dt, J=9.6 and 1.7 Hz, 1H, C(5)-H], 7.02-7.18 (m, 2H), 7.30-7.62 (m, 5H), 8.06-8.22 (m, 2H), 12.23 (br. s, 1H, NH). —$^{13}$C NMR (75.5 MHz, CDCl$_3$): δ=22.7 (–), 28.6 (–), 69.4 (–), 114.8 (C-4a), 119.5 (+, C-5), 126.34 (+, C-6), 127.7 (+), 127.9 (+), 128.4 (+), 129.2 (+), 131.5 (C$_{ipso}$), 136.5 (C$_{ipso}$), 140.8 (C$_{ipso}$), 155.9 (C-8a), 159.9 (C-2/C-4), 160.9 (C-4/C-2). —MS (70 eV), m/z (%): 330 (55) [M$^+$], 239 (8), 91 (100) [C$_7$H$_7^+$].

2-(o-Biphenyl)-7,8-dihydroquinazolin-4(3H)-one (see formula 6f): From the sulfone of formula 5f (300 mg, 0.68 mmol) and KOtBu (224 mg, 2.00 mmol) is obtained according to GP-3 177 mg (87%) of the compound of formula 6f as a pale yellow solid, m.p. 193° C., $R_f$=0.55 (Et$_2$O). —IR (KBr): nu(tilde)=3070 cm$^{-1}$, 2936, 1634, 1549, 1507, 1321, 1165, 979, 699. —$^1$H NMR (250 MHz, CDCl$_3$): δ=2.38-2.51 [m, 2H, C(7)-H], 2.88 [t, J=9.2 Hz, 2H, C(8)-H], 5.98 [dt, J=9.5 and 4.4 Hz, 1H, C(6)-H], 6.57 [dt, J=9.5 and 1.7 Hz, 1H, C(5)-H], 7.22-7.36 (m, 5H), 7.44-7.62 (m, 3H), 7.76-7.82 (m, 1H) 9.51 (br. s, 1H, NH). —$^{13}$C NMR (62.9 MHz, CDCl$_3$): δ=22.5 (–), 38.7 (–), 117.2 (C-4a), 119.3 (+, C-5), 127.8 (+, C-6), 127.9 (+), 128.6 (+), 129.1 (+), 130.2 (+), 130.9 (+), 131.1 (+), 131.5 ($C_{ipso}$), 139.1 ($C_{ipso}$), 140.8 ($C_{ipso}$), 155.8 (C-8a), 159.8 (C-2/C-4), 160.0 (C-4/C-2). —MS (70 eV), m/z (%): 301 (28) [M$^+$+1], 300 (100) [M$^+$], 299 (40), 180 (38), 122 (43), 77 (78). —C$_{14}$H$_{11}$ClN$_2$O (300.4): calcd. C, 79.98; H, 5.37; N, 9.33. found C, 79.64; H, 5.24; N, 9.57.

2-Methylthio-7,8-dihydroquinazolin-4(3H)-one (see formula 6g): From the sulfone of formula 5g (336 mg, 1.00 mmol) and KOtBu (336 mg, 3.00 mmol) is obtained according to GP-3 181 mg (98%) of the compound of formula 6g as a pale yellow solid, m.p. 214° C., $R_f$=0.45 (Et$_2$O). —IR (KBr): nu(tilde)=2922 cm$^{-1}$, 2836, 1641, 1623, 1540, 1271, 1138, 1203, 943. —$^1$H NMR (250 MHz, CDCl$_3$): δ=2.38-2.49 [m, 2H, C(7)-H], 2.60 (s, 3H), 2.76 [t, J=9.3 Hz, 2H, C(8)-H], 5.98 [dt, J=9.7 and 4.3 Hz, 1H, C(6)-H], 6.61 [dt, J=9. and 1.8 Hz, 1H, C(5)-H], 12.9 (br. s, 1H, NH). —$^{13}$C NMR (62.9 MHz, CDCl$_3$): δ=13.3 (+), 22.4 (–), 29.4 (–), 114.6 (C-4a), 119.3 (+, C-5), 126.0 (+, C-6), 157.0 (C-8a), 161.2 (C-2/C-4), 162.2 (C-4/C-2). —MS (70 eV, m/z (%): 194 (100) [M$^+$], 147 (12), 121 (16), 92 (14). —C$_9$H$_{10}$N$_2$OS (194.3): calcd. C, 55.65; H, 5.19; N, 14.42. found C, 55.39; H, 5.32; N, 14.16.

General Procedure 4 (GP-4)

2-Aryl-5,6,7,8-tetrahydroquinazolin-4(3H)-one (see formula 7): Into a 50 mL flame-dried flask flushed with nitrogen, Pd/C (10% Pd w/w) is added followed by 10 mL of MeOH. This mixture is stirred under H$_2$ for 30 min, at which point a solution of the compound of formula 6 in MeOH is added from a syringe and stirring is continued, until the reaction completes. Reaction mixture is filtered through a pad of Celite,® and solvent is removed in vacuo to yield the compound of formula 7 as a white solid.

2-Phenyl-5,6,7,8-tetrahydroquinazolin-4(3H)-one (see formula 7a): The crude reaction mixture obtained from the compound of formula 6a (224 mg, 1.00 mmol), 10 mg of Pd/C in 20 mL of MeOH after 4 h according to GP-4 affords 206 mg (91%) of the compound of formula 7a with m.p. 224° C. —IR (KBr): nu(tilde)=2934 cm$^{-1}$, 2848, 1634, 1550, 1319, 1165, 979, 698. —$^1$H NMR (250 MHz, CDCl$_3$): δ=1.75-1.91 (m, 4H), 2.50-2.65 (m, 2H), 2.71-2.78 (m, 2H), 7.40-7.58 (m, 3H), 8.11-8.22 (m, 2H), 12.38 (br. s, 1H, NH). —$^{13}$C (62.9 MHz, CDCl$_3$): δ=21.8 (–), 21.9 (–), 22.3 (–), 31.9 (–), 120.2 C-4a ( ), 127.5 (+), 128.8 (+), 131.4 (+), 132.5 ($C_{ipso}$), 153.2 (C-8a), 162.5 (C-2/C-4), 164.5 (C-4/C-2). —MS (70 eV), m/z (%): 227 (19) [M$^+$+1], 226 (100) [M$^+$], 225 (51), 211 (31), 198 (10), 104 (21). —C$_{14}$H$_{14}$N$_2$O (226.3): calcd. C, 74.31; H, 6.24; N, 12.38. found C, 74.34; H, 6.55; N, 12.29.

2-(p-Chlorophenyl)-5,6,7,8-tetrahydroquinazolin-4(3H)-one (see formula 7b): The crude reaction mixture obtained from the compound of formula 6b (51.6 mg, 0.20 mmol), 20 mg of Pd/C in 10 mL of AcOH after 8 h according to GP-4 affords 49 mg (94%) of the compound of formula 7b with solid, m.p.=255° C. —IR (KBr): nu(tilde)=3070 cm$^{-1}$, 2936, 1634, 1549, 1507, 1321, 1014, 929, 699. —$^1$H NMR (250 MHz, CDCl$_3$): δ=1.74-1.93 (m, 4H), 2.50-2.62 (m, 2H), 2.66-2.79 (m, 2H), 7.42-7.58 (m, 2H), 8.13-8.24 (m, 2H), 12.92 (br. s, 1H, NH). —$^{13}$C (62.9 MHz, CDCl$_3$): δ=21.8, (–), 21.9 (–), 22.4 (–), 32.0 (–), 120.4 (C-4a), 127.4 (+), 128.9 (+), 129.0 ($C_{ipso}$), 131.4 (C—Cl), 157.5 (C-2/C-8a), 157.6 (C-8a/C-2), 162.5 (C-4). —MS (70 eV), m/z (%): 262/260 (16/51) [M$^+$], 226 (100) [M– Cl+1], 225 (52) [M$^+$–Cl], 211 (37), 104 (32), 77 (26).

2-(o-Bromophenyl)-5,6,7,8-tetrahydroquinazolin-4(3H)-one (see formula 7c): The crude reaction mixture obtained from the compound of formula 6c (100 mg, 0.33 mmol) 20 mg of Pd/C (10% by weight) in 20 mL of MeOH after 4 h according to GP-4 is filtered through a pad of Celite® and solvent is removed in vacuo to yield 93 mg (92%) of the compound of formula 7b as a white solid, m.p. 193° C. —IR (KBr): nu(tilde)=3035 cm$^{-1}$, 2944, 1648, 1559, 1319, 1227, 1031, 977, 927, 760, 728. —$^1$H NMR (250 MHz, CDCl$_3$): δ=1.72-1.91 (m, 4H), 2.38-2.51 (m, 2H), 2.60-2.78 (m, 2H), 7.28-7.42 (m, 2H), 7.51-7.68 (m, 2H), 12.12 (br. s, 1H, NH). —$^{13}$C (62.9 MHz, CDCl$_3$): δ=21.5 (–), 21.8 (–), 22.1 (–), 31.6 (–), 121.1 (C-4a), 127.6 (+), 131.0 (+), 131.7 (+), 133.4 (+), 134.6 ($C_{ipso}$), 156.2 (C-8a), 161.8 (C-2), 163.6 (C-4). —MS (70 eV), m/z (%): 304/306 (100/95) [M$^+$], 289/291 (28/27), 225 (11) [M$^+$–Br]. —C$_{14}$H$_{13}$BrN$_2$O (305.2): calcd. C, 55.10; H, 4.29; N, 9.18. found C, 55.32; H, 4.14; N, 8.97.

2-(o-Fluorophenyl)-5,6,7,8-tetrahydroquinazolin-4(3H)-one (see formula 7d): The crude reaction mixture obtained from the compound of formula 6d (100 mg, 0.41 mmol), 20 mg of Pd/C in 20 mL of MeOH after 4 h according to GP-4 affords 93 mg (92%) of the compound of formula 7d with m.p. 170° C. —IR (KBr): nu(tilde)=3026 cm$^{-1}$, 2952, 1647, 1564, 1327, 1233, 1163, 979, 928, 761. —$^1$H NMR (250 MHz, CDCl$_3$): δ=1.66-1.92 (m, 4H), 2.49-2.61 (m, 2H), 2.63-2.74 (m, 2H), 7.16-7.34 (m, 2H), 7.22-7.58 (m, 1H), 8.14-8.25 (m, 1H), 10.2 (br. s, 1H, NH). —$^{13}$C (62.9 MHz, CDCl$_3$): δ=21.6, (–), 21.9 (–), 22.2 (–), 31.7 (–), 116.4 (+, d, $^2J_{C-F}$=22.9 Hz), 120.3 ($C_{quat}$, d, $^2J_{C-F}$=9.2 Hz), 121.2 (C-4a), 124.8 (+, d, $^3J_{C-F}$=3.1 Hz), 130.9 (+), 132.5 (+, d, $^3J_{C-F}$=9.2 Hz), 154.0 ($C_{quat}$, d, $^1J_{C-F}$=250.6 Hz), 161.5 (C-8a), 162.4 (C-2/C-4), 162.7 (C-4/C-2). —MS (70 eV), m/z (%): 244 (100) [M$^+$], 243 (48), 229 (28), 122 (16). —C$_{14}$H$_{13}$FN$_2$O (244.3): calcd. C, 68.84; H, 5.56; N, 11.47. found C, 69.09; H, 5.21; N, 11.61.

2-[(p-Benzoyloxy)phenyl]-5,6,7,8-tetrahydroquinazoline-4(3H)-one (see formula 7e): The crude reaction mixture obtained from the compound of formula 6e (165 mg, 0.50 mmol), 25 mg of Pd/C in 10 mL of AcOH after 8 h according to GP-4 affords 113 mg (93%) of the compound of formula 7e with m.p.>250° C. —IR (KBr): nu(tilde)=3430 cm$^{-1}$, 2940, 1641, 1515, 1324, 1289, 1182, 1113, 932, 847, 768. —$^1$H NMR (300 MHz, [D$_6$]DMSO): δ=1.61-1.80 (m, 4H), 2.31-2.41 (m, 2H), 2.54-2.61 (m, 2H), 6.78-6.89 (d, J=8.3 Hz, 2H), 7.88-7.99 (d, J=8.3 Hz, 2H), 10.6 (br. s, 1H, NH). —$^{13}$C (75.5 MHz, [D$_6$]DMSO): δ=21.5, (–), 21.6 (–), 21.9 (–), 31.1 (–), 115.2 (C-4a), 117.8 ($C_{quat}$), 122.8 ($C_{ipso}$), 129.1 (+), 153.0 (C-8a), 160.5 (C-2/C-4), 162.9 (C-4/C-2). —MS (70 eV), m/z (%): 242 (100) [M$^+$], 241 (44), 227 (27), 120 (31).

2-(o-Biphenyl)-5,6,7,8-tetrahydroquinazolin-4(3H)-one (see formula 7f): The crude reaction mixture obtained from the compound of formula 6f (120 mg, 0.4 mmol), 10 mg of Pd/C in 20 mL of MeOH after 4 h according to GP-4 affords 112 mg (93%) of the compound of formula 7f with m.p. 190° C. —IR (KBr): nu(tilde)=3027 cm$^{-1}$, 2936, 1643, 1566, 1324, 1225, 1170, 978, 764. —$^1$H NMR (250 MHz, CDCl$_3$): δ=1.66-1.84 (m, 4H), 2.38-2.48 (m, 2H), 2.57-2.66 (m, 2H), 7.21-7.42 (m, 5H), 7.48-7.61 (m, 2H), 7.72-7.79 (m, 2H), 11.1 (br. s, 1H, NH). —$^{13}$C (62.9 MHz, CDCl$_3$): δ=21.6 (–), 21.7 (–), 22.1 (–), 31.6 (–), 119.9 (C-4a), 127.3 (+), 127.4 (+), 128.1 (+), 128.3 (+), 129.0 (+), 130.0 (+), 130.7 (+), 132.1 ($C_{ipso}$), 139.5 (+), 140.7 ($C_{ipso}$), 156.1 (C-8a), 161.5 (C-2/C-4), 163.3 (C-4/C-2). —MS (70 eV), m/z (%): 302 (72) [M$^+$], 301 (35), 180 (58), 124 (100). —C$_{22}$H$_{18}$N$_2$O (302.4): calcd. C, 79.44; H, 6.00; N, 9.26. found C, 79.89; H, 5.68; N, 9.49.

One Pot Synthesis

One pot synthesis of 6-benzenesulfonyl-2-phenyltetrahydroquinazolin-4(3H)-one (see formula 5a): Into a 10 mL pyrex bottle methyl 2-chloro-2-cyclopropylidine acetate (see formula I) (147 mg, 1 mmol), benzamidine hydrochloride (see formula 2a) (313 mg, 2 mmol) and triethylamine (405 mg, 4 mmol) are loaded and stirred in 5 mL of dioxane at RT for 2 d, at which point phenyl vinyl sulfone (672 mg, 4 mmol) is added, the bottle is sealed and heated at 175° C. for 15 h. After cooling, solvent is removed from the reaction mixture, and it is subjected to column chromatography (hexane/ethylacetate=1:2), to yield 157 mg (43%) of the compound of formula 5a as a white solid. Using the same method as above, 177 mg (46%) of the compound of formula 5d is obtained from 1 (147 mg, 1 mmol), o-fluorobenzamidine hydrochloride (see formula 2d) (349 mg, 2 mmol), triethylamine (405 mg, 4 mmol) and phenyl vinyl sulfone (672 mg, 4 mmol).

6-Benzenesulfonyl-4-oxo-2-phenyl-5,6,7,8-tetrahydroquinazoline-4(H)-3-carboxylic acid tert-butyl ester (see formula 5a-Boc): To a suspension of the compound of formula 5a (183.2 mg, 0.50 mmol) in 10 mL of THF is added (Boc)$_2$O (218.3 mg, 1.0 mmol), Et$_3$N (50.6 mg, 0.5 mm0l) and DMAP (122.2 mg, 0.5 mmol) at room temperature, and the resulting solution is stirred for 2 h. The reaction mixture is diluted with 25 mL of DCM and washed with 10 mL 1 N HCl. Organic layer is separated, aqueous layer extracted with DCM (2×20 mL). The combined organic layers are dried over MgSO$_4$, solvent removed and the crude product is purified by column chromatography (R$_f$=0.5, hexane/EE=2:1, 1×20 cm, "flash" SiO$_2$) to yield 191 mg (82%) of the product as a white solid with m.p. 153° C. —IR (KBr): nu(tilde)=3066 cm$^{-1}$, 2985, 1752, 1595, 1421, 1249, 1146. —$^1$H NMR (250 MHz, CDCl$_3$): δ=1.62 (s, 9H), 1.84-2.04 (m, 1H), 2.40-2.56 (m, 1H), 2.79-3.25 (m, 4H), 3.31-3.44 [m, 1H, C(6)-H], 7.42-7.51 (m, 3H), 7.58-7.78 (m, 3H), 7.95-8.02 (m, 3H), 8.28-8.39 (m, 2H). —$^{13}$C NMR (62.9 MHz, CDCl$_3$): δ=21.8 (−), 22.0 (−), 27.5 (+), 31.0 (−), 58.9 (+), 85.2 (C$_{quat}$), 114.5 (C-4a), 128.2 (+), 128.4 (+), 129.0 (+), 129.4 (+), 130.6 (+), 134.2 (C$_{ipso}$), 136.4 (+), 136.5 (C$_{ipso}$), 148.9 (C-8a), 162.6 (C-2/C-4), 163.4 (C-4/C-2) 167.0 (C=O). —MS (70 eV), m/z (%): 466 (1) [M$^+$], 225 (20), 224 (100) [M$^+$−SO$_2$Ph−Boc−H], 57 (16).

6-Benzenesulfonyl-8-methyl-4-oxo-2-phenyl-5,6,7,8-tetrahydroquinazoline-4(H)-3-carboxylic acid tert-butyl ester (see formula 8): To a solution of the compound of formula 5a-Boc (233 mg, 0.5 mmol) in 10 mL of THF is added nBuLi (0.24 mL, 2.45 M in hexane) at −78° C. over a period of 15 min. A dark red solution is stirred at this temp. for 15 min, at which point MeI (92.3 mg, 0.65 mmol) in 1 ml of THF is added, cooling bath was removed, and stirring is continued at room temperature for 2 h. The reaction mixture is poured into a separating funnel containing 10 mL of sat. aq. NH$_4$Cl solution and extracted with Et$_2$O (3×15 mL). Combined organic solutions are dried over MgSO$_4$. Removal of solvent followed by column chromatography (R$_f$=0.55, hexane/EE=2:1, 1×20 cm, "flash" SiO$_2$) yields 66 mg (28%) of the title product as a white solid, m.p. 98° C. —IR (KBr): nu(tilde)=3029 cm$^{-1}$, 2981, 1762, 1540, 1410, 1243, 1148, 856. —$^1$H NMR (300 MHz, CDCl$_3$): δ=1.35 (d, J=7.3 Hz, 3H), 1.58 (s, 9H) 2.04-2.32 (m, 2H), 2.75-3.12 (m, 2H), 3.25-3.39 (m, 1H), 3.40-3.52 [m, 1H, C(6)-H], 7.38-7.46 (m, 3H), 7.58-7.77 (m, 3H), 7.92-7.98 (m, 2H), 8.30-8.39 (m, 2H). —$^{13}$C NMR (50.3 MHz, CDCl$_3$): δ=21.6 (+), 22.2 (−), 27.9 (+), 28.4 (−), 34.8 (+), 55.8 (+), 85.4 (C$_{quat}$), 114.0 (C-4a), 128.1 (+), 128.3 (+), 129.1 (+), 129.5 (+), 131.2 (+), 134.2 (+), 136.4 (C$_{ipso}$), 149.2 (C-8a), 162.5 (C-2/C-4), 163.4 (C-4/C-2) 171.4 (C=O). —MS (DCI, 70 eV), m/z (%): 498 (5) [M$^+$+NH$_4$], 481 (100) [M$^+$+H], 381 (79), 341 (82).

6-Benzenesulfonyl-2-phenyl-4-trimethylsilyloxy-5,6,7,8-tetrahydroquinazolin (see formula 5a-TMS): Into a 25 mL dry reaction flask the compound of formula 5f (1.6 g, 4.4 mmol) is added in 15 ml of HMDS along with 20 mg of (NH$_4$)$_2$SO$_4$. This reaction mixture is refluxed for 15 h. After cooling HMDS is removed in vacuo, the reaction mixture is diluted with 20 mL of dichloromethane, washed with 5 mL of water and dried over MgSO$_4$. Removal of the solvent yields 1.91 g (99%) of the compound of formula 8 as a white solid, m.p.>250° C. —$^1$H NMR (250 MHz, CDCl$_3$): δ=0.45 (s, 9H), 1.80-1.98 (m, 1H), 2.35-2.51 (m, 1H), 2.75-2.87 (m, 2H), 3.02-3.21 (m, 2H), 3.25-3.41 (m, 1H), 7.18-7.32 (m, 3H), 7.58-7.75 (m, 3H), 7.95-8.03 (m, 2H), 8.25-8.36 (m, 2H). —$^{13}$C (62.9 MHz, CDCl$_3$): δ=0.31 (+), 21.86 (−), 22.23 (−), 30.81 (−), 59.5 (+), 112.3 (C-4a), 127.3 (+), 127.8 (+), 128.4 (+), 128.9 (+), 129.0 (+), 130.2 (+), 134.0 (+), 136.8 (C$_{ipso}$), 137.5 (C$_{ipso}$) 161.4 (C-8a), 164.1 (C-2/C-4), 166.4 (C-4/C-2). —MS (70 eV), m/z (%): 438 (2) [M$^+$], 296 (100) [M$^+$−SO$_2$Ph], 281 (23) [M$^+$−SO$_2$Ph−Me], 247 (63), 175 (25).

6-Benzenesulfonyl-6-methyl-2-phenyl-5,6,7,8-tetrahydroquinazolin-4(3H)-one (see formula 9a): To a cooled solution of sulfone of formula 8 (439 mg, 1 mmol) in 15 mL of THF, nBuLi (1.77 M in Hexane, 0.62 mL) is added at −78° C. over a period of 15 min. The resulting mixture is stirred for additional 15 min. at which point CH$_3$I (156 mg, 1.1 mmol) in 1 ml of THF is added, cooling bath is removed, and stirring is continued at RT for 2 h. The reaction mixture is poured into a separating funnel containing 10 mL of sat. aq. NH$_4$Cl solution and extracted with DCM (3×15 mL). Removal of solvent followed by column chromatography (R$_f$=0.32, DCM/MeOH=25:1, 1.5×30 cm, 25 g SiO$_2$) yields 315 mg (83%) of the compound of formula 9a as a white solid, m.p.>250° C. —IR (KBr): nu(tilde)=3057 cm$^{-1}$, 2943, 1644, 1553, 1447, 1300, 1153, 1088, 701. —$^1$H NMR (250 MHz, [D$_6$]DMSO): δ=1.22 (s, 3H), 1.84-2.51 (m, 2H), 2.62-2.83 (m, 3H), 7.38-7.60 (m, 3H), 7.63-8.10 (m, 7H). —$^{13}$C NMR (62.9 MHz, [D$_6$]DMSO): δ=18.1 (+), 26.2 (−), 27.8 (−), 28.1 (−), 60.4 (C$_{quat}$), 115.7 (C-4a), 127.8 (+), 128.8 (+), 129.6 (+), 130.5 (+), 132.4 (+), 134.6 (C$_{ipso}$), 154.1 (C-8a), 158.4 (C-2), 164.2 (C-4). —MS (70 eV), m/z (%): 380 (1) [M$^+$], 238 (100) [M$^+$−SO$_2$Ph], 77 (30). —C$_{21}$H$_{20}$N$_2$O$_3$S (380.5): calcd. C, 66.30; H, 5.30; N, 7.36. found C, 66.13; H, 5.60; N, 7.61.

6-Benzenesulfonyl-6-ethyl-2-phenyl-5,6,7,8-tetrahydroquinazolin-4(3H)-one (see formula 9b): The crude mixture obtained from the compound of formula 8 (439 mg, 1 mmol), nBuLi (1.77 M, 0.62 mL) and EtBr (119 mg, 1.1 mmol) according to the method given above is subjected to column chromatography (R$_f$=0.38, DCM/MeOH=25:1, 1.5×30 cm, 25 g SiO$_2$) to afford 339 mg (86%) of the compound of formula 9b as a white solid, m.p. 242° C. —IR (KBr): u=3065 cm$^{-1}$, 2941, 1644, 1554, 1447, 1301, 1151, 1079, 763, 692. —$^1$H NMR (250 MHz, [D$_6$]DMSO): δ=1.11 (t, J=7.3, 3H), 1.62-1.81 (m, 2H), 2.12-2.44 (m, 3H), 2.71-3.02 (m, 3H), 7.41-7.74 (m, 6H), 7.91-8.21 (m, 4H), 12.7 (br. s, 1H, NH). —$^{13}$C NMR (62.9 MHz, [D$_6$]DMSO): δ=8.6 (+), 23.3 (−), 24.4 (−), 28.4 (−), 28.8 (−), 67.9 (C$_{quat}$), 116.2 (C-4a), 127.5 (+), 128.8 (+), 129.0 (+), 130.1 (+), 131.8 (+), 133.8 (C$_{ipso}$), 135.7 (+), 153.9 (C-8a), 160.7 (C-2/C-4), 164.4 (C-4/C-2). —MS (70 eV), m/z (%): 394 (1) [M$^+$], 253 (52) [M$^+$−SO$_2$Ph], 252 (100) [M$^+$−SO$_2$Ph−H], 237 (14), 211 (15), 104 (11).

6-Methyl-2-phenyl-7,8-dihydroquinazolin-4(3H)-one (see formula 11a): From the sulfone of formula 9a (265 mg, 0.7 mmol) and KOtBu (235 mg, 2.1 mmol) according to the GP-3 is obtained 160 mg (96%) of the compound of formula 11a as a pale yellow solid, m.p. 218° C., R$_f$=0.6 (hexane/EE=1:2). —IR (KBr): nu(tilde)=3031 cm$^{-1}$, 2924, 1636, 1506, 1436, 1314, 1182, 932, 772, 699. —$^1$H NMR (250 MHz, CDCl$_3$): δ=1.96 (s, 3H), 2.39 [t, J=9.1 Hz, 2H, C(7)-H], 2.89 [t, J=9.1 Hz, 2H, C(8)-H], 6.46 [s, 1H, C(5)-H], 7.42-7.61 (m, 3H), 8.18-8.36 (m, 2H), 13.3 (br. s, 1H, NH). —$^{13}$C NMR (62.9 MHz, CDCl$_3$): δ=23.4 (+), 28.3 (−), 29.9 (−), 114.3 (+, C-5), 117.8 (C-4a), 127.5 (+), 128.8 (+), 131.3 (+), 132.3 (C$_{ipso}$), 137.7 (+, C-6), 153.4 (C-8a), 159.4 (C-2/C-4), 161.9 (C-4/C-2). —MS (70 eV), m/z (%): 238 (100) [M$^+$] 237 (38), 223 (50) [M$^+$−Me], 194 (10) [M$^+$−CONH$_2$], 104 (14), 77 (10) [Ph$^+$].

6-Ethyl-2-phenyl-7,8-dihydroquinazolin-4(3H)-one (see formula 11b): From the sulfone of formula 9b (197 mg, 0.5 mmol) and KOtBu (168 mg, 1.5 mmol) according to the GP-3 is obtained 118 mg (98%) of the compound of formula 11b as a pale yellow solid m.p. 198° C., $R_f$=0.6 (hexane/EE=1:2). —IR (KBr): nu(tilde)=3020 cm$^{-1}$, 2955, 2922, 1630, 1532, 1321, 1098, 922, 699. —$^1$H NMR (250 MHz, CDCl$_3$): δ=1.16 (t, J=7.32 Hz, 3H), 2.26 (q, J=7.3 Hz, 2H), 2.40 [t, J=8.9 Hz, 2H, C(7)-H], 2.89 [t, J=8.9 Hz, 2H, C(8)-H], 6.47 [s, 2H, C(5)-H], 7.42-7.61 (m, 3H), 8.22-8.38 (m, 2H), 13.45 (br. s, 1H, NH). —$^{13}$C NMR (62.9 MHz, CDCl$_3$): δ=11.8 (+), 26.9 (−), 23.0 (−), 30.1 (−), 112.4 (+, C-5), 117.8 (C-4a), 127.5 (+), 128.7 (+), 131.3 (+), 132.3 (C-6), 143.2 ($C_{ipso}$), 153.4 (C-8a), 159.7 (C-2/C-4), 162.0 (C-4/C-2). —MS (70 eV), m/z (%): 252 (100) [M$^+$], 237 (80) [M$^+$−Me], 223 (25) [M$^+$−Et], 180 (20).

6-Methyl-2-phenyl-5,6,7,8-tetrahydroquinazolin-4(3H)-one (see formula 10a): The crude reaction mixture obtained from the compound of formula 11a (100 mg, 0.42 mmol), 22 mg of Pd/C in 25 mL of MeOH after 4 h according to the GP-4 affords 97 mg (96%) of the compound of formula 10a with m.p. 237° C. —IR (KBr): nu(tilde)=3072 cm$^{-1}$, 2948, 1641, 1507, 1316, 1073, 697. —$^1$H NMR (250 MHz, CDCl$_3$): δ=1.12 (d, $^3J_{H,H}$=6.5 Hz, 3H), 1.38-1.56 (m, 1H), 1.76-2.15 (m, 3H), 2.68-2.86 (m, 3H), 7.20-7.38 (m, 3H), 8.02-8.14 (m, 2H), 11.68 (br. s, 1H, NH). —$^{13}$C NMR (62.9 MHz, CDCl$_3$): δ=21.5 (+), 28.0 (+), 30.1 (−), 30.4 (−), 31.8 (−), 119.6 (C-4a), 127.5 (+), 128.8 (+), 131.3 (+), 132.4 ($C_{ipso}$), 153.3 (C-8a), 162.2 (C-2/C-4), 164.8 (C-4/C-2). —MS (70 eV), m/z (%): 240 (100) [M$^+$], 225 (90) [M$^+$−Me], 198 (49), 104 (31), 77 (16). —$C_{15}H_{16}N_2O$ (240.3): calcd. C, 74.97; H, 6.71; N, 11.66. found C, 74.77; H, 6.99; N, 11.53.

6-Ethyl-2-phenyl-5,6,7,8-tetrahydroquinazolin-4(3H)-one (see formula 10b): The crude reaction mixture obtained from the compound of formula 11b (76 mg, 0.30 mmol), 15 mg of Pd/C in 25 mL of MeOH after 4 h according to the GP-4 affords 74 mg (96%) of the compound of formula 10b with m.p. 221° C. —IR (KBr): nu(tilde)=2922 cm$^{-1}$, 1642, 1549, 1315, 919, 697. —$^1$H NMR (250 MHz, CDCl$_3$): δ=1.02 (t, J=7.3 Hz, 3H), 1.24-1.68 (m, 4H), 1.80-2.15 (m, 2H), 2.55-3.00 (m, 3H), 7.36-7.60 (m, 3H), 8.10-8.32 (m, 2H), 13.12 (br. s, 1H, NH). —$^{13}$C NMR (62.9 MHz, CDCl$_3$): δ=11.5 (+), 27.9 (−), 28.1 (−), 28.8 (−), 31.8 (−), 34.7 (+), 119.6 (C-4a), 127.5 (+), 128.7 (+), 131.3 (+), 132.4 ($C_{ipso}$), 153.2 (C-8a), 162.4 (C-2/C-4), 164.9 (C-4/C-2). —MS (70 eV), m/z (%): 254 (80) [M$^+$], 225 (100) [M$^+$−Et], 198 (36), 104 (22). —$C_{16}H_{18}N_2O$ (254.3): calcd. C, 75.56; H, 7.15; N, 11.01. found. C, 75.36; H, 7.45; N, 10.88.

6-Benzenesulfonyl-7-methyl-2-phenyl-6,6,7,8-tetrahydroquinazolin-4(3H)one (see formula 12): Into a 10 mL of pyrex tube the compound of formula 3a (99 mg, 0.5 mmol) and (E)-p-tolyl-1-propenyl sulfone (see formula 4-Me) (392 mg, 2 mmol) are added, and the tube is heated at 175° C. for 12 h. After cooling down to room temperature, the reaction mixture is dissolved in DCM/MeOH and subjected to column chromatography ($R_f$=0.40, hexane/EE=1:2) to yield 53 mg (27%) of the title compound as a white solid, m.p.=247° C. —IR (KBr): nu(tilde)=3034 cm$^{-1}$, 2927, 1653, 1507, 1302, 1142, 1018. —$^1$H NMR (250 MHz, CDCl$_3$): δ=1.26 (d, J=7.8 Hz, 3H), 2.41-2.76 (m, 4H), 2.88-3.04 (m, 1H), 3.13-3.36 (m, 1H), 7.32-7.55 (m, 6H), 7.72-7.82 (m, 2H), 8.06-8.16 (m, 2H), 12.8 (br. s, NH). —$^{13}$C NMR (62.9 MHz, CDCl$_3$): δ=20.4 (+), 21.7 (+), 27.2 (−), 37.3 (−), 63.2 (+), 115.6 (C-4a), 127.5 (+), 128.7 (+), 128.9 (+), 130.0 (+), 131.7 (+), 132.0 (+), 135.2 ($C_{ipso}$), 144.8 (C-8a), 154.1 (C-2), 163.7 (C-4). —MS (70 eV), m/z (%): 394 (2) [M$^+$], 239 (36), 238 (100), 223 (28), 180 (20).

6-Benzenesulfonyl-2-(morpholine-4-yl)-5,6,7,8-tetrahydroquinazolin-4(3H)-one (see formula 13a): In a 10 ml of pyrex bottle the compound of formula 5g (168 mg, 0.5 mmol) is mixed with 2 mL of morpholine. This bottle is tightly sealed and heated at 180° C. for 15 h. The reaction mixture is cooled to RT, excess of morpholine is removed in vacuo, and crude product is filtered through a pad of SiO$_2$ (2×3 cm, 10 g, DCM/MeOH=10:1) to yield 175 mg (93%) of the compound of formula 12a as a white solid, m.p.>250° C. —IR (KBr): nu(tilde)=2902 cm$^{-1}$, 2848, 1656, 1590, 1395, 1300, 1267, 1146, 1114, 979, 742, 722. —$^1$H NMR (250 MHz, [D$_6$]DMSO): δ=1.55-1.72 (m, 1H), 2.05-2.32 (m, 2H), 3.41-3.72 (m, 9H), 7.60-7.81 (m, 3H), 7.82-7.92 (m, 2H), 8.86 (br. s, 1H, NH). —$^{13}$C NMR (62.9 MHz, [D$_6$]DMSO): δ=21.5 (−), 21.7 (−), 44.8 (−), 58.1 (+), 65.8 (−), 128.7 (+), 129.8 (+), 134.3 (+), 137.2 ($C_{ipso}$) 151.9 (C-8a), 159.1 (C-2), 163.4 (C-4). —MS (70 eV), m/z (%): 375 (8) [M$^+$], 233 (100) [M$^+$−SO$_2$Ph], 202 (23), 176 (10). —$C_{18}H_{21}N_3O_4S$ (375.5): calcd. C, 57.58; H, 5.64; N, 11.19. found C, 57.26; H, 5.65; N, 11.53.

2-(4-benzylpiperazin-1-yl)-6-Benzenesulfonyl-5,6,7,8-tetrahydroquinazolin-4(3H)-one (see formula 13b): Following the method given above, the compound of formula 13b is obtained from the compound of formula 5g (750 mg, 2.23 mmol) and N-benzylpiperazine (1.57 g, 8.92 mmol) in 92% (953 mg) yield as a white solid, m.p.>250° C. —IR (KBr): nu(tilde)=2937 cm$^{-1}$, 2816, 1653, 1576, 1304, 1262, 1144, 745. —$^1$H NMR (250 MHz, [D$_6$]DMSO): 1.52-1.71 (m, 1H), 2.08-2.42 (m, 7H), 3.41-3.63 (m, 9H), 7.17-7.38 (m, 5H), 7.62-7.94 (m, 5H). —$^{13}$C NMR (50.3 MHz, [D$_6$]DMSO): δ=20.9 (−), 21.2 (−), 29.6 (−), 43.9 (−), 51.6 (−), 58.1 (+), 61.4 (−), 104.4 (C-4a), 126.4 (+), 127.6 (+), 128.0 (+), 128.3 (+), 128.9 (+), 133.4 (+), 137.1 ($C_{ipso}$), 137.5 ($C_{ipso}$), 152.5 (C-8a), 159.4 (C-2), 163.1 (C-4). —MS (70 eV), m/z (%): 464 (14) [M$^+$], 429 (12), 412 (16), 318 (68), 159 (96), 91 (100). —$C_{25}H_{28}N_4O_3S$ (464.6): calcd. C, 64.63; H, 6.07; N, 12.06. found C, 64.48; H, 6.17; N, 11.97.

6-Benzenesulfonyl-2-(4-methylpiperazin-1-yl)-5,6,7,8-tetrahydroquinazolin-4(3H)-one (see formula 13c): Following the method given above, the compound of formula 13c is obtained from the compound of formula 5g (336 mg, 1.00 mmol) and 2 mL of N-methyl piperazine in 91% yield (352 mg) as a white solid, m.p.>250° C. —IR (KBr): nu(tilde)=3232 cm$^{-1}$, 2930, 2797, 1631, 1585, 1301, 1266, 1147, 1083, 1003, 721. —$^1$H NMR (250 MHz, CDCl$_3$): δ=1.78-1.92 (m, 1H), 2.38 (s, 3H), 2.41 (m, 4H), 2.43-2.80 (m, 5H), 3.13-3.26 (m, 1H, CH), 3.68-3.81 (m, 4H), 7.52-7.71 (m, 3H), 8.89-8.98 (m, 2H) 11.42 (br. s, 1H, NH). —$^{13}$C NMR (50.3 MHz, [D$_6$]DMSO): δ=21.0 (−), 21.2 (−), 29.6 (−), 43.8 (−), 45.1 (+), 53.7 (−), 58.0 (+), 104.4 (C-4a), 128.0 (+), 129.0 (+), 133.4 (+), 137.1 ($C_{ipso}$), 152.6 (C-8a), 159.3 (C-2), 163.2 (C-4). —MS (70 eV), m/z (%): 388 (16) [M$^+$], 318 (100), 306 (24), 176 (74), 83 (55), 71 (26). —$C_{19}H_{22}N_4O_3S$ (388.5): calcd. C, 58.74; H, 6.23; N, 14.42. found C, 58.64; H, 6.14; N, 14.29.

2-(Morpholin-4-yl)-7,8-dihydroquinazolin-4(3H)-one (see formula 15a): To a suspension of the compound of formula 13a (175 mg, 0.47 mmol) in 10 mL of THF, KOtBu (264 mg, 2.35 mmol) is added and the reaction mixture is stirred at RT for 15 h. Then it is poured into a separating funnel containing 10 mL of sat. aq. NH$_4$Cl solution and extracted with DCM (3×15 mL). Organic solutions are dried in MgSO$_4$, and the solvent is removed in vacuo. The crude product is subjected to column chromatography ($R_f$=0.45, Et$_2$O/MeOH=25:1, 1.5×30 cm, 25 g SiO$_2$) to yield 60 mg (84%) of the compound of formula 15a as a white solid, m.p. 228-230° C. —IR (KBr): nu(tilde)=2924 cm$^{-1}$, 2849, 1637, 1585, 1382, 1263, 1171, 1115, 987, 862, 729. —$^1$H NMR (250 MHz, CDCl$_3$): δ=2.28-2.40 (m, 2H), 2.62 [t, J=9.6 Hz, 2H, C(8)-H], 3.81 (s, 8H), 6.45 [dt, J=9.7 and 4.3 Hz, 1H, C(6)-H], 6.73 [dt, J=9.7 and 1.8 Hz, 1H, C(5)-H], 12.12 (br. s, 1H, NH). —$^{13}$C NMR (62.9 MHz CDCl$_3$): δ=22.6 (−), 30.2 (−), 44.9 (−), 66.4 (−), 107.5 (C-4a), 119.6 (+, C-5), 122.1 (+, C-6), 152.4 (C-8a), 162.5 (C-2/C-4), 164.2 (C-4/C-2). —MS (70 eV), m/z (%): 234 (11) [M$^+$+1], 233 (100) [M$^+$], 202 (62)

[M+–CH₂OH], 188 (16), 176 (30). —C₁₂H₁₅N₃O₂ (233.3): calcd. C, 61.79; H, 6.48; N, 18.01. found C, 61.54; H, 6.72; N, 17.91.

2-(4-Benzylpiperazin-1-yl)-7,8-dihydroquinazolin-4 (3H)-one (see formula 15b): The crude product obtained from the compound of formula 13b (200 mg, 0.43 mmol) and KOtBu (480 mg, 4.30 mmol) according to the method given above, is subjected to column chromatography ($R_f$=0.41, DCM/MeOH=25:1, 1.5×30 cm, 25 g SiO₂) to yield 131 mg (94%) of the compound of formula 15b as a white solid, m.p.=196-197° C. —IR (KBr): nu(tilde)=3040 cm⁻¹, 2953, 1636, 1576, 1388, 1311, 1277, 1170, 1005, 848, 726. —¹H NMR (250 MHz, CDCl₃): δ=2.22-2.40 (m, 2H), 2.49-2.63 (m, 6H), 3.54 (s, 2H), 3.72-3.82 (m, 4H), 5.68 [dt, J=9.5 and 4.3 Hz, 1H, C(6)-H], 6.42 [dt, J=9.5 and 1.7 Hz, 1H, C(5)-H], 7.26-7.38 (m, 5H). —¹³C NMR (62.9 MHz, CDCl₃): δ=22.7 (–), 29.7 (–), 44.5 (–), 46.0 (–), 54.5 (–), 107.1 (C-4a), 119.8 (+, C-5), 121.6 (+, C-6), 127.2 (+), 128.3 (+), 137.6 ($C_{ipso}$), 152.2 (C-8a), 162.5 (C-2/C-4), 164.2 (C-4/C-2). —MS (70 eV), m/z (%): 322 (71) [M⁺], 189 (30), 176 (100), 146 (38), 91 (53). —C₁₉H₂₂N₄O (322.4): calcd. C, 70.78; H, 6.88; N, 17.38. found C, 70.45; H, 6.47; N, 17.50.

2-(4-Methylpiperazin-1-yl)-7,8-dihydroquinazolin-4 (3H)-one (see formula 15c): The crude product obtained from the compound of formula 13c (220 mg, 0.57 mmol) and KOtBu (638 mg, 5.70 mmol) according to the method given above, is subjected to column chromatography ($R_f$=0.40, DCM/MeOH=25:1, 1.5×20 cm, 25 g Al₂O₃) to yield 121 mg (94%) of the compound of formula 15c as a white solid, m.p.=188° C. —IR (KBr): nu(tilde)=3101 cm⁻¹, 2935, 2792, 1654, 1582, 1387, 1267, 1140, 1005, 727. —¹H NMR (250 MHz, CDCl₃): δ=2.21-2.38 (m, 5H), 2.41-2.54 (m, 4H), 2.55-2.66 (m, 2H), 3.64-3.81 (m, 4H), 5.72 [dt, J=9.7 and 4.3 Hz, 1H, C(6)-H], 6.48 [dt, J=9.7 and 1.8 Hz, 1H, C(5)-H]. —¹³C NMR (62.9 MHz, CDCl₃): δ=22.6 (–), 25.5 (–), 44.4 (–), 46.0 (+), 54.5 (–), 107.1 (C-4a), 119.8 (+, C-5), 121.6 (+, C-6), 156.9 (C-8a), 162.5 (C-2/C-4), 164.2 (C-4/C-2). —MS (70 eV), m/z (%): 246 (49) [M⁺], 189 (12), 176 (100). —C₁₃H₁₈N₄O (246.3): calcd. C, 62.39; H, 7.37; N, 22.75. found C, 62.37; H, 7.23; N, 22.59.

2-(Morpholin-4-yl)-5,6,7,8-tetrahydroquinazolin-4(3H)-one (see formula 14a): Into a 50 mL flame-dried reaction flask flushed with nitrogen, 15 mg of Pd/C (10% w/w) is added with 10 mL of MeOH. This mixture is stirred under H₂ for 30 min, at which point the compound of formula 15a (100 mg, 0.43 mmol) is added from the syringe, and stirring is continued for 15 h. The mixture is filtered through a pad of Celite®, and solvent is removed in vacuo to yield 97 mg (96%) of the compound of formula 14a as a white solid, m.p. 204-205° C. —IR (KBr): nu(tilde)=2925 cm⁻¹, 2856, 1640, 1576, 1386, 1270, 1165, 1121, 1001, 877, 767. —¹H NMR (200 MHz, CDCl₃): δ=1.63-1.90 (m, 4H), 2.30-2.42 (m, 2H), 2.43-2.58 (m, 2H), 3.56-3.92 (m, 8H), 11.6 (br. s, 1H, NH). —¹³C NMR (50.3 MHz, CDCl₃): δ=21.3 (–), 23.2 (–), 22.5 (–), 32.2 (–), 44.9 (–), 66.5 (–), 109.7 (C-4a), 156.6 (C-8a), 163.6 (C-2/C-4), 165.7 (C-4/C-2). —MS (70 eV), m/z (%): 235 (84) [M⁺], 204 (100) [M⁺–CH₂OH], 190 (40), 178 (90), 150 (47). —C₁₂H₁₇N₃O₂ (235.3): calcd. C, 61.26; H, 7.28; N, 17.86. found C, 61.41; H, 7.40; N, 17.65.

2-piperazin-1-yl-5,6,7,8-tetrahydroquinazolin-4(3H)-one (see formula 14b): Following the method given above, the compound of formula 14b is obtained from the compound of formula 15b (150 mg, 0.47 mmol) in 90% yield (99 mg) as a white solid, m.p.=121° C. —IR (KBr): nu(tilde)=2930 cm⁻¹, 1700, 1635, 1576, 1437, 1398, 1267, 998. —¹H NMR (250 MHz, CDCl₃): δ=1.60-1.82 (m, 4H), 2.28-2.54 (m, 4H), 2.84-3.02 (m, 4H), 3.62-3.71 (m, 4H), 11.81 (br. s, 1H, NH). —¹³C NMR (75.5 MHz, CDCl₃): δ=21.4 (–), 22.3 (–), 22.6 (–), 32.3 (–), 45.6 (–), 109.2 (C-4a), 151.7 (C-8a), 163.5 (C-2), 165.5 (C-4). —MS (70 eV), m/z (%): 234 (21) [M⁺], 192 (33), 178 (55), 166 (74), 72 (100).

2-(4-Methylpiperazin-1-yl)-5,6,7,8-tetrahydroquinazolin-4(3H)-one (see formula 14c): Following the method given above, the compound of formula 14c is obtained from the compound of formula 15c (100 mg, 0.41 mmol) in (83%) yield (84 mg) as a white solid, m.p. 210° C. —IR (KBr): nu(tilde)=3091 cm⁻¹, 2934, 2785, 1642, 1576, 1387, 1308, 1267, 1150, 1000, 845. —¹H NMR (250 MHz, CDCl₃): δ=1.61-1.80 (m, 4H), 2.24-2.40 (m, 5H), 2.42-2.58 (m, 6H), 3.64-3.74 (m, 4H), 11.81 (br. s, 1H, NH). —¹³C NMR (62.9 MHz, CDCl₃): δ=21.3 (–), 22.3 (–), 22.6 (–), 32.3 (–), 44.5 (–), 46.0 (+), 54.6 (–), 109.7 (C-4a), 151.5 (C-8a), 163.6 (C-2/C-4), 165.6 (C-4/C-2). —MS (70 eV), m/z (%): 248 (17) [M⁺], 178 (100), 166 (12), 83 (28), 71 (19). —C₁₃H₂₀N₄O (248.3): calcd. C, 62.88; H, 8.12; N, 22.56. found C, 62.59; H, 8.12; N, 22.40.

2-Dimethylamino-6-benzenesulfonyl-5,6,7,8-tetrahydroquinazolin-4(3H)-one (see formula 16): In a 10 ml pyrex bottle the compound of formula 5g (168 mg, 0.5 mmol) is dissolved in 2 mL of DMF. This bottle is tightly sealed and heated at 180° C. for 12 h. The reaction mixture is cooled to room temperature, excess of DMF is removed at reduced pressure, and the crude product is filtered through a pad of SiO₂ (2×3 cm, 10 g, DCM/MeOH=10:1) to yield 143 mg (86%) of the compound of formula 16 as a white solid, m.p.=249° C. —IR (KBr): nu(tilde)=2929 cm⁻¹, 1635, 1586, 1302, 1138, 1084. —¹H NMR (250 MHz, CDCl₃): δ=1.71-1.92 (m, 1H), 2.31-2.87 (m, 4H), 3.11 (s, 3H), 3.13-3.26 (m, 1H), 3.58-3.72 (m, 1H), 7.53-7.74 (m, 3H), 7.90-7.99 (m, 2H), 11.59 (br s, 1H, NH). —¹³C NMR (62.9 MHz, CDCl₃): δ=21.5 (–), 22.0 (–), 31.1 (–), 37.4 (+), 59.9 (+), 104.1 (C-4a), 128.9 (+), 129.1 (+), 133.8 (+), 137.1 ($C_{ipso}$), 152.5 (C-8a), 161.9 (C-2/C-4), 164.8 (C-4/C-2). —MS (70 eV), m/z (%): 333 (6) [M⁺], 192 (20), 191 (100), 162 (10), 77 (15).

EXAMPLE 8

Crystal structure of 6-Benzenesulfonyl-6-ethyl-2-phenyl-5,6,7,8-tetrahydroquinazolin-4(3H)-one See Formula 9b

TABLE 1

Crystal data and structure refinement for 6-Benzenesulfonyl-6-ethyl-2-phenyl-5,6,7,8-tetrahydroquinazolin-4(3H)-one (see formula 9b)

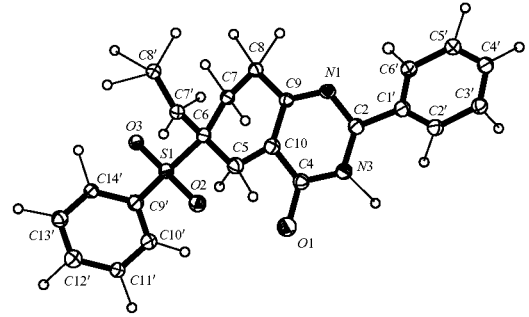

| | |
|---|---|
| Identification code | 9b |
| Empirical formula | C22 H22 N2 O3 S |
| Formula weight | 394.48 |
| Temperature | 100(2) K |
| Wavelength | 1.54178 Å |
| Crystal system | Monoclinic |
| Space group | P2(1)/c |
| Unit cell dimensions | a = 13.17(2) Å  α = 90°. |
| | b = 10.98(4) Å  β = 94.05(6)°. |
| | c = 13.03(3) Å  γ = 90°. |
| Volume | 1881(8) Å³ |
| Z | 4 |

TABLE 1-continued

Crystal data and structure refinement for 6-Benzenesulfonyl-6-ethyl-2-phenyl-5,6,7,8-tetrahydroquinazolin-4(3H)-one (see formula 9b)

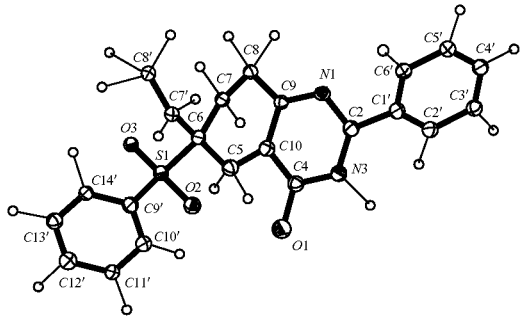

| | |
|---|---|
| Density (calculated) | 1.393 Mg/m³ |
| Absorption coefficient | 1.748 mm⁻¹ |
| F(000) | 832 |
| Crystal size | 0.2 × 0.2 × 0.2 mm³ |
| Theta range for data collection | 3.36 to 56.74°. |
| Index ranges | −14<=h<=12, −11<=k<=11, −14<=l<=14 |
| Reflections collected | 12555 |
| Independent reflections | 2461 [R(int) = 0.0525] |
| Completeness to theta = 56.74° | 98.0 % |
| Refinement method | Full-matrix least-squares on F² |
| Data/restraints/parameters | 2461/0/253 |
| Goodness-of-fit on F² | 1.035 |
| Final R indices [I>2sigma(I)] | R1 = 0.0366, wR2 = 0.0843 |
| R indices (all data) | R1 = 0.0493, wR2 = 0.0900 |
| Largest diff. peak and hole | 0.152 and −0.329 e.Å⁻³ |

TABLE 2

Atomic coordinates (×10⁴) and equivalent isotropic displacement parameters (Å² × 10³) for 6-Benzenesulfonyl-6-ethyl-2-phenyl-5,6,7,8-tetrahydroquinazolin-4(3H)-one (see formula 9b). U(eq) is defined as one third of the trace of the orthogonalized $U^{ij}$ tensor.

| | x | y | z | U(eq) |
|---|---|---|---|---|
| S(1) | 8017(1) | 2131(1) | 1182(1) | 32(1) |
| O(3) | 8944(1) | 2122(2) | 657(1) | 39(1) |
| N(1) | 8180(1) | −425(2) | 5217(1) | 24(1) |
| C(5') | 8347(2) | −1523(2) | 8313(1) | 30(1) |
| O(2) | 7734(1) | 3232(2) | 1692(1) | 37(1) |
| N(3) | 6404(1) | −352(2) | 5200(1) | 24(1) |
| C(4') | 7521(2) | −2115(2) | 8687(2) | 30(1) |
| O(1) | 5397(1) | 299(2) | 3809(1) | 29(1) |
| C(3') | 6628(2) | −2247(2) | 8066(2) | 29(1) |
| C(2') | 6556(2) | −1776(2) | 7080(2) | 26(1) |
| C(1') | 7379(2) | −1164(2) | 6703(2) | 24(1) |
| C(6') | 8277(2) | −1046(2) | 7330(2) | 28(1) |
| C(2) | 7337(2) | −625(2) | 5664(2) | 23(1) |
| C(4) | 6276(2) | 117(2) | 4218(2) | 24(1) |
| C(10) | 7192(2) | 368(2) | 3740(2) | 23(1) |
| C(9) | 8103(2) | 109(2) | 4261(2) | 24(1) |
| C(8) | 9089(2) | 382(2) | 3807(2) | 29(1) |
| C(7) | 8963(2) | 1290(2) | 2916(2) | 30(1) |
| C(6) | 8080(2) | 918(2) | 2143(2) | 28(1) |
| C(7') | 8217(2) | −346(2) | 1646(2) | 32(1) |
| C(5) | 7084(2) | 935(2) | 2684(2) | 26(1) |
| C(8') | 9249(2) | −660(3) | 1239(2) | 41(1) |
| C(9') | 7001(2) | 1744(2) | 280(2) | 31(1) |
| C(10') | 6002(2) | 1998(2) | 498(2) | 35(1) |
| C(11') | 5214(2) | 1663(3) | −211(2) | 41(1) |
| C(12') | 5426(2) | 1118(2) | −1128(2) | 40(1) |
| C(13') | 6419(2) | 903(2) | −1353(2) | 39(1) |
| C(14') | 7212(2) | 1199(2) | −641(2) | 35(1) |

TABLE 3

Bond lengths [Å] and angles [°] for 6-Benzenesulfonyl-6-ethyl-2-phenyl-5,6,7,8-tetrahydroquinazolin-4(3H)-one (see formula 9b).

| | |
|---|---|
| S(1)—O(3) | 1.441(3) |
| S(1)—O(2) | 1.442(4) |
| S(1)—C(9') | 1.769(3) |
| S(1)—C(6) | 1.827(4) |
| N(1)—C(2) | 1.308(3) |
| N(1)—C(9) | 1.375(4) |
| C(5')—C(6') | 1.382(4) |
| C(5')—C(4') | 1.384(4) |
| N(3)—C(2) | 1.364(3) |
| N(3)—C(4) | 1.379(4) |
| C(4')—C(3') | 1.387(4) |
| O(1)—C(4) | 1.257(3) |
| C(3')—C(2') | 1.383(4) |
| C(2')—C(1') | 1.394(4) |
| C(1')—C(6') | 1.395(4) |
| C(1')—C(2) | 1.476(4) |
| C(4)—C(10) | 1.422(4) |
| C(10)—C(9) | 1.367(4) |
| C(10)—C(5) | 1.508(4) |
| C(9)—C(8) | 1.496(4) |
| C(8)—C(7) | 1.531(4) |
| C(7)—C(6) | 1.540(4) |
| C(6)—C(5) | 1.534(4) |
| C(6)—C(7') | 1.547(5) |
| C(7')—C(8') | 1.533(4) |
| C(9')—C(14') | 1.387(4) |
| C(9')—C(10') | 1.394(4) |
| C(10')—C(11') | 1.390(4) |
| C(11')—C(12') | 1.382(4) |
| C(12')—C(13') | 1.381(4) |
| C(13')—C(14') | 1.387(4) |
| O(3)—S(1)—O(2) | 118.69(13) |
| O(3)—S(1)—C(9') | 108.02(18) |
| O(2)—S(1)—C(9') | 107.46(14) |
| O(3)—S(1)—C(6) | 108.74(13) |
| O(2)—S(1)—C(6) | 107.2(2) |
| C(9')—S(1)—C(6) | 106.01(17) |
| C(2)—N(1)—C(9) | 117.6(2) |
| C(6')—C(5')—C(4') | 120.1(2) |
| C(2)—N(3)—C(4) | 122.8(2) |
| C(5')—C(4')—C(3') | 119.9(2) |
| C(2')—C(3')—C(4') | 120.2(2) |
| C(3')—C(2')—C(1') | 120.3(2) |
| C(2')—C(1')—C(6') | 119.1(2) |
| C(2')—C(1')—C(2) | 122.5(2) |
| C(6')—C(1')—C(2) | 118.4(2) |
| C(5')—C(6')—C(1') | 120.4(2) |
| N(1)—C(2)—N(3) | 122.2(2) |
| N(1)—C(2)—C(1') | 119.8(2) |
| N(3)—C(2)—C(1') | 118.0(2) |
| O(1)—C(4)—N(3) | 120.1(2) |
| O(1)—C(4)—C(10) | 124.6(2) |
| N(3)—C(4)—C(10) | 115.2(2) |
| C(9)—C(10)—C(4) | 119.0(2) |
| C(9)—C(10)—C(5) | 124.2(2) |
| C(4)—C(10)—C(5) | 116.8(2) |
| C(10)—C(9)—N(1) | 123.0(2) |
| C(10)—C(9)—C(8) | 121.2(2) |
| N(1)—C(9)—C(8) | 115.7(2) |
| C(9)—C(8)—C(7) | 112.4(2) |
| C(8)—C(7)—C(6) | 111.1(2) |
| C(5)—C(6)—C(7) | 109.1(2) |
| C(5)—C(6)—C(7') | 109.5(2) |
| C(7)—C(6)—C(7') | 114.0(2) |
| C(5)—C(6)—S(1) | 107.91(17) |
| C(7)—C(6)—S(1) | 104.5(2) |
| C(7')—C(6)—S(1) | 111.6(3) |
| C(8')—C(7')—C(6) | 118.6(2) |
| C(10)—C(5)—C(6) | 112.7(2) |
| C(14')—C(9')—C(10') | 120.8(2) |
| C(14')—C(9')—S(1) | 119.4(2) |
| C(10')—C(9')—S(1) | 119.8(2) |
| C(11')—C(10')—C(9') | 118.9(3) |

TABLE 3-continued

Bond lengths [Å] and angles [°] for 6-Benzenesulfonyl-6-ethyl-2-phenyl-5,6,7,8-tetrahydroquinazolin-4(3H)-one (see formula 9b).

| | |
|---|---|
| C(12')—C(11')—C(10') | 120.2(3) |
| C(13')—C(12')—C(11') | 120.7(3) |
| C(12')—C(13')—C(14') | 119.8(3) |
| C(9')—C(14')—C(13') | 119.6(3) |

Symmetry transformations used to generate equivalent atoms.

TABLE 4

Anisotropic displacement parameters (Å$^2$ × 10$^3$) for 6-Benzenesulfonyl-6-ethyl-2-phenyl-5,6,7,8-tetrahydroquinazolin-4(3H)-one (see formula 9b). The anisotropic displacement factor exponent takes the form: $-2e^2[h^2a^{*2}U^{11} + \ldots + 2hka^*b^*U^{12}]$

| | $U^{11}$ | $U^{22}$ | $U^{33}$ | $U^{23}$ | $U^{13}$ | $U^{12}$ |
|---|---|---|---|---|---|---|
| S(1) | 32(1) | 34(1) | 31(1) | 7(1) | 7(1) | 1(1) |
| O(3) | 32(1) | 48(1) | 38(1) | 13(1) | 14(1) | 0(1) |
| N(1) | 22(1) | 28(1) | 23(1) | −1(1) | 3(1) | −1(1) |
| C(5') | 27(1) | 35(2) | 28(1) | 1(1) | −2(1) | 2(1) |
| O(2) | 45(1) | 32(1) | 36(1) | 4(1) | 7(1) | 0(1) |
| N(3) | 19(1) | 30(1) | 24(1) | 1(1) | 5(1) | −1(1) |
| C(4') | 34(2) | 30(1) | 26(1) | 5(1) | 2(1) | 5(1) |
| O(1) | 20(1) | 41(1) | 26(1) | 5(1) | 2(1) | 3(1) |
| C(3') | 28(1) | 28(1) | 33(1) | 4(1) | 8(1) | 3(1) |
| C(2') | 25(1) | 25(1) | 29(1) | 0(1) | 1(1) | 2(1) |
| C(1') | 23(1) | 24(1) | 25(1) | 0(1) | 3(1) | 3(1) |
| C(6') | 23(1) | 32(1) | 28(1) | 1(1) | 4(1) | 0(1) |
| C(2) | 21(1) | 23(1) | 24(1) | −3(1) | 0(1) | 0(1) |
| C(4) | 26(1) | 23(1) | 23(1) | −1(1) | 2(1) | 1(1) |
| C(10) | 23(1) | 24(1) | 23(1) | −1(1) | 5(1) | −1(1) |
| C(9) | 24(1) | 25(1) | 23(1) | −2(1) | 2(1) | −1(1) |
| C(8) | 22(1) | 39(2) | 27(1) | 1(1) | 2(1) | −1(1) |
| C(7) | 24(1) | 36(2) | 30(1) | 3(1) | 5(1) | −2(1) |
| C(6) | 23(1) | 35(2) | 26(1) | 6(1) | 5(1) | 1(1) |
| C(7') | 30(1) | 36(2) | 29(1) | 0(1) | 4(1) | 1(1) |
| C(5) | 23(1) | 29(1) | 26(1) | 3(1) | 2(1) | 0(1) |
| C(8') | 40(2) | 47(2) | 37(1) | −3(1) | 11(1) | 6(1) |
| C(9') | 33(2) | 30(1) | 29(1) | 9(1) | 5(1) | 5(1) |
| C(10') | 38(2) | 40(2) | 27(1) | 6(1) | 6(1) | 10(1) |
| C(11') | 36(2) | 51(2) | 36(2) | 11(1) | 2(1) | 10(1) |
| C(12') | 46(2) | 39(2) | 35(2) | 7(1) | −5(1) | 1(1) |
| C(13') | 54(2) | 31(2) | 32(1) | −1(1) | 5(1) | 5(1) |
| C(14') | 40(2) | 32(2) | 35(2) | 6(1) | 10(1) | 6(1) |

TABLE 5

Hydrogen coordinates (×10$^4$) and isotropic displacement parameters (Å$^2$ × 10$^3$) for 6-Benzenesulfonyl-6-ethyl-2-phenyl 5,6,7,8-tetrahydroquinazolin-4(3H)-one (see formula 9b).

| | x | y | z | U(eq) |
|---|---|---|---|---|
| H(1C) | 8962 | −1446 | 8733 | 36 |
| H(2B) | 5862 | −480 | 5541 | 29 |
| H(2C) | 7566 | −2429 | 9367 | 36 |
| H(3A) | 6065 | −2662 | 8320 | 35 |
| H(4A) | 5944 | −1870 | 6657 | 32 |
| H(6A) | 8843 | −634 | 7079 | 33 |
| H(11A) | 9380 | −385 | 3556 | 35 |
| H(11B) | 9575 | 718 | 4348 | 35 |
| H(12A) | 9602 | 1328 | 2560 | 36 |
| H(12B) | 8830 | 2111 | 3189 | 36 |
| H(14A) | 8067 | −971 | 2162 | 38 |
| H(14B) | 7693 | −426 | 1067 | 38 |
| H(01A) | 6854 | 1789 | 2747 | 31 |
| H(01B) | 6554 | 490 | 2257 | 31 |
| H(15A) | 9223 | −1484 | 950 | 61 |
| H(15B) | 9780 | −620 | 1804 | 61 |
| H(15C) | 9403 | −76 | 703 | 61 |
| H(17A) | 5862 | 2393 | 1121 | 42 |
| H(18A) | 4528 | 1808 | −65 | 49 |
| H(19A) | 4883 | 890 | −1608 | 48 |
| H(20A) | 6558 | 552 | −1995 | 46 |
| H(21A) | 7895 | 1030 | −783 | 42 |

EXAMPLE 9

Further Compounds Obtained by Manufacturing Procedures According to the Invention

| Comp. | Structure | MW | m/z (EI) |
|---|---|---|---|
| 1 | 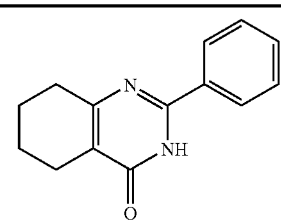 | 226.3 | 227 |
| 2 | 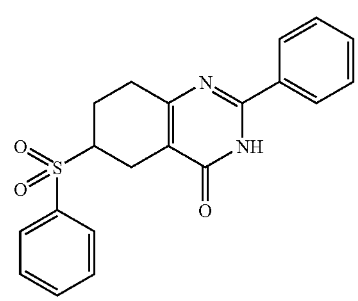 | 366.4 | 367 |

-continued

| Comp. | Structure | MW | m/z (EI) |
|---|---|---|---|
| 3 | 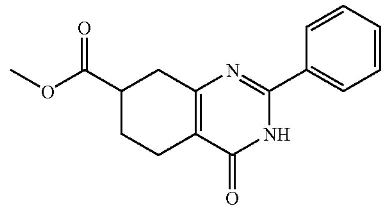 | 284.3 | 285 |
| 4 | 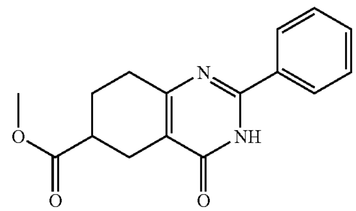 | 284.3 | 285 |
| 5 | 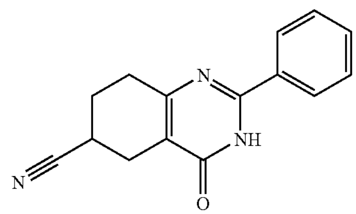 | 251.3 | 252 |
| 6 | 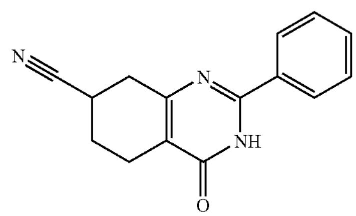 | 251.3 | 252 |
| 7 | 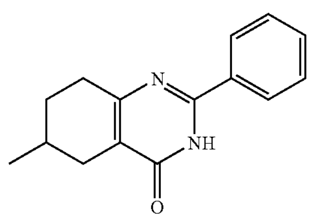 | 240.3 | 241 |
| 8 | 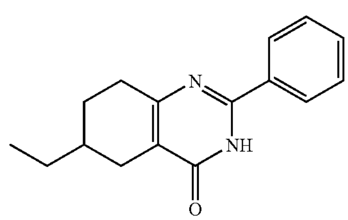 | 254.3 | 255 |
| 9 | 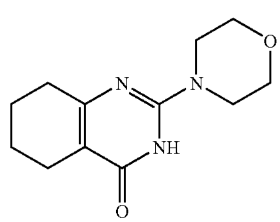 | 235.3 | 236 |

| Comp. | Structure | MW | m/z (EI) |
|---|---|---|---|
| 10 | 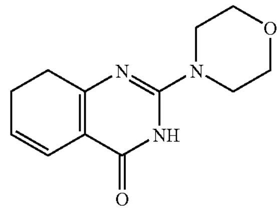 | 233.3 | 234 |
| 11 | 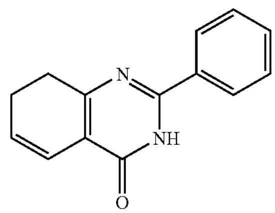 | 224.3 | 225 |
| 12 | 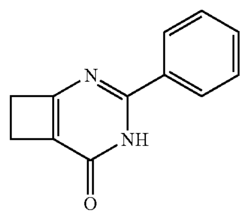 | 198.2 | 199 |
| 13 | 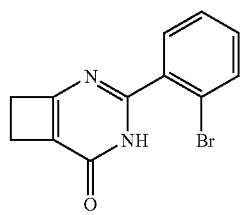 | 277.1 | 278 |
| 14 | 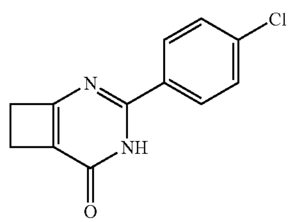 | 232.7 | 234 |
| 15 | 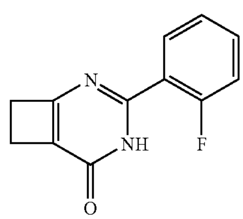 | 216.2 | 217 |
| 16 | 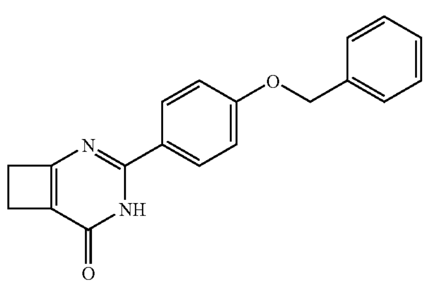 | 304.3 | 305 |

-continued

| Comp. | Structure | MW | m/z (EI) |
|---|---|---|---|
| 17 | 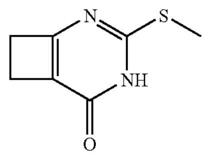 | 168.2 | 169 |
| 18 | 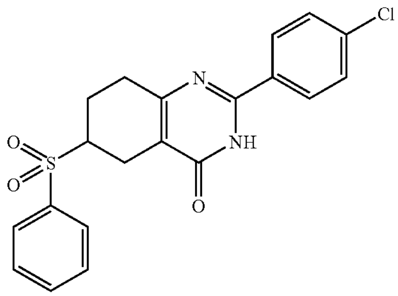 | 400.9 | 402 |
| 19 | 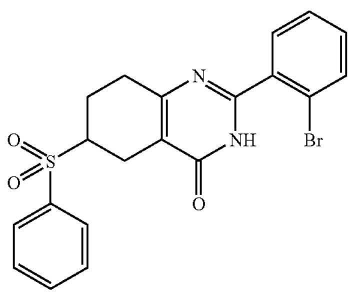 | 445.3 | 446 |
| 20 | 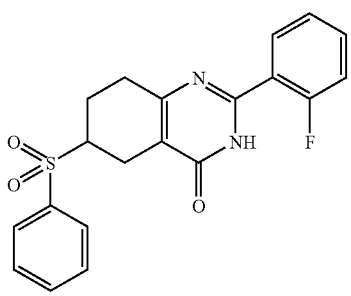 | 384.4 | 385 |
| 21 | 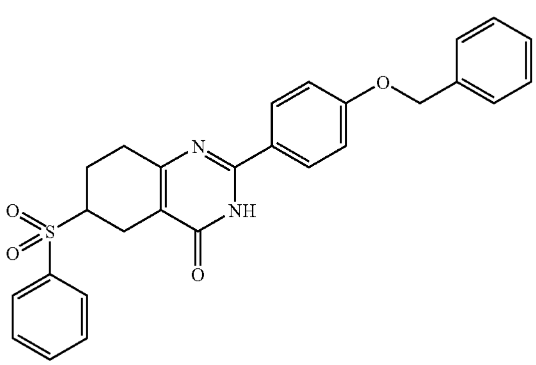 | 472.6 | 474 |

-continued

| Comp. | Structure | MW | m/z (EI) |
|---|---|---|---|
| 22 | 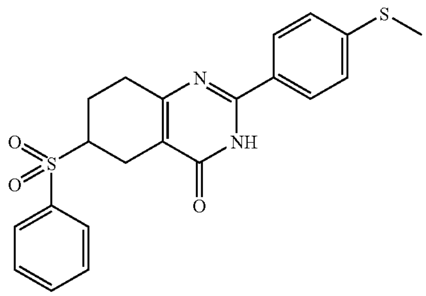 | 412.5 | 414 |
| 23 | 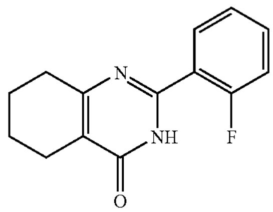 | 244.3 | 245 |
| 24 | 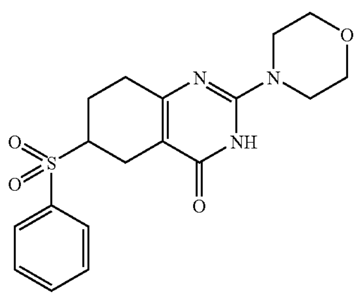 | 375.4 | 376 |
| 25 | 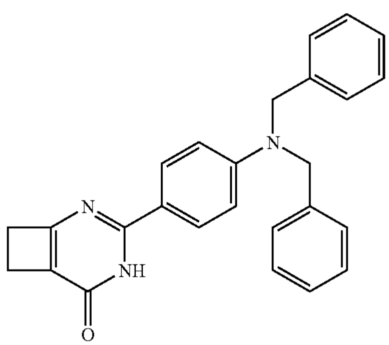 | 393.5 | 394 |
| 26 | 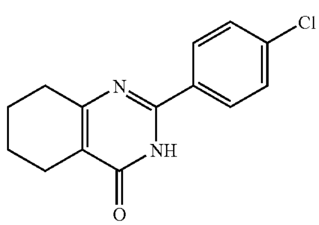 | 260.7 | 262 |

EXAMPLE 10

VEGF Receptor Kinase Assay

VEGF receptor kinase activity is measured by incorporation of radio-labelled phosphate into polyglutamic acid/tyrosine, 4:1 (pEY) substrate. The phosphorylated pEY product is trapped onto a filter membrane and the incorporation of radiolabelled phosphate is quantified by scintillation counting.

Materials

VEGF receptor kinase: The intracellular tyrosine kinase domains of human KDR (Terman, B. I. et al. Oncogene (1991) Vol. 6, pp. 1677-1683.) and Flt-1 (Shibuya, M. et al. Oncogene (1990) Vol. 5, pp. 519-524) were cloned as glutathione S-transferase (GST) gene fusion proteins. This was accomplished by cloning the cytoplasmic domain of the KDR kinase as an in frame fusion at the carboxyl terminus of the GST gene. Soluble recombinant GST-kinase domain fusion proteins are expressed in *Spodoptera frugiperda* (Sf21) insect cells (Invitrogen) using a baculovirus expression vector (pAcG2T, Pharmingen).

Lysis buffer: 50 mM Tris pH 7.4, 0.5 M NaCl, 5 mM DTT, 1 mM EDTA, 0.5% triton X-100, 10% glycerol, 10 mg/ml of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/ml of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/ml of each leupeptin, pepstatin and aprotinin and 1 mM phenylmethylsulfonyl fluoride.

10× reaction buffer: 200 mM Tris, pH 7.4, 1.0 M NaCl, 50 mM $MnCl_2$, 10 mM DTT and 5 mg/ml bovine serum albumin [BSA] (Sigma).

Enzyme dilution buffer: 50 mM Tris, pH 7.4, 0.1 M NaCl, 1 mM DTT, 10% glycerol, 100 mg/ml BSA.

10× substrate: 750 µg/ml poly(glutamic acid/tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates

Millipore #MAFC NOB, GF/C glass fibre 96 well plate.

Method A—Protein Purification

1. Sf21 cells are infected with recombinant virus at a multiplicity of infection of 5 virus particles/cell and grown at 27° C. for 48 hours.
2. All steps are performed at 4° C. Infected cells are harvested by centrifugation at 1000×g and lysed at 4° C. for 30 minutes with 1/10 volume of lysis buffer followed by centrifugation at 100,000×g for 1 hour. The supernatant is then passed over a glutathione Sepharose column (Pharmacia) equilibrated with lysis buffer and washed with 5 volumes of the same buffer followed by 5 volumes of wash buffer. Recombinant GST-KDR protein is eluted with wash buffer/10 mM reduced glutathione (Sigma) and dialysed against dialysis buffer.

Method B—VEGF Receptor Kinase Assay

1. Add 5 µl of inhibitor or control to the assay in 50% DMSO.
2. Add 35 µl of reaction mixture containing 5 µl of 10× reaction buffer, 5 µl 25 mM ATP/10 µCi [$^{33}$P]ATP (Amersham) and 5 µl of 10× substrate.
3. Start the reaction by the addition of 10 µl of KDR (25 nM) in enzyme dilution buffer.
4. Mix and incubate at room temperature for 15 minutes.
5. Stop the reaction by the addition of 50 µl of stop solution.
6. Incubate for 15 minutes at 4° C.
7. Transfer a 90 µl aliquot to filter plate.
8. Aspirate and wash 3 times with wash solution.
9. Add 30 µl of scintillation cocktail, seal plate and count in a Wallace Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (BFGF). The mitogenic response to VEGF or BFGF is determined by measuring the incorporation of [$^3$H]thymidine into cellular DNA.

Materials

HUVECs: HUVECs frozen as primary culture isolates are obtained from Clonetics Corp. Cells are maintained in endothelial growth medium (EGM; Clonetics) and are used for mitogenic assays at passages 3-7.

Culture plates: NUNCLON 96-well polystyrene tissue culture plates (NUNC #167008).

Assay medium: Dulbecco's modification of Eagle's medium containing 1 g/ml glucose (low-glucose DMEM; Mediatech) plus 10% (v/v) foetal bovine serum (Clonetics).

Test compounds: Working stock solutions of test compounds are diluted serially in 100% dimethyl sulfoxide (DMSO) to 400 times greater than their desired final concentrations. Final dilutions to 1× concentration are made directly into assay medium immediately prior to addition to cells.

10× growth factors: Solutions of human VEGF 165 (500 ng/ml; R&D Systems) and BFGF (10 ng/ml; R&D Systems) are prepared in assay medium.

10×[$^3$H]thymidine: [Methyl-$^3$H]thymidine (20 Ci/mmol; Dupont-NEN) is diluted to 80 µCi/ml in low-glucose DMEM.

Cell wash medium: Hank's balanced salt solution (Mediatech) containing 1 mg/ml bovine serum albumin (Boehringer-Mannheim).

Cell lysis solution: 1 N NaOH, 2% (w/v) $Na_2CO_3$.

Method 1

HUVEC monolayers maintained in EGM are harvested by trypsinisation and plated out at a density of 4000 cells per 100 µl of assay medium per well in 96-well plates. Cells growth is arrested for 24 hours at 37° C. in a humidified atmosphere containing 5% $CO_2$.

Method 2

Growth-arrest medium is replaced by 100 µl of assay medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

Method 3

After the 2-hour pre-treatment period, cells are stimulated by addition of 10 µl/well of either assay medium, 10×VEGF solution or 10×BFGF solution. Cells are then incubated at 37° C./5% $CO_2$.

Method 4

After 24 hours in the presence of growth factors, 10×[$^3$H]thymidine (10 µl/well) is added.

Method 5

Three days after addition of [$^3$H]thymidine, medium is removed by aspiration, and cells are washed twice with cell wash medium (400 µl/well followed by 200 µl/well). The washed, adherent cells are then solubilised by addition of cell lysis solution (100 µl/well) and warming to 37° C. for 30 minutes. Cell lysates are transferred to 7 ml glass scintillation vials containing 150 µl of water. Scintillation cocktail (5 ml/vial) is added, and cell-associated radioactivity is determined by liquid scintillation spectroscopy. According to these assays, the compounds of the formula I are inhibitors of VEGF and are thus suitable for the inhibition of angiogenesis, such as in the treatment of ocular diseases, for example diabetic retinopathy, and for the treatment of carcinomas, for example solid tumours. The present compounds inhibit VEGF-stimulated mitogenesis of human vascular endothelial cells in culture with IC 50 values of 0.01-5.0 µM. These compounds also show selectivity over related tyrosine kinases (for example, FGFR1 and the Src family; for relationship between Src kinases and VEGFR kinases, see Eliceiri et al., Molecular Cell, Vol. 4, pp. 915-924, December 1999).

EXAMPLE 11

Injection Vials

A solution of 100 g of an active compound of the present invention and 5 g of disodium hydrogenphosphate is adjusted

EXAMPLE 12

Suppositories

A mixture of 20 g of an active compound of the present invention is fused with 100 g of soya lecithin and 1400 g of cocoa butter, poured into moulds and allowed to cool. Each suppository contains 20 mg of active compound.

EXAMPLE 13

Solution

A solution of 1 g of an active compound of the present invention, 9.38 g of $NaH_2PO_4.2H_2O$, 28.48 g of $Na_2HPO_4.12H_2O$ and 0.1 g of benzalkonium chloride in 940 ml of double-distilled water is prepared. It is adjusted to pH 6.8, made up to 1 l and sterilized by irradiation. This solution can be used in the form of eye drops.

EXAMPLE 14

Ointment 500 mg of an active compound of the present invention is mixed with 99.5 g of petroleum jelly under aseptic conditions.

EXAMPLE 15

Tablets

A mixture of 1 kg of active compound of the present invention, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE 16

Coated Tablets

Analogously to Example E, tablets are pressed and are then coated in a customary manner using a coating of sucrose, potato starch, talc, tragacanth and colourant.

EXAMPLE 17

Capsules 2 kg of active compound of the present invention are dispensed into hard gelatin capsules in a customary manner such that each capsule contains 20 mg of the active compound.

to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

The invention claimed is:

1. A compound of formula IV,

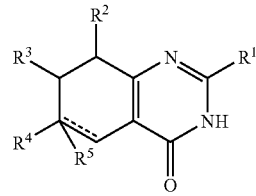

wherein
----- is a single or a double bond,
$R^1$ is $Ar^1$,
$R^2$ is H or A,
$R^3$ is H, CN, COOA, $(CH_2)_n NHA$, $(CH_2)_n NA_2$, $CONH_2$, $CONHA$, $CONA_2$, $(CH_2)_n NHCONH_2$, $(CH_2)_n NHCONHA$ or $(CH_2)_n NHCONA_2$,
$R^4$ is H, $SO_2Ar^2$, or A,
$R^5$ is H or A, or is absent, if ----- is a double bond,
$Ar^1$ is phenyl, which is optionally substituted by one or more substituents selected from the group consisting of Hal, S-A, Ph, —$O(CH_2)_n$-Ph and —$N(CH_2Ph)_2$,
$Ar^2$ is phenyl, which is optionally substituted by one or more substituents selected from the group consisting of Hal, A and COOA,
A is alkyl with 1-12 C-atoms or cycloalkyl with 3-12 C-atoms, wherein optionally 1-5 H atoms are replaced by F and/or Cl,
Hal is F, Cl, Br or I, and
n is 0, 1 or 2,
with the provisos that
at least one of $R^3$, $R^4$ and $R^5$ must have a meaning other than H or ----- is a double bond, and if
----- is a single bond,
$R^4$ is $SO_2Ar^2$, and
$R^5$ is H or A,
and if
----- is a double bond,
$R^4$ is H or A, and
$R^5$ is absent,
or a pharmaceutically acceptable salt, or stereoisomer thereof, or a mixture thereof.

2. A compound according to claim 1, wherein
----- is a single bond,
$R^2$, $R^3$, $R^5$ are H, and
$R^4$ is $SO_2Ar^2$,
or a pharmaceutically acceptable salt, or stereoisomer thereof, or a mixture thereof.

3. A compound selected from the group consisting of
6-Benzenesulfonyl-2-phenyl-5,6,7,8-tetrahydroquinazolin-4(3H)-one
6-Benzenesulfonyl-2-(p-chlorophenyl)-5,6,7,8-tetrahydroquinazolin-4(3H)-one
6-Benzenesulfonyl-2-(o-bromophenyl)-5,6,7,8-tetrahydroquinazolin-4(3H)-one
6-Benzenesulfonyl-2-(o-fluorophenyl)-5,6,7,8-tetrahydroquinazolin-4(3H)-one
6-Benzenesulfonyl-2-[(p-benzyloxy)phenyl]-5,6,7,8-tetrahydroquinazolin-4(3H)one
6-Benzenesulfonyl-2-(o-biphenyl)-5,6,7,8-tetrahydroquinazolin-4(3H)-one
2-Phenyl-7,8-dihydroquinazolin-4(3H)-one
2-(p-Chlorophenyl)-7,8-dihydroquinazolin-4(3H)-one
2-(o-Bromophenyl)-7,8-dihydroquinazolin-4(3H)-one
2-(o-Fluorophenyl)-7,8-dihydroquinazolin-4(3H)-one
2-(p-Benzoyloxyphenyl)-7,8-dihydroquinazolin-4(3H)-one
2-(o-Biphenyl)-7,8-dihydroquinazolin-4(3H)-one 6-Benzenesulfonyl-6-methyl-2-phenyl-5,6,7,8-tetrahydroquinazolin-4(3H)-one
6-Benzenesulfonyl-6-ethyl-2-phenyl-5,6,7,8-tetrahydroquinazolin-4(3H)-one
6-Methyl-2-phenyl-7,8-dihydroquinazolin-4(3H)-one
6-Ethyl-2-phenyl-7,8-dihydroquinazolin-4(3H)-one and
6-Benzenesulfonyl-7-methyl-2-phenyl-5,6,7,8-tetrahydroquinazolin-4(3H)one and the physiologically acceptable salts, and stereoisomers thereof, and mixtures thereof in all ratios.

4. A pharmaceutical composition, comprising a compound according to claim 1 and a pharmaceutically acceptable carrier.

5. A compound according to claim 1, or a pharmaceutically acceptable salt thereof.

6. A compound according to claim 3, or a pharmaceutically acceptable salt thereof.

7. A compound according to claim 1, wherein
A is alkyl with 3-12 C-atoms or cycloalkyl with 3-12 C-atoms, wherein optionally 1-5H atoms are replaced by F and/or Cl,
or a pharmaceutically acceptable salt, or stereoisomer thereof, or a mixture thereof.

8. A compound according to claim 1, wherein
A is alkyl or cycloalkyl with 4-12 C-atoms, wherein optionally 1-5H atoms are replaced by F and/or Cl,
or a pharmaceutically acceptable salt, or stereoisomer thereof, or a mixture thereof.

9. A compound according to claim 1, wherein
$R^3$ is H, $(CH_2)_n NHA$, $(CH_2)_n NA_2$, $CONH_2$, $CONHA$, $CONA_2$, $(CH_2)_n NHCONH_2$, $(CH_2)_n NHCONHA$ or $(CH_2)_n NHCONA_2$,
or a pharmaceutically acceptable salt, or stereoisomer thereof, or a mixture thereof.

10. A compound according to claim 3 selected from the group consisting of
6-Benzenesulfonyl-2-phenyl-5,6,7,8-tetrahydroquinazolin-4(3H)-one
6-Benzenesulfonyl-2-(p-chlorophenyl)-5,6,7,8-tetrahydroquinazolin-4(3H)-one
6-Benzenesulfonyl-2-(o-bromophenyl)-5,6,7,8-tetrahydroquinazolin-4(3H)-one
6-Benzenesulfonyl-2-(o-fluorophenyl)-5,6,7,8-tetrahydroquinazolin-4(3H)-one
6-Benzenesulfonyl-2-[(p-benzyloxy)phenyl]-5,6,7,8-tetrahydroquinazolin-4(3H)one
6-Benzenesulfonyl-2-(o-biphenyl)-5,6,7,8-tetrahydroquinazolin-4(3H)-one
6-Benzenesulfonyl-6-methyl-2-phenyl-5,6,7,8-tetrahydroquinazolin-4(3H)-one
6-Benzenesulfonyl-6-ethyl-2-phenyl-5,6,7,8-tetrahydroquinazolin-4(3H)-one and
6-Benzenesulfonyl-7-methyl-2-phenyl-5,6,7,8-tetrahydroquinazolin-4(3H)one and the physiologically acceptable salts, and stereoisomers thereof, and mixtures thereof in all ratios.

11. A compound according to claim 3 selected from the group consisting of
2-Phenyl-7,8-dihydroquinazolin-4(3H)-one
2-(p-Chlorophenyl)-7,8-dihydroquinazolin-4(3H)-one
2-(o-Bromophenyl)-7,8-dihydroquinazolin-4(3H)-one
2-(o-Fluorophenyl)-7,8-dihydroquinazolin-4(3H)-one
2-(p-Benzoyloxyphenyl)-7,8-dihydroquinazolin-4(3H)-one
2-(o-Biphenyl)-7,8-dihydroquinazolin-4(3H)-one
6-Methyl-2-phenyl-7,8-dihydroquinazolin-4(3H)-one and
6-Ethyl-2-phenyl-7,8-dihydroquinazolin-4(3H)-one and the physiologically acceptable salts, and stereoisomers thereof, and mixtures thereof in all ratios.

12. A compound according to claim 3 selected from the group consisting of
2-Phenyl-7,8-dihydroquinazolin-4(3H)-one
2-(p-Chlorophenyl)-7,8-dihydroquinazolin-4(3H)-one
2-(o-Bromophenyl)-7,8-dihydroquinazolin-4(3H)-one
2-(o-Fluorophenyl)-7,8-dihydroquinazolin-4(3H)-one
2-(p-Benzoyloxyphenyl)-7,8-dihydroquinazolin-4(3H)-one and
2-(o-Biphenyl)-7,8-dihydroquinazolin-4(3H)-one and the physiologically acceptable salts, and stereoisomers thereof, and mixtures thereof in all ratios.

13. A pharmaceutical composition, comprising a compound according to claim 3 and a pharmaceutically acceptable carrier.

14. A compound according to claim 1, wherein
----- is a single bond,
or a pharmaceutically acceptable salt, or stereoisomer thereof, or a mixture thereof.

15. A compound according to claim 1, wherein
----- is a double bond,
or a pharmaceutically acceptable salt, or stereoisomer thereof, or a mixture thereof.

16. A compound according to claim 1, wherein
----- is a double bond,
$R^2$, $R^3$, $R^4$ are H,
$R^5$ is absent,
or a pharmaceutically acceptable salt, or stereoisomer thereof, or a mixture thereof.

17. A compound according to claim 1, wherein
----- is a single bond,
$R^1$ is phenyl,
$R^2$, $R^3$ are H,
$R^4$ is $SO_2Ar^2$,
$R^5$ is A,
or a pharmaceutically acceptable salt, or stereoisomer thereof, or a mixture thereof.

18. A compound according to claim 1, wherein
----- is a double bond,
$R^1$ is phenyl,
$R^2$, $R^3$ are H,
$R^4$ is A,
$R^5$ is absent,
or a pharmaceutically acceptable salt, or stereoisomer thereof, or a mixture thereof.

19. A compound selected from the group consisting of
6-Benzenesulfonyl-2-phenyl-5,6,7,8-tetrahydroquinazolin-4(3H)-one
6-Benzenesulfonyl-2-(p-chlorophenyl)-5,6,7,8-tetrahydroquinazolin-4(3H)-one
6-Benzenesulfonyl-2-(o-bromophenyl)-5,6,7,8-tetrahydroquinazolin-4(3H)-one
6-Benzenesulfonyl-2-(o-fluorophenyl)-5,6,7,8-tetrahydroquinazolin-4(3H)-one
6-Benzenesulfonyl-2-[(p-benzyloxy)phenyl]-5,6,7,8-tetrahydroquinazolin-4(3H)one
6-Benzenesulfonyl-2-(o-biphenyl)-5,6,7,8-tetrahydroquinazolin-4(3H)-one
2-Phenyl-7,8-dihydroquinazolin-4(3H)-one
2-(p-Chlorophenyl)-7,8-dihydroquinazolin-4(3H)-one
2-(o-Bromophenyl)-7,8-dihydroquinazolin-4(3H)-one
2-(o-Fluorophenyl)-7,8-dihydroquinazolin-4(3H)-one
2-(p-Benzoyloxyphenyl)-7,8-dihydroquinazolin-4(3H)-one
2-(o-Biphenyl)-7,8-dihydroquinazolin-4(3H)-one
6-Benzenesulfonyl-6-methyl-2-phenyl-5,6,7,8-tetrahydroquinazolin-4(3H)-one
6-Benzenesulfonyl-6-ethyl-2-phenyl-5,6,7,8-tetrahydroquinazolin-4(3H)-one
6-Methyl-2-phenyl-7,8-dihydroquinazolin-4(3H)-one and
6-Ethyl-2-phenyl-7,8-dihydroquinazolin-4(3H)-one and the physiologically acceptable salts, and stereoisomers thereof, and mixtures thereof in all ratios.

* * * * *